(12) United States Patent
Wang et al.

(10) Patent No.: US 10,221,459 B2
(45) Date of Patent: Mar. 5, 2019

(54) COMPOSITIONS AND METHODS OF TREATING CANCER HARBORING PIKC3A MUTATIONS

(71) Applicant: Case Western Reserve University, Cleveland, OH (US)

(72) Inventors: Zhengne Wang, Cleveland, OH (US); Yujun Hao, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/711,507

(22) Filed: May 13, 2015

(65) Prior Publication Data

US 2016/0010158 A1    Jan. 14, 2016

Related U.S. Application Data

(60) Provisional application No. 61/992,541, filed on May 13, 2014.

(51) Int. Cl.

| C12Q 1/6886 | (2018.01) |
| G01N 33/574 | (2006.01) |
| A61K 31/353 | (2006.01) |
| A61K 31/195 | (2006.01) |
| A61K 31/433 | (2006.01) |
| A61K 31/501 | (2006.01) |

(52) U.S. Cl.
CPC .......... *C12Q 1/6886* (2013.01); *A61K 31/195* (2013.01); *A61K 31/353* (2013.01); *A61K 31/433* (2013.01); *A61K 31/501* (2013.01); *G01N 33/57484* (2013.01); *C12Q 2600/106* (2013.01); *C12Q 2600/156* (2013.01); *C12Q 2600/158* (2013.01); *G01N 2333/91215* (2013.01); *G01N 2800/52* (2013.01)

(58) Field of Classification Search
None
See application file for complete search history.

(56) References Cited

PUBLICATIONS

Liedtke et al (Breast Cancer Research, 2008, 10: R27, pp. 1-10).*
Gross et al (Mol Cancer Ther, 2014, 13(4): 890-901).*
Koninki et al (Cancer Letters, 2010, 294: 211-219).*
Fujiki et al (Mutation Research, 1998, 402(307-310).*
Samuels et al (Curr Top Microbiol Immunol, 2010, 347: 21-41).*
Saal et al (Cancer Res, 2005, 65(7): 2554-2559).*
Shimizu et al (Int J Mol Sci, 2008, 9: 1034-1049).*
Weigelt et al (Oncogene, 2011, 30: 3222-3233).*
Van der Vos et al (Autophagy, 2012, 8(12): 1862-1864).*
Tanaka et al (Clin Cancer Res, 17(10): 3272-3281).*
Winer (Oncology, 1998, (10 Suppl 7): 39-43; pp. 1-7).*
Tipoe et al (Toxicology, 2010, 273: 45-52).*
Thornburg et al (Breast Cancer Res, 2008, 10(5): R84; 12 pages).*

* cited by examiner

*Primary Examiner* — Sean E Aeder
(74) *Attorney, Agent, or Firm* — Tarolli, Sundheim, Covell & Tummino LLP

(57) ABSTRACT

A method of treating cancer cells having mutated PIK3CA gene or protein of a subject in need thereof includes administering to the subject a therapeutically effective amount of an inhibitor of one or more enzymes of the glutamine metabolism pathway.

19 Claims, 13 Drawing Sheets
Specification includes a Sequence Listing.

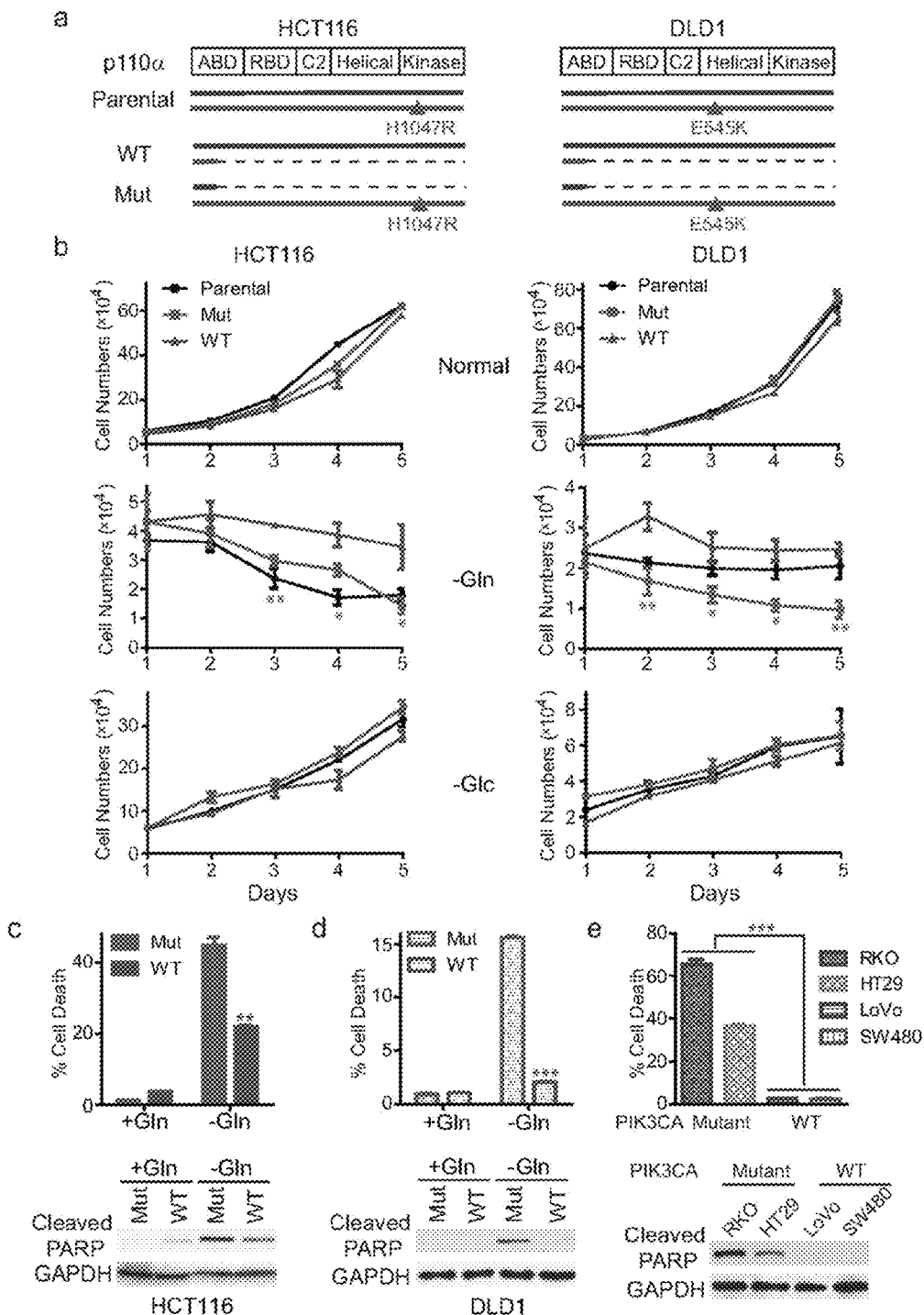
Figs. 2A-E

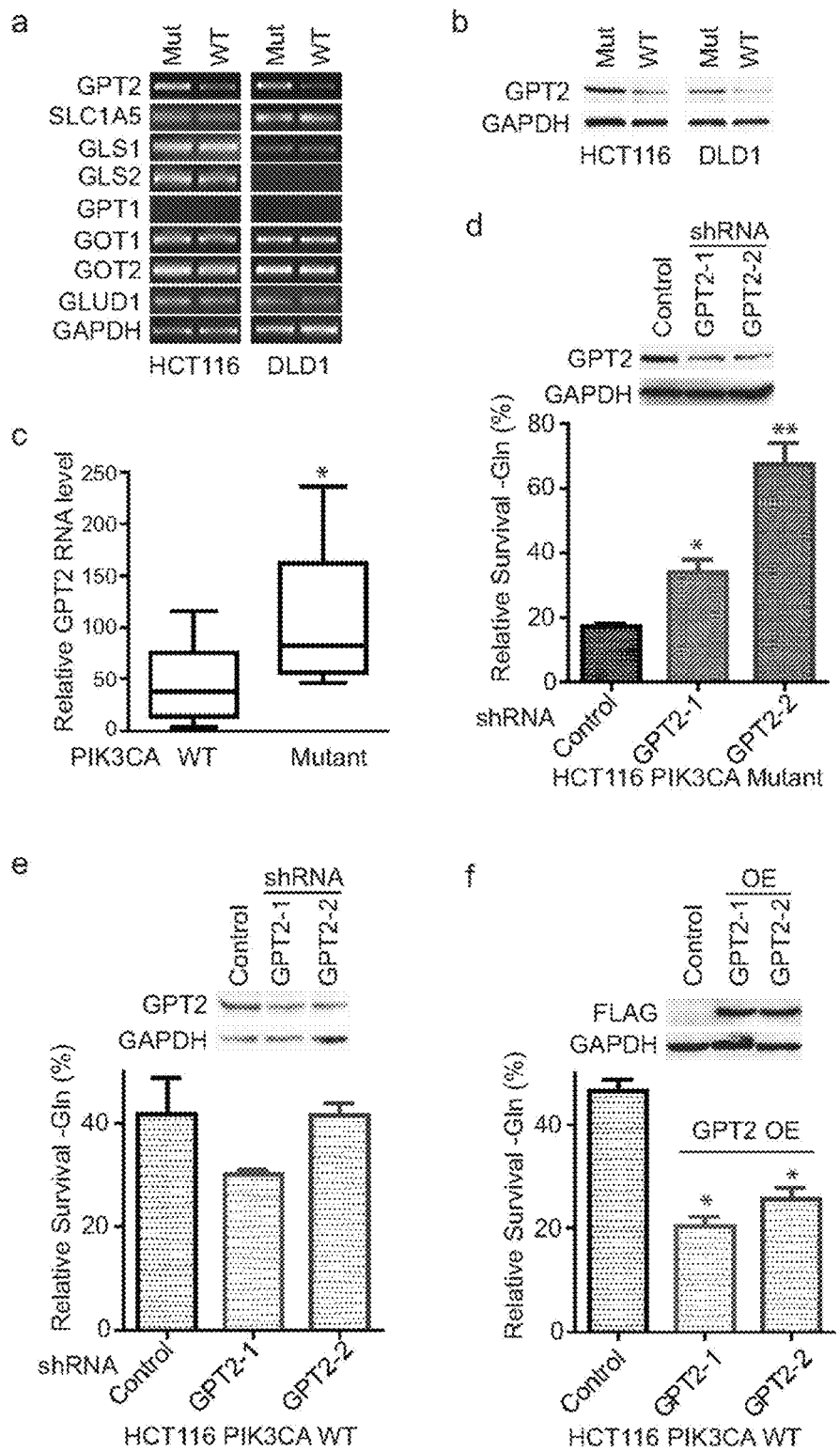
Figs. 3A-F

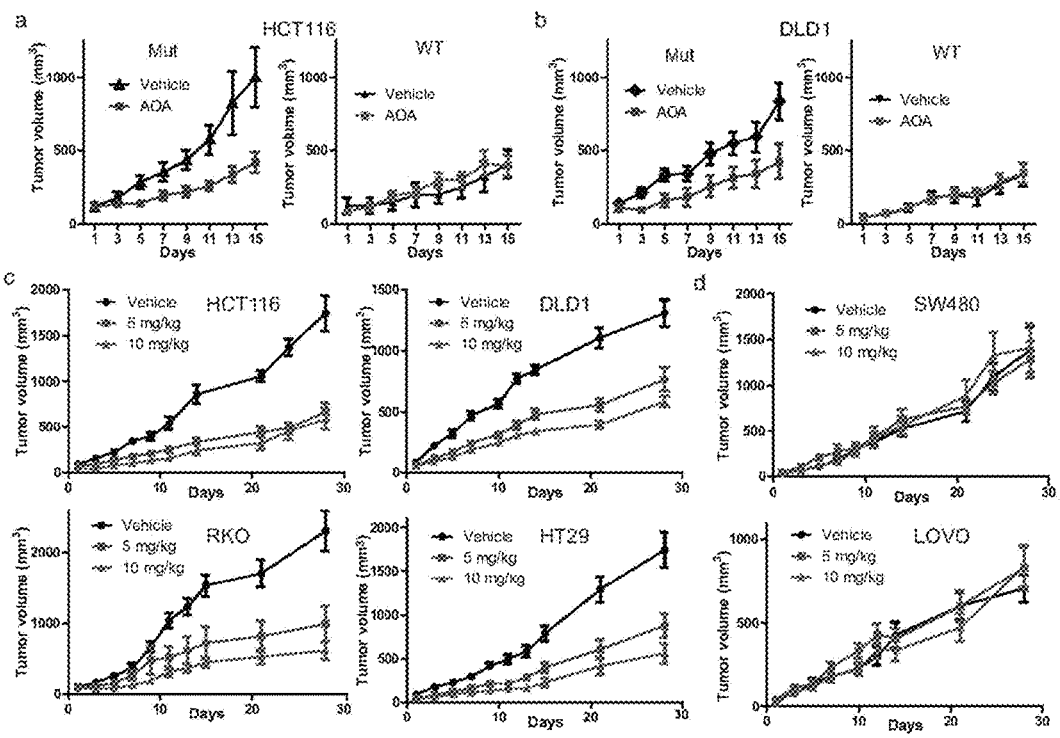
Figs. 4A-D

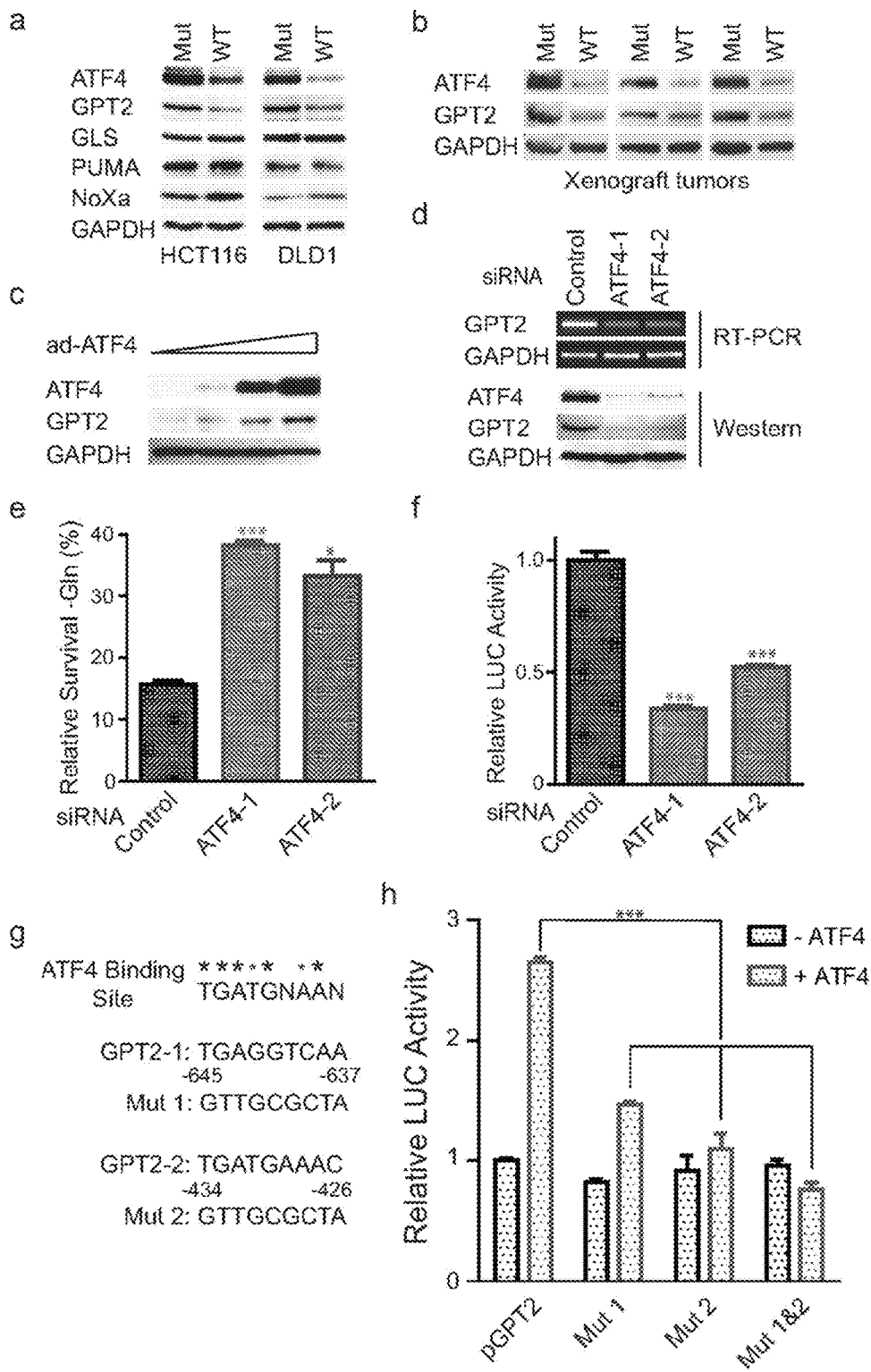
Figs. 5A-H

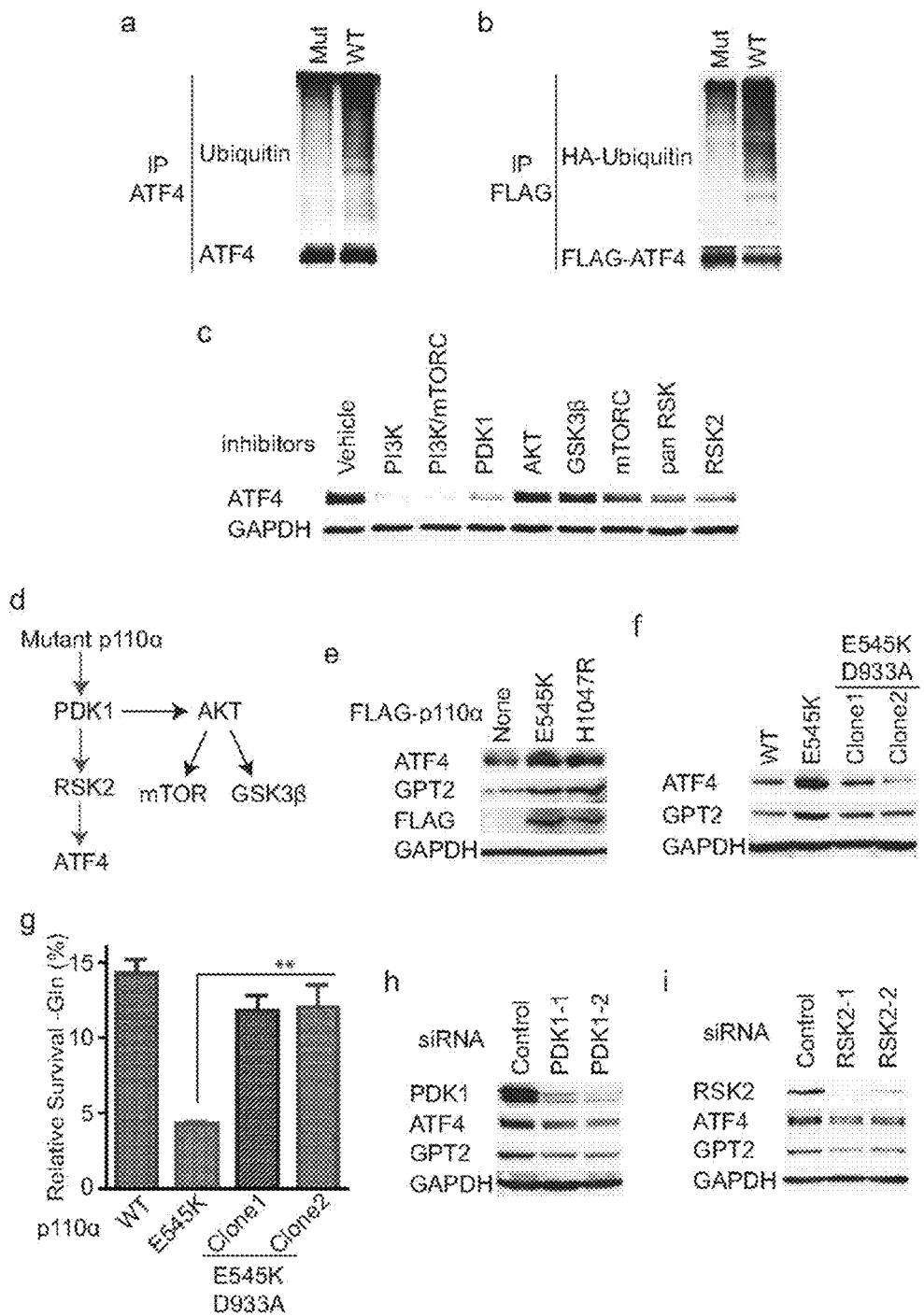
Figs. 6A-I

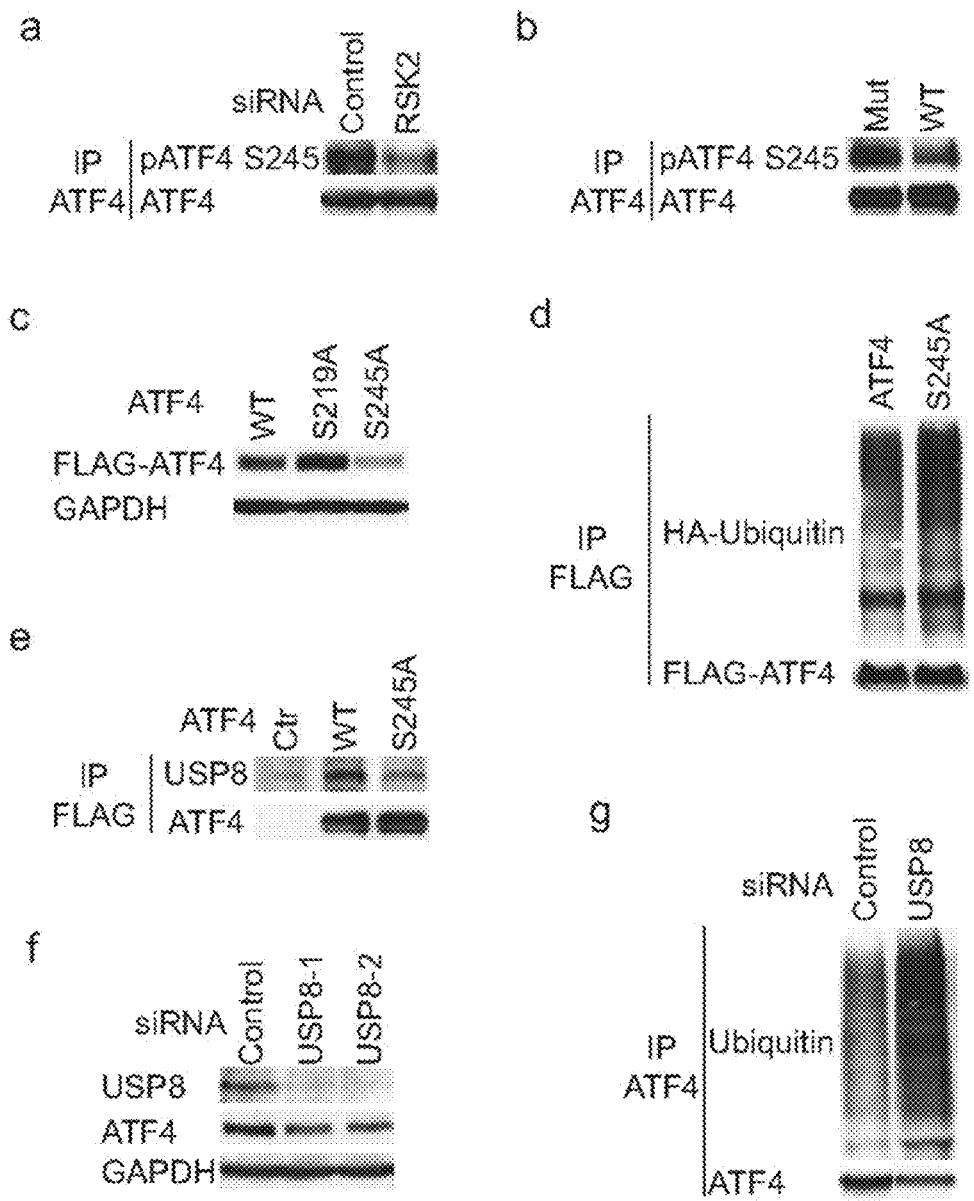
Figs. 7A-G

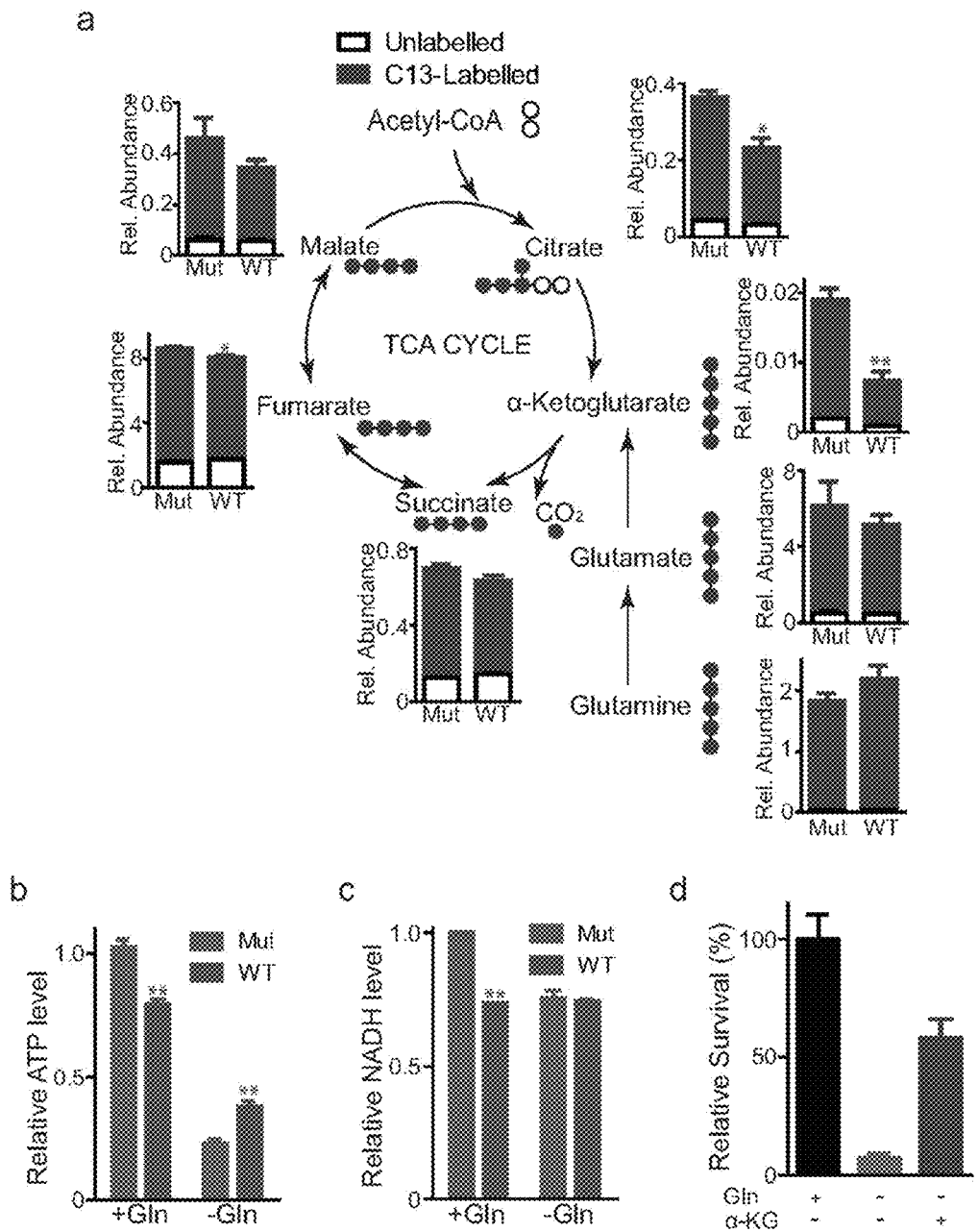
Figs. 8A-D

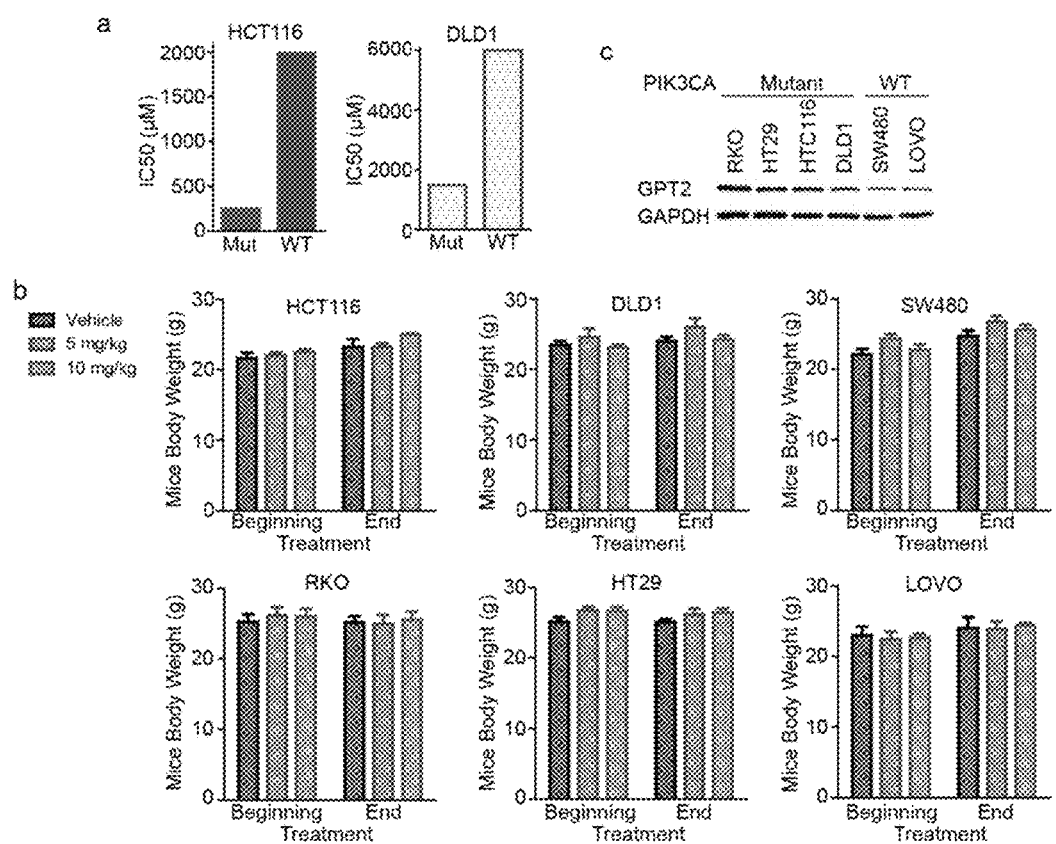
Figs. 9A-C

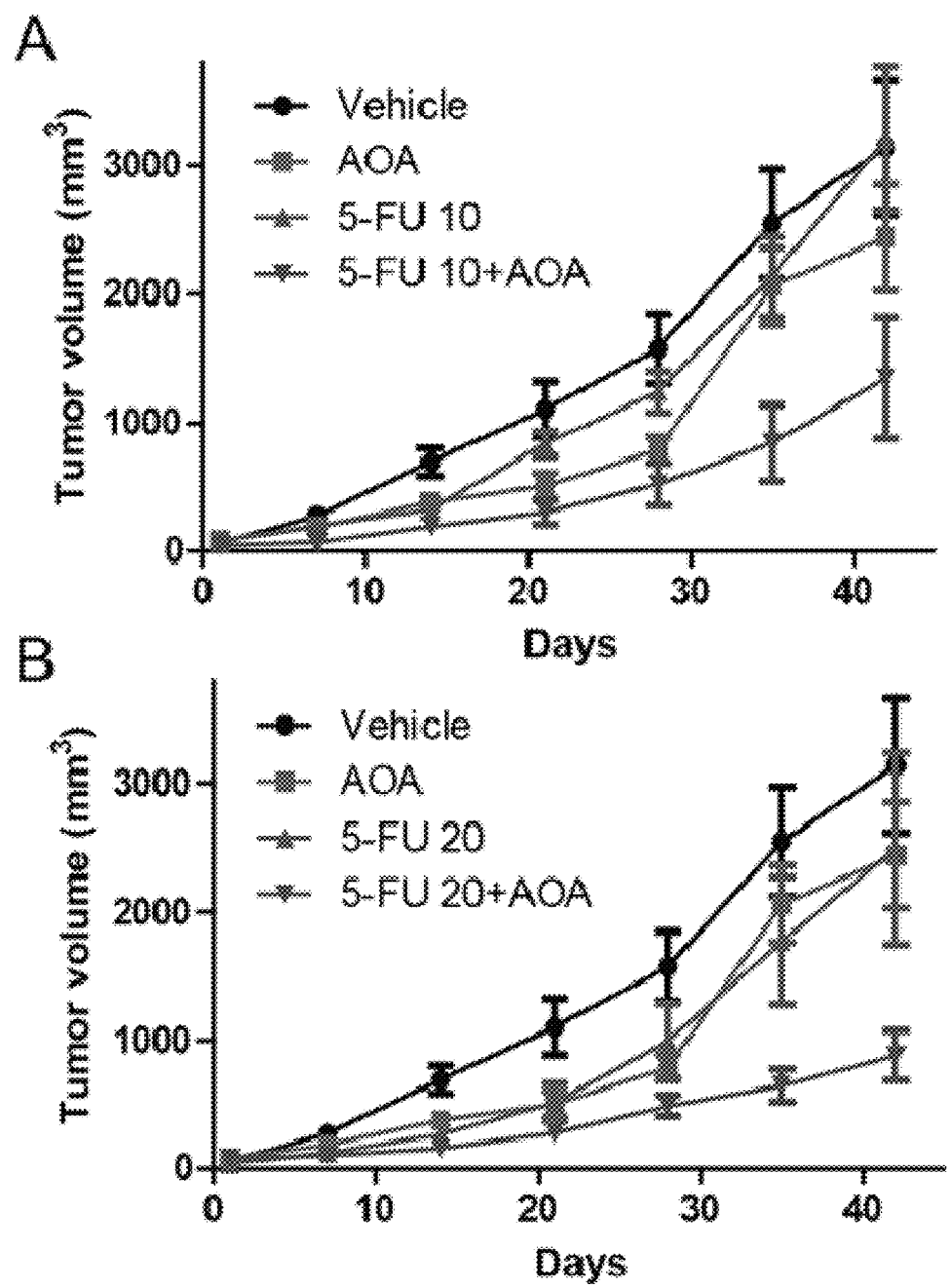
Figs. 10A-B

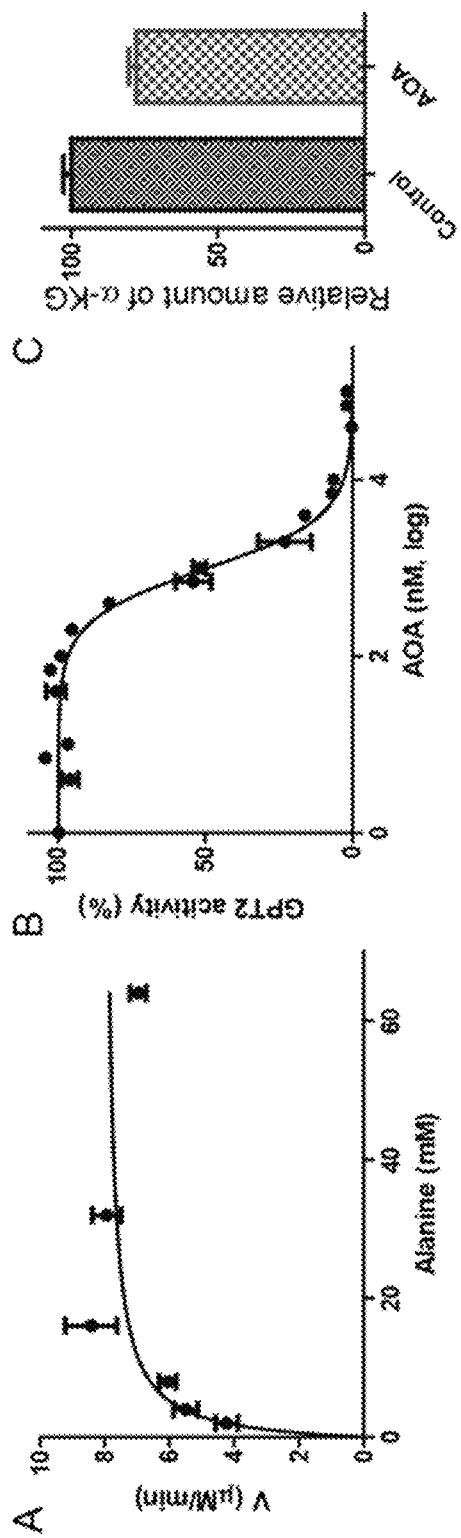
Figs. 11A-C

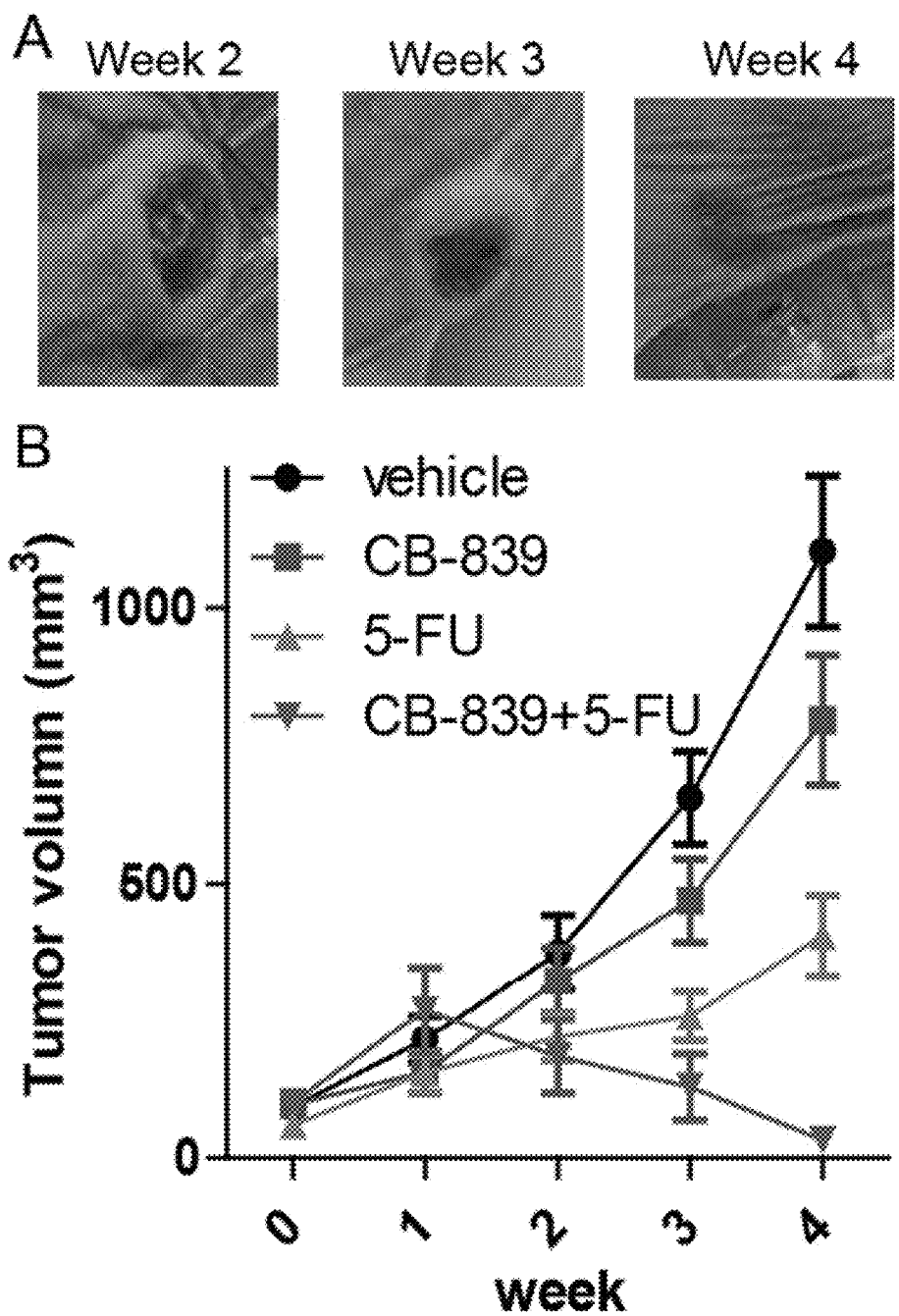
Figs. 12A-B

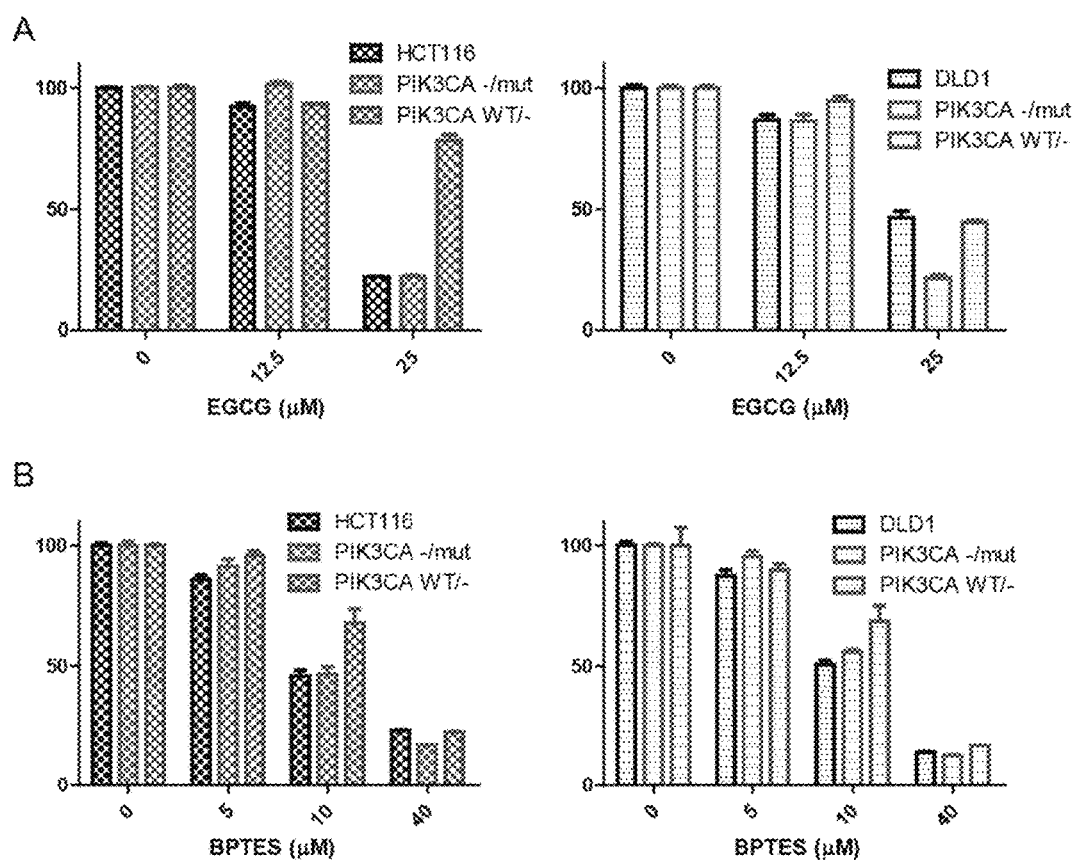
Figs. 13A-B

SEQUENCE LISTING

<160> NUMBER OF SEQ ID NOS: 818

<210> SEQ ID NO 1
<211> LENGTH: 17
<212> TYPE: DNA
<213> ORGANISM: Homo sapiens

<400> SEQUENCE: 1
tatatatatc catagtg                                                  17

<210> SEQ ID NO 2
<211> LENGTH: 17
<212> TYPE: DNA
<213> ORGANISM: Homo sapiens

<400> SEQUENCE: 2
tgactgaagc cttccag                                                  17

<210> SEQ ID NO 3
<211> LENGTH: 17
<212> TYPE: DNA
<213> ORGANISM: Homo sapiens

<400> SEQUENCE: 3
tgcctagacc aagaagt                                                  17

<210> SEQ ID NO 4
<211> LENGTH: 17
<212> TYPE: DNA
<213> ORGANISM: Homo sapiens

<400> SEQUENCE: 4 gtggcccgg ccgcacc                                                   17

<210> SEQ ID NO 5
<211> LENGTH: 17
<212> TYPE: DNA
<213> ORGANISM: Homo sapiens

<400> SEQUENCE: 5
tgtggtggtg tttttg                                                   17

<210> SEQ ID NO 6
<211> LENGTH: 17
<212> TYPE: DNA
<213> ORGANISM: Homo sapiens

```
<400> SEQUENCE: 6
gccagccagt ggcaagc                                            17

<210> SEQ ID NO 7
<211> LENGTH: 17
<212> TYPE: DNA
<213> ORGANISM: Homo sapiens

<400> SEQUENCE: 7
tttatttggc aaatttt                                            17

<210> SEQ ID NO 8
<211> LENGTH: 17
<212> TYPE: DNA
<213> ORGANISM: Homo sapiens

<400> SEQUENCE: 8
taaattcacc aaataaa                                            17

<210> SEQ ID NO 9
<211> LENGTH: 17
<212> TYPE: DNA
<213> ORGANISM: Homo sapiens

<400> SEQUENCE: 9
gggtgcttgg ttgtttc                                            17

<210> SEQ ID NO 10
<211> LENGTH: 17
<212> TYPE: DNA
<213> ORGANISM: Homo sapiens

<400> SEQUENCE: 10
tttagttggt atgtaaa                                            17

<210> SEQ ID NO 11
<211> LENGTH: 17
<212> TYPE: DNA
<213> ORGANISM: Homo sapiens

<400> SEQUENCE: 11
gccaccgtcc tgctgtc                                            17

<210> SEQ ID NO 12
<211> LENGTH: 17
<212> TYPE: DNA
<213> ORGANISM: Homo sapiens

<400> SEQUENCE: 12
ccttggtgcc ggtcaca                                            17

<210> SEQ ID NO 13
<211> LENGTH: 17
<212> TYPE: DNA
<213> ORGANISM: Homo sapiens

<400> SEQUENCE: 13
atggcctgta acagttg                                            17

<210> SEQ ID NO 14
<211> LENGTH: 17
<212> TYPE: DNA
```

```
<213> ORGANISM: Homo sapiens

<400> SEQUENCE: 14
gctttcttat tttgttt                                                    17

<210> SEQ ID NO 15
<211> LENGTH: 17
<212> TYPE: DNA
<213> ORGANISM: Homo sapiens

<400> SEQUENCE: 15
tattttggaa ttttcca                                                    17

<210> SEQ ID NO 16
<211> LENGTH: 17
<212> TYPE: DNA
<213> ORGANISM: Homo sapiens

<400> SEQUENCE: 16
ttatgcctcc attttca                                                    17

<210> SEQ ID NO 17
<211> LENGTH: 17
<212> TYPE: DNA
<213> ORGANISM: Homo sapiens

<400> SEQUENCE: 17
atgtccaatt ttgttgt                                                    17

<210> SEQ ID NO 18
<211> LENGTH: 17
<212> TYPE: DNA
<213> ORGANISM: Homo sapiens

<400> SEQUENCE: 18
ccaaggactc taggtca                                                    17

<210> SEQ ID NO 19
<211> LENGTH: 17
<212> TYPE: DNA
<213> ORGANISM: Homo sapiens

<400> SEQUENCE: 19
ttttaattgc ttgtaca                                                    17

<210> SEQ ID NO 20
<211> LENGTH: 17
<212> TYPE: DNA
<213> ORGANISM: Homo sapiens

<400> SEQUENCE: 20
cttcgacgaa ttaagga                                                    17

<210> SEQ ID NO 21
<211> LENGTH: 17
<212> TYPE: DNA
<213> ORGANISM: Homo sapiens

<400> SEQUENCE: 21
gggggttggt tctttgg                                                    17

<210> SEQ ID NO 22
<211> LENGTH: 17
```

```
<212> TYPE: DNA
<213> ORGANISM: Homo sapiens

<400> SEQUENCE: 22
gtgattcatt tgatgct                                                    17

<210> SEQ ID NO 23
<211> LENGTH: 17
<212> TYPE: DNA
<213> ORGANISM: Homo sapiens

<400> SEQUENCE: 23
agttggacgg accccag                                                    17

<210> SEQ ID NO 24
<211> LENGTH: 17
<212> TYPE: DNA
<213> ORGANISM: Homo sapiens

<400> SEQUENCE: 24
tgcgtcaccg tccactc                                                    17

<210> SEQ ID NO 25
<211> LENGTH: 17
<212> TYPE: DNA
<213> ORGANISM: Homo sapiens

<400> SEQUENCE: 25
tataaaattt aaaaaaa                                                    17

<210> SEQ ID NO 26
<211> LENGTH: 17
<212> TYPE: DNA
<213> ORGANISM: Homo sapiens

<400> SEQUENCE: 26
gcaaagaaaa aaaaaag                                                    17

<210> SEQ ID NO 27
<211> LENGTH: 17
<212> TYPE: DNA
<213> ORGANISM: Homo sapiens

<400> SEQUENCE: 27
gagggccgtg tagccat                                                    17

<210> SEQ ID NO 28
<211> LENGTH: 17
<212> TYPE: DNA
<213> ORGANISM: Homo sapiens

<400> SEQUENCE: 28
gaatgatttc tctgcta                                                    17

<210> SEQ ID NO 29
<211> LENGTH: 17
<212> TYPE: DNA
<213> ORGANISM: Homo sapiens

<400> SEQUENCE: 29
cagatttctg tatgttc                                                    17

<210> SEQ ID NO 30
```

```
<211> LENGTH: 17
<212> TYPE: DNA
<213> ORGANISM: Homo sapiens

<400> SEQUENCE: 30
gatccaaatg tttgttg                                                    17

<210> SEQ ID NO 31
<211> LENGTH: 17
<212> TYPE: DNA
<213> ORGANISM: Homo sapiens

<400> SEQUENCE: 31
cagtcaggct ggcagtg                                                    17

<210> SEQ ID NO 32
<211> LENGTH: 17
<212> TYPE: DNA
<213> ORGANISM: Homo sapiens

<400> SEQUENCE: 32
tgaccggcga gcgcggg                                                    17

<210> SEQ ID NO 33
<211> LENGTH: 17
<212> TYPE: DNA
<213> ORGANISM: Homo sapiens

<400> SEQUENCE: 33
gtgctggtcc ctccctt                                                    17

<210> SEQ ID NO 34
<211> LENGTH: 17
<212> TYPE: DNA
<213> ORGANISM: Homo sapiens

<400> SEQUENCE: 34
gtatatcatt tcctctt                                                    17

<210> SEQ ID NO 35
<211> LENGTH: 17
<212> TYPE: DNA
<213> ORGANISM: Homo sapiens

<400> SEQUENCE: 35
tatgcttagt ataaatg                                                    17

<210> SEQ ID NO 36
<211> LENGTH: 17
<212> TYPE: DNA
<213> ORGANISM: Homo sapiens

<400> SEQUENCE: 36
gtgggtgtcc tggggcc                                                    17

<210> SEQ ID NO 37
<211> LENGTH: 17
<212> TYPE: DNA
<213> ORGANISM: Homo sapiens

<400> SEQUENCE: 37
tgcgcgccct gccggcg                                                    17
```

```
<210> SEQ ID NO 38
<211> LENGTH: 17
<212> TYPE: DNA
<213> ORGANISM: Homo sapiens

<400> SEQUENCE: 38
tttgttaaaa caaaaaa                                                   17

<210> SEQ ID NO 39
<211> LENGTH: 17
<212> TYPE: DNA
<213> ORGANISM: Homo sapiens

<400> SEQUENCE: 39
ttcaaggaac aggaaaa                                                   17

<210> SEQ ID NO 40
<211> LENGTH: 17
<212> TYPE: DNA
<213> ORGANISM: Homo sapiens

<400> SEQUENCE: 40
gtttccaaaa aatggta                                                   17

<210> SEQ ID NO 41
<211> LENGTH: 17
<212> TYPE: DNA
<213> ORGANISM: Homo sapiens

<400> SEQUENCE: 41
tcaaaaaaaa aaaaaaa                                                   17

<210> SEQ ID NO 42
<211> LENGTH: 17
<212> TYPE: DNA
<213> ORGANISM: Homo sapiens

<400> SEQUENCE: 42
ggggtccttc agccagc                                                   17

<210> SEQ ID NO 43
<211> LENGTH: 17
<212> TYPE: DNA
<213> ORGANISM: Homo sapiens

<400> SEQUENCE: 43
cctgtaatcc caacact                                                   17

<210> SEQ ID NO 44
<211> LENGTH: 17
<212> TYPE: DNA
<213> ORGANISM: Homo sapiens

<400> SEQUENCE: 44
agcacaagac ttgtagt                                                   17

<210> SEQ ID NO 45
<211> LENGTH: 17
<212> TYPE: DNA
<213> ORGANISM: Homo sapiens

<400> SEQUENCE: 45
actctgccaa gcatcca                                                   17
```

```
<210> SEQ ID NO 46
<211> LENGTH: 17
<212> TYPE: DNA
<213> ORGANISM: Homo sapiens

<400> SEQUENCE: 46
caaactgctt tattttc                                                  17

<210> SEQ ID NO 47
<211> LENGTH: 17
<212> TYPE: DNA
<213> ORGANISM: Homo sapiens

<400> SEQUENCE: 47
tatcgttgcc tctgcac                                                  17

<210> SEQ ID NO 48
<211> LENGTH: 17
<212> TYPE: DNA
<213> ORGANISM: Homo sapiens

<400> SEQUENCE: 48
agagtttgag gcttcag                                                  17

<210> SEQ ID NO 49
<211> LENGTH: 17
<212> TYPE: DNA
<213> ORGANISM: Homo sapiens

<400> SEQUENCE: 49
tgtgagttat tatcact                                                  17

<210> SEQ ID NO 50
<211> LENGTH: 17
<212> TYPE: DNA
<213> ORGANISM: Homo sapiens

<400> SEQUENCE: 50
gtcatatttc ctgagta                                                  17

<210> SEQ ID NO 51
<211> LENGTH: 17
<212> TYPE: DNA
<213> ORGANISM: Homo sapiens

<400> SEQUENCE: 51
tcagatagga caacact                                                  17

<210> SEQ ID NO 52
<211> LENGTH: 17
<212> TYPE: DNA
<213> ORGANISM: Homo sapiens

<400> SEQUENCE: 52
atgttcaatt ttatctt                                                  17

<210> SEQ ID NO 53
<211> LENGTH: 17
<212> TYPE: DNA
<213> ORGANISM: Homo sapiens

<400> SEQUENCE: 53
cctggctaat ttttgta                                                  17
```

<210> SEQ ID NO 54
<211> LENGTH: 17
<212> TYPE: DNA
<213> ORGANISM: Homo sapiens

<400> SEQUENCE: 54
gtgaatctat ctctccg                                               17

<210> SEQ ID NO 55
<211> LENGTH: 17
<212> TYPE: DNA
<213> ORGANISM: Homo sapiens

<400> SEQUENCE: 55
cagtgtatat attgaga                                               17

<210> SEQ ID NO 56
<211> LENGTH: 17
<212> TYPE: DNA
<213> ORGANISM: Homo sapiens

<400> SEQUENCE: 56
ggcctatgag cggtcta                                               17

<210> SEQ ID NO 57
<211> LENGTH: 17
<212> TYPE: DNA
<213> ORGANISM: Homo sapiens

<400> SEQUENCE: 57
tatataagta ctgacca                                               17

<210> SEQ ID NO 58
<211> LENGTH: 17
<212> TYPE: DNA
<213> ORGANISM: Homo sapiens

<400> SEQUENCE: 58
ggtgtctgtg ggttatt                                               17

<210> SEQ ID NO 59
<211> LENGTH: 17
<212> TYPE: DNA
<213> ORGANISM: Homo sapiens

<400> SEQUENCE: 59
acttgataaa ttaagta                                               17

<210> SEQ ID NO 60
<211> LENGTH: 17
<212> TYPE: DNA
<213> ORGANISM: Homo sapiens

<400> SEQUENCE: 60
acataaataa aaaaata                                               17

<210> SEQ ID NO 61
<211> LENGTH: 17
<212> TYPE: DNA
<213> ORGANISM: Homo sapiens

<400> SEQUENCE: 61

```
acttacctgt aatggga                                                    17

<210> SEQ ID NO 62
<211> LENGTH: 17
<212> TYPE: DNA
<213> ORGANISM: Homo sapiens

<400> SEQUENCE: 62
cgctgaatga tgtcacg                                                    17

<210> SEQ ID NO 63
<211> LENGTH: 17
<212> TYPE: DNA
<213> ORGANISM: Homo sapiens

<400> SEQUENCE: 63
cctgtctagc tcataca                                                    17

<210> SEQ ID NO 64
<211> LENGTH: 17
<212> TYPE: DNA
<213> ORGANISM: Homo sapiens

<400> SEQUENCE: 64
taacctcagg tatcttc                                                    17

<210> SEQ ID NO 65
<211> LENGTH: 17
<212> TYPE: DNA
<213> ORGANISM: Homo sapiens

<400> SEQUENCE: 65
ctctgttacc tggtgaa                                                    17

<210> SEQ ID NO 66
<211> LENGTH: 17
<212> TYPE: DNA
<213> ORGANISM: Homo sapiens

<400> SEQUENCE: 66
ctctcctgct caaggca                                                    17

<210> SEQ ID NO 67
<211> LENGTH: 17
<212> TYPE: DNA
<213> ORGANISM: Homo sapiens

<400> SEQUENCE: 67
tggatgtact tatgacc                                                    17

<210> SEQ ID NO 68
<211> LENGTH: 17
<212> TYPE: DNA
<213> ORGANISM: Homo sapiens

<400> SEQUENCE: 68
tgcacgttct ctgttta                                                    17

<210> SEQ ID NO 69
<211> LENGTH: 17
<212> TYPE: DNA
<213> ORGANISM: Homo sapiens

<400> SEQUENCE: 69
```
gaaaactgtt tattttt                                                    17

<210> SEQ ID NO 70
<211> LENGTH: 17
<212> TYPE: DNA
<213> ORGANISM: Homo sapiens

<400> SEQUENCE: 70
aattatgact tctcatt                                                    17

<210> SEQ ID NO 71
<211> LENGTH: 17
<212> TYPE: DNA
<213> ORGANISM: Homo sapiens

<400> SEQUENCE: 71
ctccaggagg atgagct                                                    17

<210> SEQ ID NO 72
<211> LENGTH: 17
<212> TYPE: DNA
<213> ORGANISM: Homo sapiens

<400> SEQUENCE: 72
cagtcggtca agaggag                                                    17

<210> SEQ ID NO 73
<211> LENGTH: 17
<212> TYPE: DNA
<213> ORGANISM: Homo sapiens

<400> SEQUENCE: 73
catttcagag actttaa                                                    17

<210> SEQ ID NO 74
<211> LENGTH: 17
<212> TYPE: DNA
<213> ORGANISM: Homo sapiens

<400> SEQUENCE: 74
aacctcgagt tctgact                                                    17

<210> SEQ ID NO 75
<211> LENGTH: 17
<212> TYPE: DNA
<213> ORGANISM: Homo sapiens

<400> SEQUENCE: 75
taacagttgt gtcataa                                                    17

<210> SEQ ID NO 76
<211> LENGTH: 17
<212> TYPE: DNA
<213> ORGANISM: Homo sapiens

<400> SEQUENCE: 76
gcccagggcc gctggga                                                    17

<210> SEQ ID NO 77
<211> LENGTH: 17
<212> TYPE: DNA
<213> ORGANISM: Homo sapiens

```
<400> SEQUENCE: 77
aaagaaaccc tgcggat                                                    17

<210> SEQ ID NO 78
<211> LENGTH: 17
<212> TYPE: DNA
<213> ORGANISM: Homo sapiens

<400> SEQUENCE: 78
cacctagcat agtgctt                                                    17

<210> SEQ ID NO 79
<211> LENGTH: 17
<212> TYPE: DNA
<213> ORGANISM: Homo sapiens

<400> SEQUENCE: 79
aggctaaaag caaagtc                                                    17

<210> SEQ ID NO 80
<211> LENGTH: 17
<212> TYPE: DNA
<213> ORGANISM: Homo sapiens

<400> SEQUENCE: 80
gtgatgggct ccctccc                                                    17

<210> SEQ ID NO 81
<211> LENGTH: 17
<212> TYPE: DNA
<213> ORGANISM: Homo sapiens

<400> SEQUENCE: 81
gctacacaca cccttgc                                                    17

<210> SEQ ID NO 82
<211> LENGTH: 17
<212> TYPE: DNA
<213> ORGANISM: Homo sapiens

<400> SEQUENCE: 82
aataaagtca ttactag                                                    17

<210> SEQ ID NO 83
<211> LENGTH: 17
<212> TYPE: DNA
<213> ORGANISM: Homo sapiens

<400> SEQUENCE: 83
taatcaggag aaaggga                                                    17

<210> SEQ ID NO 84
<211> LENGTH: 17
<212> TYPE: DNA
<213> ORGANISM: Homo sapiens

<400> SEQUENCE: 84
tgtgacactg attcttt                                                    17

<210> SEQ ID NO 85
<211> LENGTH: 17
<212> TYPE: DNA
<213> ORGANISM: Homo sapiens
```

```
<400> SEQUENCE: 85
tgaatgattt tctcaaa                                                        17

<210> SEQ ID NO 86
<211> LENGTH: 17
<212> TYPE: DNA
<213> ORGANISM: Homo sapiens

<400> SEQUENCE: 86
gccccagcga ggggctg                                                        17

<210> SEQ ID NO 87
<211> LENGTH: 17
<212> TYPE: DNA
<213> ORGANISM: Homo sapiens

<400> SEQUENCE: 87
ttaaataaaa ccatttt                                                        17

<210> SEQ ID NO 88
<211> LENGTH: 17
<212> TYPE: DNA
<213> ORGANISM: Homo sapiens

<400> SEQUENCE: 88
gaaataaaat tacttat                                                        17

<210> SEQ ID NO 89
<211> LENGTH: 17
<212> TYPE: DNA
<213> ORGANISM: Homo sapiens

<400> SEQUENCE: 89
atctgtgaaa taaagcc                                                        17

<210> SEQ ID NO 90
<211> LENGTH: 17
<212> TYPE: DNA
<213> ORGANISM: Homo sapiens

<400> SEQUENCE: 90
ctatgcatca gactggc                                                        17

<210> SEQ ID NO 91
<211> LENGTH: 17
<212> TYPE: DNA
<213> ORGANISM: Homo sapiens

<400> SEQUENCE: 91
tggcttaaat gattttt                                                        17

<210> SEQ ID NO 92
<211> LENGTH: 17
<212> TYPE: DNA
<213> ORGANISM: Homo sapiens

<400> SEQUENCE: 92
ctgcttcagc agtgacg                                                        17

<210> SEQ ID NO 93
<211> LENGTH: 17
<212> TYPE: DNA
```

```
<213> ORGANISM: Homo sapiens

<400> SEQUENCE: 93
tctactcagc atttgat                                                   17

<210> SEQ ID NO 94
<211> LENGTH: 17
<212> TYPE: DNA
<213> ORGANISM: Homo sapiens

<400> SEQUENCE: 94
agaccaggca agaaggt                                                   17

<210> SEQ ID NO 95
<211> LENGTH: 17
<212> TYPE: DNA
<213> ORGANISM: Homo sapiens

<400> SEQUENCE: 95
tctgcctatg cactgaa                                                   17

<210> SEQ ID NO 96
<211> LENGTH: 17
<212> TYPE: DNA
<213> ORGANISM: Homo sapiens

<400> SEQUENCE: 96
ggggtcccaa acagtca                                                   17

<210> SEQ ID NO 97
<211> LENGTH: 17
<212> TYPE: DNA
<213> ORGANISM: Homo sapiens

<400> SEQUENCE: 97
tgagtggtca ctttatt                                                   17

<210> SEQ ID NO 98
<211> LENGTH: 17
<212> TYPE: DNA
<213> ORGANISM: Homo sapiens

<400> SEQUENCE: 98
ccccagaccg gcccacc                                                   17

<210> SEQ ID NO 99
<211> LENGTH: 17
<212> TYPE: DNA
<213> ORGANISM: Homo sapiens

<400> SEQUENCE: 99 tcctttttg tggactt                                                    17

<210> SEQ ID NO 100
<211> LENGTH: 17
<212> TYPE: DNA
<213> ORGANISM: Homo sapiens

<400> SEQUENCE: 100
ttgccgctgc tgtttct                                                   17

<210> SEQ ID NO 101
<211> LENGTH: 17
```

```
<212> TYPE: DNA
<213> ORGANISM: Homo sapiens

<400> SEQUENCE: 101
gtgggccttt gaggttc                                                 17

<210> SEQ ID NO 102
<211> LENGTH: 17
<212> TYPE: DNA
<213> ORGANISM: Homo sapiens

<400> SEQUENCE: 102
acatcttgct tataaat                                                 17

<210> SEQ ID NO 103
<211> LENGTH: 17
<212> TYPE: DNA
<213> ORGANISM: Homo sapiens

<400> SEQUENCE: 103
aacaagtctt tctaatg                                                 17

<210> SEQ ID NO 104
<211> LENGTH: 17
<212> TYPE: DNA
<213> ORGANISM: Homo sapiens

<400> SEQUENCE: 104
gtacccgtac agcgttg                                                 17

<210> SEQ ID NO 105
<211> LENGTH: 17
<212> TYPE: DNA
<213> ORGANISM: Homo sapiens

<400> SEQUENCE: 105
acctccacca aagccca                                                 17

<210> SEQ ID NO 106
<211> LENGTH: 17
<212> TYPE: DNA
<213> ORGANISM: Homo sapiens

<400> SEQUENCE: 106
tgtctggttg tttgaaa                                                 17

<210> SEQ ID NO 107
<211> LENGTH: 17
<212> TYPE: DNA
<213> ORGANISM: Homo sapiens

<400> SEQUENCE: 107
gcaggcggct ctggctt                                                 17

<210> SEQ ID NO 108
<211> LENGTH: 17
<212> TYPE: DNA
<213> ORGANISM: Homo sapiens

<400> SEQUENCE: 108
caataaaaca aactcta                                                 17

<210> SEQ ID NO 109
```

```
<211> LENGTH: 17
<212> TYPE: DNA
<213> ORGANISM: Homo sapiens

<400> SEQUENCE: 109
gtatcttaat aaagaat                                                  17

<210> SEQ ID NO 110
<211> LENGTH: 17
<212> TYPE: DNA
<213> ORGANISM: Homo sapiens

<400> SEQUENCE: 110
tgaacacccg tgtctgg                                                  17

<210> SEQ ID NO 111
<211> LENGTH: 17
<212> TYPE: DNA
<213> ORGANISM: Homo sapiens

<400> SEQUENCE: 111
atttatccat aaaggag                                                  17

<210> SEQ ID NO 112
<211> LENGTH: 17
<212> TYPE: DNA
<213> ORGANISM: Homo sapiens

<400> SEQUENCE: 112
acattcttgt ttttaat                                                  17

<210> SEQ ID NO 113
<211> LENGTH: 17
<212> TYPE: DNA
<213> ORGANISM: Homo sapiens

<400> SEQUENCE: 113
ggactggccc aggcaca                                                  17

<210> SEQ ID NO 114
<211> LENGTH: 17
<212> TYPE: DNA
<213> ORGANISM: Homo sapiens

<400> SEQUENCE: 114
gatagaggga ctgaggg                                                  17

<210> SEQ ID NO 115
<211> LENGTH: 17
<212> TYPE: DNA
<213> ORGANISM: Homo sapiens

<400> SEQUENCE: 115
gggggcaggt cccccag                                                  17

<210> SEQ ID NO 116
<211> LENGTH: 17
<212> TYPE: DNA
<213> ORGANISM: Homo sapiens

<400> SEQUENCE: 116
gggttccccg gcagggg                                                  17
```

```
<210> SEQ ID NO 117
<211> LENGTH: 17
<212> TYPE: DNA
<213> ORGANISM: Homo sapiens

<400> SEQUENCE: 117
ccctcgcatt gcttccc                                                  17

<210> SEQ ID NO 118
<211> LENGTH: 17
<212> TYPE: DNA
<213> ORGANISM: Homo sapiens

<400> SEQUENCE: 118
ttattttcct gtgtcat                                                  17

<210> SEQ ID NO 119
<211> LENGTH: 17
<212> TYPE: DNA
<213> ORGANISM: Homo sapiens

<400> SEQUENCE: 119
ggcaggcggg tgggggg                                                  17

<210> SEQ ID NO 120
<211> LENGTH: 17
<212> TYPE: DNA
<213> ORGANISM: Homo sapiens

<400> SEQUENCE: 120
gggcaagcca gggccca                                                  17

<210> SEQ ID NO 121
<211> LENGTH: 17
<212> TYPE: DNA
<213> ORGANISM: Homo sapiens

<400> SEQUENCE: 121
ggccctggtg tttgcac                                                  17

<210> SEQ ID NO 122
<211> LENGTH: 17
<212> TYPE: DNA
<213> ORGANISM: Homo sapiens

<400> SEQUENCE: 122
gtggcgggag cctgttg                                                  17

<210> SEQ ID NO 123
<211> LENGTH: 17
<212> TYPE: DNA
<213> ORGANISM: Homo sapiens

<400> SEQUENCE: 123
gtgccatatt tagctac                                                  17

<210> SEQ ID NO 124
<211> LENGTH: 17
<212> TYPE: DNA
<213> ORGANISM: Homo sapiens

<400> SEQUENCE: 124 gccccctgcgc aaggatg                                                 17
```

```
<210> SEQ ID NO 125
<211> LENGTH: 17
<212> TYPE: DNA
<213> ORGANISM: Homo sapiens

<400> SEQUENCE: 125
ggaagagggt gagctga                                              17

<210> SEQ ID NO 126
<211> LENGTH: 17
<212> TYPE: DNA
<213> ORGANISM: Homo sapiens

<400> SEQUENCE: 126
accataatgt gtttaaa                                              17

<210> SEQ ID NO 127
<211> LENGTH: 17
<212> TYPE: DNA
<213> ORGANISM: Homo sapiens

<400> SEQUENCE: 127
acccaatttg tgttatt                                              17

<210> SEQ ID NO 128
<211> LENGTH: 17
<212> TYPE: DNA
<213> ORGANISM: Homo sapiens

<400> SEQUENCE: 128
cgcgcacccg ccgaccc                                              17

<210> SEQ ID NO 129
<211> LENGTH: 17
<212> TYPE: DNA
<213> ORGANISM: Homo sapiens

<400> SEQUENCE: 129
tcctgaaata aatattg                                              17

<210> SEQ ID NO 130
<211> LENGTH: 17
<212> TYPE: DNA
<213> ORGANISM: Homo sapiens

<400> SEQUENCE: 130
gagttactga aggtctc                                              17

<210> SEQ ID NO 131
<211> LENGTH: 17
<212> TYPE: DNA
<213> ORGANISM: Homo sapiens

<400> SEQUENCE: 131
gcgtgtgctc gcccact                                              17

<210> SEQ ID NO 132
<211> LENGTH: 17
<212> TYPE: DNA
<213> ORGANISM: Homo sapiens

<400> SEQUENCE: 132
aagaagcaag acgaaaa                                              17
```

```
<210> SEQ ID NO 133
<211> LENGTH: 17
<212> TYPE: DNA
<213> ORGANISM: Homo sapiens

<400> SEQUENCE: 133
agagacaagt ctcttag                                                  17

<210> SEQ ID NO 134
<211> LENGTH: 17
<212> TYPE: DNA
<213> ORGANISM: Homo sapiens

<400> SEQUENCE: 134
tgatgtccac cagtgga                                                  17

<210> SEQ ID NO 135
<211> LENGTH: 17
<212> TYPE: DNA
<213> ORGANISM: Homo sapiens

<400> SEQUENCE: 135
tccctgggca gcttcag                                                  17

<210> SEQ ID NO 136
<211> LENGTH: 17
<212> TYPE: DNA
<213> ORGANISM: Homo sapiens

<400> SEQUENCE: 136
taaattacca gtaaagt                                                  17

<210> SEQ ID NO 137
<211> LENGTH: 17
<212> TYPE: DNA
<213> ORGANISM: Homo sapiens

<400> SEQUENCE: 137
cctgacgctc cagcgcc                                                  17

<210> SEQ ID NO 138
<211> LENGTH: 17
<212> TYPE: DNA
<213> ORGANISM: Homo sapiens

<400> SEQUENCE: 138
ggcctctcaa ggctggc                                                  17

<210> SEQ ID NO 139
<211> LENGTH: 17
<212> TYPE: DNA
<213> ORGANISM: Homo sapiens

<400> SEQUENCE: 139
gactcaggga tttgttg                                                  17

<210> SEQ ID NO 140
<211> LENGTH: 17
<212> TYPE: DNA
<213> ORGANISM: Homo sapiens

<400> SEQUENCE: 140
```

```
ggggacggga ggagggg                                                  17

<210> SEQ ID NO 141
<211> LENGTH: 17
<212> TYPE: DNA
<213> ORGANISM: Homo sapiens

<400> SEQUENCE: 141
gtaaaaaagc ctgaaac                                                  17

<210> SEQ ID NO 142
<211> LENGTH: 17
<212> TYPE: DNA
<213> ORGANISM: Homo sapiens

<400> SEQUENCE: 142
tactaaaaaa ggagaaa                                                  17

<210> SEQ ID NO 143
<211> LENGTH: 17
<212> TYPE: DNA
<213> ORGANISM: Homo sapiens

<400> SEQUENCE: 143
tgccttgaaa gggggca                                                  17

<210> SEQ ID NO 144
<211> LENGTH: 17
<212> TYPE: DNA
<213> ORGANISM: Homo sapiens

<400> SEQUENCE: 144
ccaggaacaa tgtctcc                                                  17

<210> SEQ ID NO 145
<211> LENGTH: 17
<212> TYPE: DNA
<213> ORGANISM: Homo sapiens

<400> SEQUENCE: 145
tttgctgaac accttgt                                                  17

<210> SEQ ID NO 146
<211> LENGTH: 17
<212> TYPE: DNA
<213> ORGANISM: Homo sapiens

<400> SEQUENCE: 146
gtttgcggag gttagat                                                  17

<210> SEQ ID NO 147
<211> LENGTH: 17
<212> TYPE: DNA
<213> ORGANISM: Homo sapiens

<400> SEQUENCE: 147
ttgaactggc ctctttt                                                  17

<210> SEQ ID NO 148
<211> LENGTH: 17
<212> TYPE: DNA
<213> ORGANISM: Homo sapiens

<400> SEQUENCE: 148
```
tagcaaagat tttcaaa  17

<210> SEQ ID NO 149
<211> LENGTH: 17
<212> TYPE: DNA
<213> ORGANISM: Homo sapiens

<400> SEQUENCE: 149
tttcaatacc tacaaac  17

<210> SEQ ID NO 150
<211> LENGTH: 17
<212> TYPE: DNA
<213> ORGANISM: Homo sapiens

<400> SEQUENCE: 150
tgatttctgt acataag  17

<210> SEQ ID NO 151
<211> LENGTH: 17
<212> TYPE: DNA
<213> ORGANISM: Homo sapiens

<400> SEQUENCE: 151
tattttcttt gtaaagt  17

<210> SEQ ID NO 152
<211> LENGTH: 17
<212> TYPE: DNA
<213> ORGANISM: Homo sapiens

<400> SEQUENCE: 152
taccgggaat accggga  17

<210> SEQ ID NO 153
<211> LENGTH: 17
<212> TYPE: DNA
<213> ORGANISM: Homo sapiens

<400> SEQUENCE: 153
ggctagtact tggggtt  17

<210> SEQ ID NO 154
<211> LENGTH: 17
<212> TYPE: DNA
<213> ORGANISM: Homo sapiens

<400> SEQUENCE: 154
gtggtgggtg cctgtaa  17

<210> SEQ ID NO 155
<211> LENGTH: 17
<212> TYPE: DNA
<213> ORGANISM: Homo sapiens

<400> SEQUENCE: 155
tactttctcc tttctgg  17

<210> SEQ ID NO 156
<211> LENGTH: 17
<212> TYPE: DNA
<213> ORGANISM: Homo sapiens

```
<400> SEQUENCE: 156
tgaggaggtt gcgcgct                                              17

<210> SEQ ID NO 157
<211> LENGTH: 17
<212> TYPE: DNA
<213> ORGANISM: Homo sapiens

<400> SEQUENCE: 157
tgccaccacg cccagct                                              17

<210> SEQ ID NO 158
<211> LENGTH: 17
<212> TYPE: DNA
<213> ORGANISM: Homo sapiens

<400> SEQUENCE: 158
taaaatcaaa atataag                                              17

<210> SEQ ID NO 159
<211> LENGTH: 17
<212> TYPE: DNA
<213> ORGANISM: Homo sapiens

<400> SEQUENCE: 159
cactacggga gctaggg                                              17

<210> SEQ ID NO 160
<211> LENGTH: 17
<212> TYPE: DNA
<213> ORGANISM: Homo sapiens

<400> SEQUENCE: 160
gtaattattg gaaagta                                              17

<210> SEQ ID NO 161
<211> LENGTH: 17
<212> TYPE: DNA
<213> ORGANISM: Homo sapiens

<400> SEQUENCE: 161
ttaaatcgtg acagaat                                              17

<210> SEQ ID NO 162
<211> LENGTH: 17
<212> TYPE: DNA
<213> ORGANISM: Homo sapiens

<400> SEQUENCE: 162
gctcgtggtc aaaaaag                                              17

<210> SEQ ID NO 163
<211> LENGTH: 17
<212> TYPE: DNA
<213> ORGANISM: Homo sapiens

<400> SEQUENCE: 163
agcagcagag tcgagtg                                              17

<210> SEQ ID NO 164
<211> LENGTH: 17
<212> TYPE: DNA
<213> ORGANISM: Homo sapiens
```

<400> SEQUENCE: 164
agggacttgt gtgacct                                                  17

<210> SEQ ID NO 165
<211> LENGTH: 17
<212> TYPE: DNA
<213> ORGANISM: Homo sapiens

<400> SEQUENCE: 165
attcaaattc ttcaaag                                                  17

<210> SEQ ID NO 166
<211> LENGTH: 17
<212> TYPE: DNA
<213> ORGANISM: Homo sapiens

<400> SEQUENCE: 166
ttccctcgtg atcccaa                                                  17

<210> SEQ ID NO 167
<211> LENGTH: 17
<212> TYPE: DNA
<213> ORGANISM: Homo sapiens

<400> SEQUENCE: 167
tttgttaaaa aaaaaaa                                                  17

<210> SEQ ID NO 168
<211> LENGTH: 17
<212> TYPE: DNA
<213> ORGANISM: Homo sapiens

<400> SEQUENCE: 168
tgggcaatat cccagtt                                                  17

<210> SEQ ID NO 169
<211> LENGTH: 17
<212> TYPE: DNA
<213> ORGANISM: Homo sapiens

<400> SEQUENCE: 169
tagttgttta gttataa                                                  17

<210> SEQ ID NO 170
<211> LENGTH: 17
<212> TYPE: DNA
<213> ORGANISM: Homo sapiens

<400> SEQUENCE: 170
gtttttattc acttgaa                                                  17

<210> SEQ ID NO 171
<211> LENGTH: 17
<212> TYPE: DNA
<213> ORGANISM: Homo sapiens

<400> SEQUENCE: 171
ttcaactttt tattgtg                                                  17

<210> SEQ ID NO 172
<211> LENGTH: 17
<212> TYPE: DNA

```
<213> ORGANISM: Homo sapiens

<400> SEQUENCE: 172
caataaaact gattgtc                                                    17

<210> SEQ ID NO 173
<211> LENGTH: 17
<212> TYPE: DNA
<213> ORGANISM: Homo sapiens

<400> SEQUENCE: 173
ggagagtaac atcacag                                                    17

<210> SEQ ID NO 174
<211> LENGTH: 17
<212> TYPE: DNA
<213> ORGANISM: Homo sapiens

<400> SEQUENCE: 174
gcataattac ttggtag                                                    17

<210> SEQ ID NO 175
<211> LENGTH: 17
<212> TYPE: DNA
<213> ORGANISM: Homo sapiens

<400> SEQUENCE: 175
gcacaagaga aaccagc                                                    17

<210> SEQ ID NO 176
<211> LENGTH: 17
<212> TYPE: DNA
<213> ORGANISM: Homo sapiens

<400> SEQUENCE: 176
tattccccac ctgtgtt                                                    17

<210> SEQ ID NO 177
<211> LENGTH: 17
<212> TYPE: DNA
<213> ORGANISM: Homo sapiens

<400> SEQUENCE: 177
gccttccgtg tccccac                                                    17

<210> SEQ ID NO 178
<211> LENGTH: 17
<212> TYPE: DNA
<213> ORGANISM: Homo sapiens

<400> SEQUENCE: 178
tgctgaggaa gcacgtg                                                    17

<210> SEQ ID NO 179
<211> LENGTH: 17
<212> TYPE: DNA
<213> ORGANISM: Homo sapiens

<400> SEQUENCE: 179
cccaaagaca tccagtt                                                    17

<210> SEQ ID NO 180
<211> LENGTH: 17
```

<212> TYPE: DNA
<213> ORGANISM: Homo sapiens

<400> SEQUENCE: 180
ttctaaactg tttttc                                                    17

<210> SEQ ID NO 181
<211> LENGTH: 17
<212> TYPE: DNA
<213> ORGANISM: Homo sapiens

<400> SEQUENCE: 181
aggccgtccc cgaaggc                                                   17

<210> SEQ ID NO 182
<211> LENGTH: 17
<212> TYPE: DNA
<213> ORGANISM: Homo sapiens

<400> SEQUENCE: 182
ccacctccca taccacc                                                   17

<210> SEQ ID NO 183
<211> LENGTH: 17
<212> TYPE: DNA
<213> ORGANISM: Homo sapiens

<400> SEQUENCE: 183
gacaaataca tccacaa                                                   17

<210> SEQ ID NO 184
<211> LENGTH: 17
<212> TYPE: DNA
<213> ORGANISM: Homo sapiens

<400> SEQUENCE: 184
ggcaagtgca aggtgta                                                   17

<210> SEQ ID NO 185
<211> LENGTH: 17
<212> TYPE: DNA
<213> ORGANISM: Homo sapiens

<400> SEQUENCE: 185
tttcaaagat acagtat                                                   17

<210> SEQ ID NO 186
<211> LENGTH: 17
<212> TYPE: DNA
<213> ORGANISM: Homo sapiens

<400> SEQUENCE: 186
ggtccagcat caggcct                                                   17

<210> SEQ ID NO 187
<211> LENGTH: 17
<212> TYPE: DNA
<213> ORGANISM: Homo sapiens

<400> SEQUENCE: 187
caccatcaaa aaaaaaa                                                   17

<210> SEQ ID NO 188

```
<211> LENGTH: 17
<212> TYPE: DNA
<213> ORGANISM: Homo sapiens

<400> SEQUENCE: 188
tactgcattg ttactttt                                                 17

<210> SEQ ID NO 189
<211> LENGTH: 17
<212> TYPE: DNA
<213> ORGANISM: Homo sapiens

<400> SEQUENCE: 189
ttgttgaagc aaatgaa                                                  17

<210> SEQ ID NO 190
<211> LENGTH: 17
<212> TYPE: DNA
<213> ORGANISM: Homo sapiens

<400> SEQUENCE: 190
cccttctgcc atcttct                                                  17

<210> SEQ ID NO 191
<211> LENGTH: 17
<212> TYPE: DNA
<213> ORGANISM: Homo sapiens

<400> SEQUENCE: 191
tttgtgaata ttttata                                                  17

<210> SEQ ID NO 192
<211> LENGTH: 17
<212> TYPE: DNA
<213> ORGANISM: Homo sapiens

<400> SEQUENCE: 192
gggtgcaaaa aaaaaat                                                  17

<210> SEQ ID NO 193
<211> LENGTH: 17
<212> TYPE: DNA
<213> ORGANISM: Homo sapiens

<400> SEQUENCE: 193
tatactttga tttcaac                                                  17

<210> SEQ ID NO 194
<211> LENGTH: 17
<212> TYPE: DNA
<213> ORGANISM: Homo sapiens

<400> SEQUENCE: 194
aaggcaaagc tcttgta                                                  17

<210> SEQ ID NO 195
<211> LENGTH: 17
<212> TYPE: DNA
<213> ORGANISM: Homo sapiens

<400> SEQUENCE: 195
gagtaactta aaaatac                                                  17
```

-continued

```
<210> SEQ ID NO 196
<211> LENGTH: 17
<212> TYPE: DNA
<213> ORGANISM: Homo sapiens

<400> SEQUENCE: 196
ccgctgcact ccagcct                                                  17

<210> SEQ ID NO 197
<211> LENGTH: 17
<212> TYPE: DNA
<213> ORGANISM: Homo sapiens

<400> SEQUENCE: 197
cctgtctgat aatcttg                                                  17

<210> SEQ ID NO 198
<211> LENGTH: 17
<212> TYPE: DNA
<213> ORGANISM: Homo sapiens

<400> SEQUENCE: 198
tacaaaacca tttttt                                                   17

<210> SEQ ID NO 199
<211> LENGTH: 17
<212> TYPE: DNA
<213> ORGANISM: Homo sapiens

<400> SEQUENCE: 199
gttacaatca ttgctga                                                  17

<210> SEQ ID NO 200
<211> LENGTH: 17
<212> TYPE: DNA
<213> ORGANISM: Homo sapiens

<400> SEQUENCE: 200
atctctgggc acacagc                                                  17

<210> SEQ ID NO 201
<211> LENGTH: 17
<212> TYPE: DNA
<213> ORGANISM: Homo sapiens

<400> SEQUENCE: 201
gaggaatttg taacgat                                                  17

<210> SEQ ID NO 202
<211> LENGTH: 17
<212> TYPE: DNA
<213> ORGANISM: Homo sapiens

<400> SEQUENCE: 202
cttcactcgt gggccag                                                  17

<210> SEQ ID NO 203
<211> LENGTH: 17
<212> TYPE: DNA
<213> ORGANISM: Homo sapiens

<400> SEQUENCE: 203
cattggtaga atcgtgt                                                  17
```

```
<210> SEQ ID NO 204
<211> LENGTH: 17
<212> TYPE: DNA
<213> ORGANISM: Homo sapiens

<400> SEQUENCE: 204 tcctttttgct tactgtt                                                17

<210> SEQ ID NO 205
<211> LENGTH: 17
<212> TYPE: DNA
<213> ORGANISM: Homo sapiens

<400> SEQUENCE: 205
aaggtaactt gggtttt                                                 17

<210> SEQ ID NO 206
<211> LENGTH: 17
<212> TYPE: DNA
<213> ORGANISM: Homo sapiens

<400> SEQUENCE: 206
acaaacagaa aaattca                                                 17

<210> SEQ ID NO 207
<211> LENGTH: 17
<212> TYPE: DNA
<213> ORGANISM: Homo sapiens

<400> SEQUENCE: 207
cggggacgag gacctgg                                                 17

<210> SEQ ID NO 208
<211> LENGTH: 17
<212> TYPE: DNA
<213> ORGANISM: Homo sapiens

<400> SEQUENCE: 208
acgtctctat tgtacaa                                                 17

<210> SEQ ID NO 209
<211> LENGTH: 17
<212> TYPE: DNA
<213> ORGANISM: Homo sapiens

<400> SEQUENCE: 209
tattattaaa gaggatt                                                 17

<210> SEQ ID NO 210
<211> LENGTH: 17
<212> TYPE: DNA
<213> ORGANISM: Homo sapiens

<400> SEQUENCE: 210
tcagactttg agctgat                                                 17

<210> SEQ ID NO 211
<211> LENGTH: 17
<212> TYPE: DNA
<213> ORGANISM: Homo sapiens

<400> SEQUENCE: 211
ttaataaaca aagtaac                                                 17
```

<210> SEQ ID NO 212
<211> LENGTH: 17
<212> TYPE: DNA
<213> ORGANISM: Homo sapiens

<400> SEQUENCE: 212
tatatagtga gatgtct                                                17

<210> SEQ ID NO 213
<211> LENGTH: 17
<212> TYPE: DNA
<213> ORGANISM: Homo sapiens

<400> SEQUENCE: 213
cacctatcaa tgtgttt                                                17

<210> SEQ ID NO 214
<211> LENGTH: 17
<212> TYPE: DNA
<213> ORGANISM: Homo sapiens

<400> SEQUENCE: 214
ttgtagctca atacaat                                                17

<210> SEQ ID NO 215
<211> LENGTH: 17
<212> TYPE: DNA
<213> ORGANISM: Homo sapiens

<400> SEQUENCE: 215
tcacactggc tatcaaa                                                17

<210> SEQ ID NO 216
<211> LENGTH: 17
<212> TYPE: DNA
<213> ORGANISM: Homo sapiens

<400> SEQUENCE: 216
actttatttt tgttggg                                                17

<210> SEQ ID NO 217
<211> LENGTH: 17
<212> TYPE: DNA
<213> ORGANISM: Homo sapiens

<400> SEQUENCE: 217
gacatcacaa gaccatc                                                17

<210> SEQ ID NO 218
<211> LENGTH: 17
<212> TYPE: DNA
<213> ORGANISM: Homo sapiens

<400> SEQUENCE: 218
gtaaacacca tttccca                                                17

<210> SEQ ID NO 219
<211> LENGTH: 17
<212> TYPE: DNA
<213> ORGANISM: Homo sapiens

<400> SEQUENCE: 219
tctgcaagca gttcttc                                                17

<210> SEQ ID NO 220
<211> LENGTH: 17
<212> TYPE: DNA
<213> ORGANISM: Homo sapiens

<400> SEQUENCE: 220
tttatcatct ttacttt                                                17

<210> SEQ ID NO 221
<211> LENGTH: 17
<212> TYPE: DNA
<213> ORGANISM: Homo sapiens

<400> SEQUENCE: 221
taaaatactc cacaata                                                17

<210> SEQ ID NO 222
<211> LENGTH: 17
<212> TYPE: DNA
<213> ORGANISM: Homo sapiens

<400> SEQUENCE: 222
aaattgaatt tcccgat                                                17

<210> SEQ ID NO 223
<211> LENGTH: 17
<212> TYPE: DNA
<213> ORGANISM: Homo sapiens

<400> SEQUENCE: 223
gtgtggtcac tgtcaaa                                                17

<210> SEQ ID NO 224
<211> LENGTH: 17
<212> TYPE: DNA
<213> ORGANISM: Homo sapiens

<400> SEQUENCE: 224
ttggttttaa tagtgtc                                                17

<210> SEQ ID NO 225
<211> LENGTH: 17
<212> TYPE: DNA
<213> ORGANISM: Homo sapiens

<400> SEQUENCE: 225
tggctagatt tatgcta                                                17

<210> SEQ ID NO 226
<211> LENGTH: 17
<212> TYPE: DNA
<213> ORGANISM: Homo sapiens

<400> SEQUENCE: 226
ggtagtttta aataaat                                                17

<210> SEQ ID NO 227
<211> LENGTH: 17
<212> TYPE: DNA
<213> ORGANISM: Homo sapiens

<400> SEQUENCE: 227
tttgtcggtc cgggctt                                                17

<210> SEQ ID NO 228
<211> LENGTH: 17
<212> TYPE: DNA
<213> ORGANISM: Homo sapiens

<400> SEQUENCE: 228
tgagatacaa ggctaca                                                17

<210> SEQ ID NO 229
<211> LENGTH: 17
<212> TYPE: DNA
<213> ORGANISM: Homo sapiens

<400> SEQUENCE: 229
ggcgtcctgg ccgcagc                                                17

<210> SEQ ID NO 230
<211> LENGTH: 17
<212> TYPE: DNA
<213> ORGANISM: Homo sapiens

<400> SEQUENCE: 230
gagttaggca cttcctg                                                17

<210> SEQ ID NO 231
<211> LENGTH: 17
<212> TYPE: DNA
<213> ORGANISM: Homo sapiens

<400> SEQUENCE: 231
tgcacttgac ctgacag                                                17

<210> SEQ ID NO 232
<211> LENGTH: 17
<212> TYPE: DNA
<213> ORGANISM: Homo sapiens

<400> SEQUENCE: 232
cccagcaaga gccttgc                                                17

<210> SEQ ID NO 233
<211> LENGTH: 17
<212> TYPE: DNA
<213> ORGANISM: Homo sapiens

<400> SEQUENCE: 233
cctaggacct ggggccc                                                17

<210> SEQ ID NO 234
<211> LENGTH: 17
<212> TYPE: DNA
<213> ORGANISM: Homo sapiens

<400> SEQUENCE: 234
atattttaaa tgttaag                                                17

<210> SEQ ID NO 235
<211> LENGTH: 17
<212> TYPE: DNA
<213> ORGANISM: Homo sapiens

```
<400> SEQUENCE: 235
tacttgtgtt tataaaa                                              17

<210> SEQ ID NO 236
<211> LENGTH: 17
<212> TYPE: DNA
<213> ORGANISM: Homo sapiens

<400> SEQUENCE: 236
aagaactaaa aaaaaaa                                              17

<210> SEQ ID NO 237
<211> LENGTH: 17
<212> TYPE: DNA
<213> ORGANISM: Homo sapiens

<400> SEQUENCE: 237
accagagagc atttagg                                              17

<210> SEQ ID NO 238
<211> LENGTH: 17
<212> TYPE: DNA
<213> ORGANISM: Homo sapiens

<400> SEQUENCE: 238
caatcagaat ctcactg                                              17

<210> SEQ ID NO 239
<211> LENGTH: 17
<212> TYPE: DNA
<213> ORGANISM: Homo sapiens

<400> SEQUENCE: 239
attaaagaat gctgtct                                              17

<210> SEQ ID NO 240
<211> LENGTH: 17
<212> TYPE: DNA
<213> ORGANISM: Homo sapiens

<400> SEQUENCE: 240
attctgcttt ctgttag                                              17

<210> SEQ ID NO 241
<211> LENGTH: 17
<212> TYPE: DNA
<213> ORGANISM: Homo sapiens

<400> SEQUENCE: 241
atgtacaggt ttgtagc                                              17

<210> SEQ ID NO 242
<211> LENGTH: 17
<212> TYPE: DNA
<213> ORGANISM: Homo sapiens

<400> SEQUENCE: 242
ctggcaggcc acagccc                                              17

<210> SEQ ID NO 243
<211> LENGTH: 17
<212> TYPE: DNA
<213> ORGANISM: Homo sapiens
```

```
<400> SEQUENCE: 243
taactgtctt aaaaaaa                                                17

<210> SEQ ID NO 244
<211> LENGTH: 17
<212> TYPE: DNA
<213> ORGANISM: Homo sapiens

<400> SEQUENCE: 244
tgatgggtgg ggtgcct                                                17

<210> SEQ ID NO 245
<211> LENGTH: 17
<212> TYPE: DNA
<213> ORGANISM: Homo sapiens

<400> SEQUENCE: 245
ttgctatgat ggacagg                                                17

<210> SEQ ID NO 246
<211> LENGTH: 17
<212> TYPE: DNA
<213> ORGANISM: Homo sapiens

<400> SEQUENCE: 246
ggcccggctt tcctgga                                                17

<210> SEQ ID NO 247
<211> LENGTH: 17
<212> TYPE: DNA
<213> ORGANISM: Homo sapiens

<400> SEQUENCE: 247
ttaagagaag ggagtgt                                                17

<210> SEQ ID NO 248
<211> LENGTH: 17
<212> TYPE: DNA
<213> ORGANISM: Homo sapiens

<400> SEQUENCE: 248
attatcacat tctgcca                                                17

<210> SEQ ID NO 249
<211> LENGTH: 17
<212> TYPE: DNA
<213> ORGANISM: Homo sapiens

<400> SEQUENCE: 249
aacgttcttg tctgtgt                                                17

<210> SEQ ID NO 250
<211> LENGTH: 17
<212> TYPE: DNA
<213> ORGANISM: Homo sapiens

<400> SEQUENCE: 250
gatgggctgc ctccagg                                                17

<210> SEQ ID NO 251
<211> LENGTH: 17
<212> TYPE: DNA
```

```
<213> ORGANISM: Homo sapiens

<400> SEQUENCE: 251
tggggagctc ggctgca                                                    17

<210> SEQ ID NO 252
<211> LENGTH: 17
<212> TYPE: DNA
<213> ORGANISM: Homo sapiens

<400> SEQUENCE: 252
gaaaaaataa agccatt                                                    17

<210> SEQ ID NO 253
<211> LENGTH: 17
<212> TYPE: DNA
<213> ORGANISM: Homo sapiens

<400> SEQUENCE: 253
cactgcaagg ctgtgac                                                    17

<210> SEQ ID NO 254
<211> LENGTH: 17
<212> TYPE: DNA
<213> ORGANISM: Homo sapiens

<400> SEQUENCE: 254
gctggagcta gaatttg                                                    17

<210> SEQ ID NO 255
<211> LENGTH: 17
<212> TYPE: DNA
<213> ORGANISM: Homo sapiens

<400> SEQUENCE: 255
tgtctgcctg acccgta                                                    17

<210> SEQ ID NO 256
<211> LENGTH: 17
<212> TYPE: DNA
<213> ORGANISM: Homo sapiens

<400> SEQUENCE: 256
tgtctgcctg acccgta                                                    17

<210> SEQ ID NO 257
<211> LENGTH: 17
<212> TYPE: DNA
<213> ORGANISM: Homo sapiens

<400> SEQUENCE: 257
aagatcctac gagagat                                                    17

<210> SEQ ID NO 258
<211> LENGTH: 17
<212> TYPE: DNA
<213> ORGANISM: Homo sapiens

<400> SEQUENCE: 258
ctaatggggt acaccat                                                    17

<210> SEQ ID NO 259
<211> LENGTH: 17
```

```
<212> TYPE: DNA
<213> ORGANISM: Homo sapiens

<400> SEQUENCE: 259
atgaaaggtg tcaataa                                                    17

<210> SEQ ID NO 260
<211> LENGTH: 17
<212> TYPE: DNA
<213> ORGANISM: Homo sapiens

<400> SEQUENCE: 260
agtcaagccc cctcccc                                                    17

<210> SEQ ID NO 261
<211> LENGTH: 17
<212> TYPE: DNA
<213> ORGANISM: Homo sapiens

<400> SEQUENCE: 261
tttctcatac ccagata                                                    17

<210> SEQ ID NO 262
<211> LENGTH: 17
<212> TYPE: DNA
<213> ORGANISM: Homo sapiens

<400> SEQUENCE: 262
ttcttcatta tatcttc                                                    17

<210> SEQ ID NO 263
<211> LENGTH: 17
<212> TYPE: DNA
<213> ORGANISM: Homo sapiens

<400> SEQUENCE: 263
aagaaattct tctgtct                                                    17

<210> SEQ ID NO 264
<211> LENGTH: 17
<212> TYPE: DNA
<213> ORGANISM: Homo sapiens

<400> SEQUENCE: 264
ttactcttag taaataa                                                    17

<210> SEQ ID NO 265
<211> LENGTH: 17
<212> TYPE: DNA
<213> ORGANISM: Homo sapiens

<400> SEQUENCE: 265
gacatttgtc ctcgggc                                                    17

<210> SEQ ID NO 266
<211> LENGTH: 17
<212> TYPE: DNA
<213> ORGANISM: Homo sapiens

<400> SEQUENCE: 266
gtggcagccg gaggtgc                                                    17

<210> SEQ ID NO 267
```

<211> LENGTH: 17
<212> TYPE: DNA
<213> ORGANISM: Homo sapiens

<400> SEQUENCE: 267
tcaatatcac tgttttt                                                 17

<210> SEQ ID NO 268
<211> LENGTH: 17
<212> TYPE: DNA
<213> ORGANISM: Homo sapiens

<400> SEQUENCE: 268
atgacctgaa gttcacc                                                 17

<210> SEQ ID NO 269
<211> LENGTH: 17
<212> TYPE: DNA
<213> ORGANISM: Homo sapiens

<400> SEQUENCE: 269
aacctctgta ttgcttt                                                 17

<210> SEQ ID NO 270
<211> LENGTH: 17
<212> TYPE: DNA
<213> ORGANISM: Homo sapiens

<400> SEQUENCE: 270
gatctgttcc tctgtgc                                                 17

<210> SEQ ID NO 271
<211> LENGTH: 17
<212> TYPE: DNA
<213> ORGANISM: Homo sapiens

<400> SEQUENCE: 271
gtgtcctcct cctcctc                                                 17

<210> SEQ ID NO 272
<211> LENGTH: 17
<212> TYPE: DNA
<213> ORGANISM: Homo sapiens

<400> SEQUENCE: 272
cattgtcttc acgaaga                                                 17

<210> SEQ ID NO 273
<211> LENGTH: 17
<212> TYPE: DNA
<213> ORGANISM: Homo sapiens

<400> SEQUENCE: 273
acttatgttt attacta                                                 17

<210> SEQ ID NO 274
<211> LENGTH: 17
<212> TYPE: DNA
<213> ORGANISM: Homo sapiens

<400> SEQUENCE: 274
agtttgttaa atagctt                                                 17

<210> SEQ ID NO 275
<211> LENGTH: 17
<212> TYPE: DNA
<213> ORGANISM: Homo sapiens

<400> SEQUENCE: 275
ttgcccaggc tggtctt                                              17

<210> SEQ ID NO 276
<211> LENGTH: 17
<212> TYPE: DNA
<213> ORGANISM: Homo sapiens

<400> SEQUENCE: 276
ccctcctgct cccccca                                              17

<210> SEQ ID NO 277
<211> LENGTH: 17
<212> TYPE: DNA
<213> ORGANISM: Homo sapiens

<400> SEQUENCE: 277
cgtgggtggg gagggag                                              17

<210> SEQ ID NO 278
<211> LENGTH: 17
<212> TYPE: DNA
<213> ORGANISM: Homo sapiens

<400> SEQUENCE: 278
aatattagag aaggaat                                              17

<210> SEQ ID NO 279
<211> LENGTH: 17
<212> TYPE: DNA
<213> ORGANISM: Homo sapiens

<400> SEQUENCE: 279
cctggagcaa tgagggt                                              17

<210> SEQ ID NO 280
<211> LENGTH: 17
<212> TYPE: DNA
<213> ORGANISM: Homo sapiens

<400> SEQUENCE: 280
gcttgctggc caggata                                              17

<210> SEQ ID NO 281
<211> LENGTH: 17
<212> TYPE: DNA
<213> ORGANISM: Homo sapiens

<400> SEQUENCE: 281
ttaataaaca ggaacac                                              17

<210> SEQ ID NO 282
<211> LENGTH: 17
<212> TYPE: DNA
<213> ORGANISM: Homo sapiens

<400> SEQUENCE: 282
tagcaatcag attttcc                                              17

```
<210> SEQ ID NO 283
<211> LENGTH: 17
<212> TYPE: DNA
<213> ORGANISM: Homo sapiens

<400> SEQUENCE: 283
cgtgcctgct ggggagg                                                  17

<210> SEQ ID NO 284
<211> LENGTH: 17
<212> TYPE: DNA
<213> ORGANISM: Homo sapiens

<400> SEQUENCE: 284
agcaccagaa cagatga                                                  17

<210> SEQ ID NO 285
<211> LENGTH: 17
<212> TYPE: DNA
<213> ORGANISM: Homo sapiens

<400> SEQUENCE: 285
ccccaagaca cagggac                                                  17

<210> SEQ ID NO 286
<211> LENGTH: 17
<212> TYPE: DNA
<213> ORGANISM: Homo sapiens

<400> SEQUENCE: 286
ggggcagtga gaccagg                                                  17

<210> SEQ ID NO 287
<211> LENGTH: 17
<212> TYPE: DNA
<213> ORGANISM: Homo sapiens

<400> SEQUENCE: 287
ctagaaagag ctcagtg                                                  17

<210> SEQ ID NO 288
<211> LENGTH: 17
<212> TYPE: DNA
<213> ORGANISM: Homo sapiens

<400> SEQUENCE: 288
caaatgaatt tttggtg                                                  17

<210> SEQ ID NO 289
<211> LENGTH: 17
<212> TYPE: DNA
<213> ORGANISM: Homo sapiens

<400> SEQUENCE: 289
ggttgagtgt ggccacc                                                  17

<210> SEQ ID NO 290
<211> LENGTH: 17
<212> TYPE: DNA
<213> ORGANISM: Homo sapiens

<400> SEQUENCE: 290
gcgaaacccc gtctcta                                                  17
```

<210> SEQ ID NO 291
<211> LENGTH: 17
<212> TYPE: DNA
<213> ORGANISM: Homo sapiens

<400> SEQUENCE: 291
agtcttctga ctctgtt                                                17

<210> SEQ ID NO 292
<211> LENGTH: 17
<212> TYPE: DNA
<213> ORGANISM: Homo sapiens

<400> SEQUENCE: 292
tttggaatgt taaaaaa                                                17

<210> SEQ ID NO 293
<211> LENGTH: 17
<212> TYPE: DNA
<213> ORGANISM: Homo sapiens

<400> SEQUENCE: 293
cggtcccatt gtgaaat                                                17

<210> SEQ ID NO 294
<211> LENGTH: 17
<212> TYPE: DNA
<213> ORGANISM: Homo sapiens

<400> SEQUENCE: 294
gttgtagact ttcacct                                                17

<210> SEQ ID NO 295
<211> LENGTH: 17
<212> TYPE: DNA
<213> ORGANISM: Homo sapiens

<400> SEQUENCE: 295
ttactttttc ctttgct                                                17

<210> SEQ ID NO 296
<211> LENGTH: 17
<212> TYPE: DNA
<213> ORGANISM: Homo sapiens

<400> SEQUENCE: 296
cgaggctgta ggaagag                                                17

<210> SEQ ID NO 297
<211> LENGTH: 17
<212> TYPE: DNA
<213> ORGANISM: Homo sapiens

<400> SEQUENCE: 297
ggtgaacttt atgagtg                                                17

<210> SEQ ID NO 298
<211> LENGTH: 17
<212> TYPE: DNA
<213> ORGANISM: Homo sapiens

<400> SEQUENCE: 298

```
cctgacctca accccgc                                                    17

<210> SEQ ID NO 299
<211> LENGTH: 17
<212> TYPE: DNA
<213> ORGANISM: Homo sapiens

<400> SEQUENCE: 299
tttgtataga aaaaatg                                                    17

<210> SEQ ID NO 300
<211> LENGTH: 17
<212> TYPE: DNA
<213> ORGANISM: Homo sapiens

<400> SEQUENCE: 300
gaccagcctt cagatgg                                                    17

<210> SEQ ID NO 301
<211> LENGTH: 17
<212> TYPE: DNA
<213> ORGANISM: Homo sapiens

<400> SEQUENCE: 301
taatttggaa gggctca                                                    17

<210> SEQ ID NO 302
<211> LENGTH: 17
<212> TYPE: DNA
<213> ORGANISM: Homo sapiens

<400> SEQUENCE: 302
gccccgtgag ggttttg                                                    17

<210> SEQ ID NO 303
<211> LENGTH: 17
<212> TYPE: DNA
<213> ORGANISM: Homo sapiens

<400> SEQUENCE: 303
aatgctttac cattcaa                                                    17

<210> SEQ ID NO 304
<211> LENGTH: 17
<212> TYPE: DNA
<213> ORGANISM: Homo sapiens

<400> SEQUENCE: 304
cagactgccc tgctggg                                                    17

<210> SEQ ID NO 305
<211> LENGTH: 17
<212> TYPE: DNA
<213> ORGANISM: Homo sapiens

<400> SEQUENCE: 305
ggaggtgtgg tttattg                                                    17

<210> SEQ ID NO 306
<211> LENGTH: 17
<212> TYPE: DNA
<213> ORGANISM: Homo sapiens

<400> SEQUENCE: 306
```
gttgcagata aactgat     17

<210> SEQ ID NO 307
<211> LENGTH: 17
<212> TYPE: DNA
<213> ORGANISM: Homo sapiens

<400> SEQUENCE: 307
acaatgaagc agatatg     17

<210> SEQ ID NO 308
<211> LENGTH: 17
<212> TYPE: DNA
<213> ORGANISM: Homo sapiens

<400> SEQUENCE: 308
ttctgaagac aaatttt     17

<210> SEQ ID NO 309
<211> LENGTH: 17
<212> TYPE: DNA
<213> ORGANISM: Homo sapiens

<400> SEQUENCE: 309
ataaattaga cccagtc     17

<210> SEQ ID NO 310
<211> LENGTH: 17
<212> TYPE: DNA
<213> ORGANISM: Homo sapiens

<400> SEQUENCE: 310
tatatacatt tggaaat     17

<210> SEQ ID NO 311
<211> LENGTH: 17
<212> TYPE: DNA
<213> ORGANISM: Homo sapiens

<400> SEQUENCE: 311
tcagaagttc ctaattc     17

<210> SEQ ID NO 312
<211> LENGTH: 17
<212> TYPE: DNA
<213> ORGANISM: Homo sapiens

<400> SEQUENCE: 312
tatattttct attagtt     17

<210> SEQ ID NO 313
<211> LENGTH: 17
<212> TYPE: DNA
<213> ORGANISM: Homo sapiens

<400> SEQUENCE: 313
cttgtataca tatttaa     17

<210> SEQ ID NO 314
<211> LENGTH: 17
<212> TYPE: DNA
<213> ORGANISM: Homo sapiens

```
<400> SEQUENCE: 314
tcggagctgc tggagcc                                                17

<210> SEQ ID NO 315
<211> LENGTH: 17
<212> TYPE: DNA
<213> ORGANISM: Homo sapiens

<400> SEQUENCE: 315
caacagttgt cctaagg                                                17

<210> SEQ ID NO 316
<211> LENGTH: 17
<212> TYPE: DNA
<213> ORGANISM: Homo sapiens

<400> SEQUENCE: 316
gttgatggtg gggtccc                                                17

<210> SEQ ID NO 317
<211> LENGTH: 17
<212> TYPE: DNA
<213> ORGANISM: Homo sapiens

<400> SEQUENCE: 317
cgctacttaa tggaaga                                                17

<210> SEQ ID NO 318
<211> LENGTH: 17
<212> TYPE: DNA
<213> ORGANISM: Homo sapiens

<400> SEQUENCE: 318
gtgcccacag ggagcac                                                17

<210> SEQ ID NO 319
<211> LENGTH: 17
<212> TYPE: DNA
<213> ORGANISM: Homo sapiens

<400> SEQUENCE: 319
atgtgaggga gatgaga                                                17

<210> SEQ ID NO 320
<211> LENGTH: 17
<212> TYPE: DNA
<213> ORGANISM: Homo sapiens

<400> SEQUENCE: 320
ttttgaagat tgtttaa                                                17

<210> SEQ ID NO 321
<211> LENGTH: 17
<212> TYPE: DNA
<213> ORGANISM: Homo sapiens

<400> SEQUENCE: 321
aaggagcggg aacgccg                                                17

<210> SEQ ID NO 322
<211> LENGTH: 17
<212> TYPE: DNA
<213> ORGANISM: Homo sapiens
```

```
<400> SEQUENCE: 322
gctctgccgt cctgcct                                               17

<210> SEQ ID NO 323
<211> LENGTH: 17
<212> TYPE: DNA
<213> ORGANISM: Homo sapiens

<400> SEQUENCE: 323
tagcagcaat gcagatt                                               17

<210> SEQ ID NO 324
<211> LENGTH: 17
<212> TYPE: DNA
<213> ORGANISM: Homo sapiens

<400> SEQUENCE: 324
gcctctttcc ttggaca                                               17

<210> SEQ ID NO 325
<211> LENGTH: 17
<212> TYPE: DNA
<213> ORGANISM: Homo sapiens

<400> SEQUENCE: 325
caggatttaa tattttc                                               17

<210> SEQ ID NO 326
<211> LENGTH: 17
<212> TYPE: DNA
<213> ORGANISM: Homo sapiens

<400> SEQUENCE: 326
ggtagctcag gggagga                                               17

<210> SEQ ID NO 327
<211> LENGTH: 17
<212> TYPE: DNA
<213> ORGANISM: Homo sapiens

<400> SEQUENCE: 327
gtctacctga tccgggt                                               17

<210> SEQ ID NO 328
<211> LENGTH: 17
<212> TYPE: DNA
<213> ORGANISM: Homo sapiens

<400> SEQUENCE: 328 cggctttct gcatcaa                                                17

<210> SEQ ID NO 329
<211> LENGTH: 17
<212> TYPE: DNA
<213> ORGANISM: Homo sapiens

<400> SEQUENCE: 329
tgcacacgtg cccaggc                                               17

<210> SEQ ID NO 330
<211> LENGTH: 17
<212> TYPE: DNA
```

```
<213> ORGANISM: Homo sapiens

<400> SEQUENCE: 330
ttgaaatata tgtgttg                                                    17

<210> SEQ ID NO 331
<211> LENGTH: 17
<212> TYPE: DNA
<213> ORGANISM: Homo sapiens

<400> SEQUENCE: 331
cagagaatat atattgt                                                    17

<210> SEQ ID NO 332
<211> LENGTH: 17
<212> TYPE: DNA
<213> ORGANISM: Homo sapiens

<400> SEQUENCE: 332
ggcatcaggg gctggcc                                                    17

<210> SEQ ID NO 333
<211> LENGTH: 17
<212> TYPE: DNA
<213> ORGANISM: Homo sapiens

<400> SEQUENCE: 333
gagaccttct tctaccg                                                    17

<210> SEQ ID NO 334
<211> LENGTH: 17
<212> TYPE: DNA
<213> ORGANISM: Homo sapiens

<400> SEQUENCE: 334
ggagtaataa tgggtca                                                    17

<210> SEQ ID NO 335
<211> LENGTH: 17
<212> TYPE: DNA
<213> ORGANISM: Homo sapiens

<400> SEQUENCE: 335
tgtgttaaga aacactg                                                    17

<210> SEQ ID NO 336
<211> LENGTH: 17
<212> TYPE: DNA
<213> ORGANISM: Homo sapiens

<400> SEQUENCE: 336
gctgagaata tgacggc                                                    17

<210> SEQ ID NO 337
<211> LENGTH: 17
<212> TYPE: DNA
<213> ORGANISM: Homo sapiens

<400> SEQUENCE: 337
gtgaaactag tgatgaa                                                    17

<210> SEQ ID NO 338
<211> LENGTH: 17
```

<212> TYPE: DNA
<213> ORGANISM: Homo sapiens

<400> SEQUENCE: 338
gagaaaccct gtctcta                                          17

<210> SEQ ID NO 339
<211> LENGTH: 17
<212> TYPE: DNA
<213> ORGANISM: Homo sapiens

<400> SEQUENCE: 339
ctgttatagg atctaca                                          17

<210> SEQ ID NO 340
<211> LENGTH: 17
<212> TYPE: DNA
<213> ORGANISM: Homo sapiens

<400> SEQUENCE: 340
gccacactgt cagtgag                                          17

<210> SEQ ID NO 341
<211> LENGTH: 17
<212> TYPE: DNA
<213> ORGANISM: Homo sapiens

<400> SEQUENCE: 341
caaaatactg cagattt                                          17

<210> SEQ ID NO 342
<211> LENGTH: 17
<212> TYPE: DNA
<213> ORGANISM: Homo sapiens

<400> SEQUENCE: 342
cacatcccca cctcggg                                          17

<210> SEQ ID NO 343
<211> LENGTH: 17
<212> TYPE: DNA
<213> ORGANISM: Homo sapiens

<400> SEQUENCE: 343
actacctccc ccaggag                                          17

<210> SEQ ID NO 344
<211> LENGTH: 17
<212> TYPE: DNA
<213> ORGANISM: Homo sapiens

<400> SEQUENCE: 344
atccatagtg aaattgc                                          17

<210> SEQ ID NO 345
<211> LENGTH: 17
<212> TYPE: DNA
<213> ORGANISM: Homo sapiens

<400> SEQUENCE: 345
tcagatccgt cgatccc                                          17

<210> SEQ ID NO 346

```
<211> LENGTH: 17
<212> TYPE: DNA
<213> ORGANISM: Homo sapiens

<400> SEQUENCE: 346 tgttgattttt atttgac                                                 17

<210> SEQ ID NO 347
<211> LENGTH: 17
<212> TYPE: DNA
<213> ORGANISM: Homo sapiens

<400> SEQUENCE: 347
gttccagtga ggccaag                                                  17

<210> SEQ ID NO 348
<211> LENGTH: 17
<212> TYPE: DNA
<213> ORGANISM: Homo sapiens

<400> SEQUENCE: 348
cagaacctca acgaccg                                                  17

<210> SEQ ID NO 349
<211> LENGTH: 17
<212> TYPE: DNA
<213> ORGANISM: Homo sapiens

<400> SEQUENCE: 349
ggatggcaat gtccaca                                                  17

<210> SEQ ID NO 350
<211> LENGTH: 17
<212> TYPE: DNA
<213> ORGANISM: Homo sapiens

<400> SEQUENCE: 350
aagtgattct gttgaca                                                  17

<210> SEQ ID NO 351
<211> LENGTH: 17
<212> TYPE: DNA
<213> ORGANISM: Homo sapiens

<400> SEQUENCE: 351
ttcccaaagg ccagcgg                                                  17

<210> SEQ ID NO 352
<211> LENGTH: 17
<212> TYPE: DNA
<213> ORGANISM: Homo sapiens

<400> SEQUENCE: 352
acttcacaaa gaccta                                                   17

<210> SEQ ID NO 353
<211> LENGTH: 17
<212> TYPE: DNA
<213> ORGANISM: Homo sapiens

<400> SEQUENCE: 353
taagaactaa gagttct                                                  17
```

```
<210> SEQ ID NO 354
<211> LENGTH: 17
<212> TYPE: DNA
<213> ORGANISM: Homo sapiens

<400> SEQUENCE: 354
caggacagtt tttcaac                                                   17

<210> SEQ ID NO 355
<211> LENGTH: 17
<212> TYPE: DNA
<213> ORGANISM: Homo sapiens

<400> SEQUENCE: 355
ctgtgcccag ttcaata                                                   17

<210> SEQ ID NO 356
<211> LENGTH: 17
<212> TYPE: DNA
<213> ORGANISM: Homo sapiens

<400> SEQUENCE: 356
ttgtttaatt tcttttt                                                   17

<210> SEQ ID NO 357
<211> LENGTH: 17
<212> TYPE: DNA
<213> ORGANISM: Homo sapiens

<400> SEQUENCE: 357
taaatacagt atgctct                                                   17

<210> SEQ ID NO 358
<211> LENGTH: 17
<212> TYPE: DNA
<213> ORGANISM: Homo sapiens

<400> SEQUENCE: 358
gtttcagcac tagccaa                                                   17

<210> SEQ ID NO 359
<211> LENGTH: 17
<212> TYPE: DNA
<213> ORGANISM: Homo sapiens

<400> SEQUENCE: 359
attaagacaa taaagta                                                   17

<210> SEQ ID NO 360
<211> LENGTH: 17
<212> TYPE: DNA
<213> ORGANISM: Homo sapiens

<400> SEQUENCE: 360
ctgcttccag agccctc                                                   17

<210> SEQ ID NO 361
<211> LENGTH: 17
<212> TYPE: DNA
<213> ORGANISM: Homo sapiens

<400> SEQUENCE: 361
ccacaatcct atgctct                                                   17
```

```
<210> SEQ ID NO 362
<211> LENGTH: 17
<212> TYPE: DNA
<213> ORGANISM: Homo sapiens

<400> SEQUENCE: 362
ctgtgccaat ggctggc                                                    17

<210> SEQ ID NO 363
<211> LENGTH: 17
<212> TYPE: DNA
<213> ORGANISM: Homo sapiens

<400> SEQUENCE: 363
taacactgac tttatcc                                                    17

<210> SEQ ID NO 364
<211> LENGTH: 17
<212> TYPE: DNA
<213> ORGANISM: Homo sapiens

<400> SEQUENCE: 364
atttgagatg tagaagc                                                    17

<210> SEQ ID NO 365
<211> LENGTH: 17
<212> TYPE: DNA
<213> ORGANISM: Homo sapiens

<400> SEQUENCE: 365
ttggccagga tggtctt                                                    17

<210> SEQ ID NO 366
<211> LENGTH: 17
<212> TYPE: DNA
<213> ORGANISM: Homo sapiens

<400> SEQUENCE: 366
tttaattcaa agaagag                                                    17

<210> SEQ ID NO 367
<211> LENGTH: 17
<212> TYPE: DNA
<213> ORGANISM: Homo sapiens

<400> SEQUENCE: 367
caggatccag aagttat                                                    17

<210> SEQ ID NO 368
<211> LENGTH: 17
<212> TYPE: DNA
<213> ORGANISM: Homo sapiens

<400> SEQUENCE: 368
tgctaattgt aaccaca                                                    17

<210> SEQ ID NO 369
<211> LENGTH: 17
<212> TYPE: DNA
<213> ORGANISM: Homo sapiens

<400> SEQUENCE: 369
ggcaagagac aatttgg                                                    17
```

<210> SEQ ID NO 370
<211> LENGTH: 17
<212> TYPE: DNA
<213> ORGANISM: Homo sapiens

<400> SEQUENCE: 370
gaaatccgca cttctcct                                                    17

<210> SEQ ID NO 371
<211> LENGTH: 17
<212> TYPE: DNA
<213> ORGANISM: Homo sapiens

<400> SEQUENCE: 371
ccccaagacc ccagggc                                                     17

<210> SEQ ID NO 372
<211> LENGTH: 17
<212> TYPE: DNA
<213> ORGANISM: Homo sapiens

<400> SEQUENCE: 372
gaactggatt tggattt                                                     17

<210> SEQ ID NO 373
<211> LENGTH: 17
<212> TYPE: DNA
<213> ORGANISM: Homo sapiens

<400> SEQUENCE: 373
caagacgggg gttagtg                                                     17

<210> SEQ ID NO 374
<211> LENGTH: 17
<212> TYPE: DNA
<213> ORGANISM: Homo sapiens

<400> SEQUENCE: 374
ttcatatagt caatgta                                                     17

<210> SEQ ID NO 375
<211> LENGTH: 17
<212> TYPE: DNA
<213> ORGANISM: Homo sapiens

<400> SEQUENCE: 375
aacttgggct tttctgg                                                     17

<210> SEQ ID NO 376
<211> LENGTH: 17
<212> TYPE: DNA
<213> ORGANISM: Homo sapiens

<400> SEQUENCE: 376
gttaatctgg aacttac                                                     17

<210> SEQ ID NO 377
<211> LENGTH: 17
<212> TYPE: DNA
<213> ORGANISM: Homo sapiens

<400> SEQUENCE: 377

```
gccaatgtgg gcggctt                                              17

<210> SEQ ID NO 378
<211> LENGTH: 17
<212> TYPE: DNA
<213> ORGANISM: Homo sapiens

<400> SEQUENCE: 378
caatttaaag taactta                                              17

<210> SEQ ID NO 379
<211> LENGTH: 17
<212> TYPE: DNA
<213> ORGANISM: Homo sapiens

<400> SEQUENCE: 379
tactgtgatg tctgatg                                              17

<210> SEQ ID NO 380
<211> LENGTH: 17
<212> TYPE: DNA
<213> ORGANISM: Homo sapiens

<400> SEQUENCE: 380
gtgaagctga tgcagcg                                              17

<210> SEQ ID NO 381
<211> LENGTH: 17
<212> TYPE: DNA
<213> ORGANISM: Homo sapiens

<400> SEQUENCE: 381
aaatgtaatt tacttgg                                              17

<210> SEQ ID NO 382
<211> LENGTH: 17
<212> TYPE: DNA
<213> ORGANISM: Homo sapiens

<400> SEQUENCE: 382
cccccaccta agtcaca                                              17

<210> SEQ ID NO 383
<211> LENGTH: 17
<212> TYPE: DNA
<213> ORGANISM: Homo sapiens

<400> SEQUENCE: 383
aattaactcc gttaaaa                                              17

<210> SEQ ID NO 384
<211> LENGTH: 17
<212> TYPE: DNA
<213> ORGANISM: Homo sapiens

<400> SEQUENCE: 384
gaaccttaat gaccaaa                                              17

<210> SEQ ID NO 385
<211> LENGTH: 17
<212> TYPE: DNA
<213> ORGANISM: Homo sapiens

<400> SEQUENCE: 385
```
atccctcccc actgacc                                                        17

<210> SEQ ID NO 386
<211> LENGTH: 17
<212> TYPE: DNA
<213> ORGANISM: Homo sapiens

<400> SEQUENCE: 386
ttatattttc ttttaag                                                        17

<210> SEQ ID NO 387
<211> LENGTH: 17
<212> TYPE: DNA
<213> ORGANISM: Homo sapiens

<400> SEQUENCE: 387
cttgacatac ctaccag                                                        17

<210> SEQ ID NO 388
<211> LENGTH: 17
<212> TYPE: DNA
<213> ORGANISM: Homo sapiens

<400> SEQUENCE: 388
aatttttttt caatgta                                                        17

<210> SEQ ID NO 389
<211> LENGTH: 17
<212> TYPE: DNA
<213> ORGANISM: Homo sapiens

<400> SEQUENCE: 389
tggtagagcg ttttctc                                                        17

<210> SEQ ID NO 390
<211> LENGTH: 17
<212> TYPE: DNA
<213> ORGANISM: Homo sapiens

<400> SEQUENCE: 390
catataatgt acagtgt                                                        17

<210> SEQ ID NO 391
<211> LENGTH: 17
<212> TYPE: DNA
<213> ORGANISM: Homo sapiens

<400> SEQUENCE: 391
cattcattgg ttgttca                                                        17

<210> SEQ ID NO 392
<211> LENGTH: 17
<212> TYPE: DNA
<213> ORGANISM: Homo sapiens

<400> SEQUENCE: 392
gtggatgtac agtttgt                                                        17

<210> SEQ ID NO 393
<211> LENGTH: 17
<212> TYPE: DNA
<213> ORGANISM: Homo sapiens

```
<400> SEQUENCE: 393
ctactgggaa caagttt                                                      17

<210> SEQ ID NO 394
<211> LENGTH: 17
<212> TYPE: DNA
<213> ORGANISM: Homo sapiens

<400> SEQUENCE: 394
agtcagctgg aaagtct                                                      17

<210> SEQ ID NO 395
<211> LENGTH: 17
<212> TYPE: DNA
<213> ORGANISM: Homo sapiens

<400> SEQUENCE: 395
taccaggaac catttaa                                                      17

<210> SEQ ID NO 396
<211> LENGTH: 17
<212> TYPE: DNA
<213> ORGANISM: Homo sapiens

<400> SEQUENCE: 396
tccaagctaa agcctta                                                      17

<210> SEQ ID NO 397
<211> LENGTH: 17
<212> TYPE: DNA
<213> ORGANISM: Homo sapiens

<400> SEQUENCE: 397
gagccttggg tacccct                                                      17

<210> SEQ ID NO 398
<211> LENGTH: 17
<212> TYPE: DNA
<213> ORGANISM: Homo sapiens

<400> SEQUENCE: 398
ccaatgcagc tgtgaac                                                      17

<210> SEQ ID NO 399
<211> LENGTH: 17
<212> TYPE: DNA
<213> ORGANISM: Homo sapiens

<400> SEQUENCE: 399
cggcgctccc ttccttc                                                      17

<210> SEQ ID NO 400
<211> LENGTH: 17
<212> TYPE: DNA
<213> ORGANISM: Homo sapiens

<400> SEQUENCE: 400
tactagtttt agttttc                                                      17

<210> SEQ ID NO 401
<211> LENGTH: 17
<212> TYPE: DNA
<213> ORGANISM: Homo sapiens
```

<400> SEQUENCE: 401
taatttgcat tactctg                                                          17

<210> SEQ ID NO 402
<211> LENGTH: 17
<212> TYPE: DNA
<213> ORGANISM: Homo sapiens

<400> SEQUENCE: 402
tacacccgct cttcaag                                                          17

<210> SEQ ID NO 403
<211> LENGTH: 17
<212> TYPE: DNA
<213> ORGANISM: Homo sapiens

<400> SEQUENCE: 403
aatgcgtgta ctgttac                                                          17

<210> SEQ ID NO 404
<211> LENGTH: 17
<212> TYPE: DNA
<213> ORGANISM: Homo sapiens

<400> SEQUENCE: 404 aagaccccg tggagct                                                           17

<210> SEQ ID NO 405
<211> LENGTH: 17
<212> TYPE: DNA
<213> ORGANISM: Homo sapiens

<400> SEQUENCE: 405
tgtgctgtgc tgtgtct                                                          17

<210> SEQ ID NO 406
<211> LENGTH: 17
<212> TYPE: DNA
<213> ORGANISM: Homo sapiens

<400> SEQUENCE: 406
gaactcaggc caggctc                                                          17

<210> SEQ ID NO 407
<211> LENGTH: 17
<212> TYPE: DNA
<213> ORGANISM: Homo sapiens

<400> SEQUENCE: 407
cgcgctgtgg gcaattg                                                          17

<210> SEQ ID NO 408
<211> LENGTH: 17
<212> TYPE: DNA
<213> ORGANISM: Homo sapiens

<400> SEQUENCE: 408 caccccagg ctctgca                                                           17

<210> SEQ ID NO 409
<211> LENGTH: 17
<212> TYPE: DNA

```
<213> ORGANISM: Homo sapiens

<400> SEQUENCE: 409
aagaaggcac gggtcgg                                                17

<210> SEQ ID NO 410
<211> LENGTH: 17
<212> TYPE: DNA
<213> ORGANISM: Homo sapiens

<400> SEQUENCE: 410
ttcttgtttt gttatat                                                17

<210> SEQ ID NO 411
<211> LENGTH: 17
<212> TYPE: DNA
<213> ORGANISM: Homo sapiens

<400> SEQUENCE: 411
ggatttggcc ttttcga                                                17

<210> SEQ ID NO 412
<211> LENGTH: 17
<212> TYPE: DNA
<213> ORGANISM: Homo sapiens

<400> SEQUENCE: 412
tcaatggcct ctttgtc                                                17

<210> SEQ ID NO 413
<211> LENGTH: 17
<212> TYPE: DNA
<213> ORGANISM: Homo sapiens

<400> SEQUENCE: 413
tcagagatga gggccgc                                                17

<210> SEQ ID NO 414
<211> LENGTH: 17
<212> TYPE: DNA
<213> ORGANISM: Homo sapiens

<400> SEQUENCE: 414
gggctggacg gctgcgt                                                17

<210> SEQ ID NO 415
<211> LENGTH: 17
<212> TYPE: DNA
<213> ORGANISM: Homo sapiens

<400> SEQUENCE: 415
gtctttagga aatattg                                                17

<210> SEQ ID NO 416
<211> LENGTH: 17
<212> TYPE: DNA
<213> ORGANISM: Homo sapiens

<400> SEQUENCE: 416
aagtgaggag atggtta                                                17

<210> SEQ ID NO 417
<211> LENGTH: 17
```

```
<212> TYPE: DNA
<213> ORGANISM: Homo sapiens

<400> SEQUENCE: 417
tgttcccttt gtctttc                                                17

<210> SEQ ID NO 418
<211> LENGTH: 17
<212> TYPE: DNA
<213> ORGANISM: Homo sapiens

<400> SEQUENCE: 418
ggttcaaggc cctggcc                                                17

<210> SEQ ID NO 419
<211> LENGTH: 17
<212> TYPE: DNA
<213> ORGANISM: Homo sapiens

<400> SEQUENCE: 419
cctgtaatcc cagatac                                                17

<210> SEQ ID NO 420
<211> LENGTH: 17
<212> TYPE: DNA
<213> ORGANISM: Homo sapiens

<400> SEQUENCE: 420
tgggaaaaaa tattaca                                                17

<210> SEQ ID NO 421
<211> LENGTH: 17
<212> TYPE: DNA
<213> ORGANISM: Homo sapiens

<400> SEQUENCE: 421
cattcagttg agtccca                                                17

<210> SEQ ID NO 422
<211> LENGTH: 17
<212> TYPE: DNA
<213> ORGANISM: Homo sapiens

<400> SEQUENCE: 422
gaacaccgtc cctctgc                                                17

<210> SEQ ID NO 423
<211> LENGTH: 17
<212> TYPE: DNA
<213> ORGANISM: Homo sapiens

<400> SEQUENCE: 423
cgtgttgttc ctgtgcc                                                17

<210> SEQ ID NO 424
<211> LENGTH: 17
<212> TYPE: DNA
<213> ORGANISM: Homo sapiens

<400> SEQUENCE: 424
gtaggtgagg tggttaa                                                17

<210> SEQ ID NO 425
```

```
<211> LENGTH: 17
<212> TYPE: DNA
<213> ORGANISM: Homo sapiens

<400> SEQUENCE: 425
atctcaaaga tacacag                                                      17

<210> SEQ ID NO 426
<211> LENGTH: 17
<212> TYPE: DNA
<213> ORGANISM: Homo sapiens

<400> SEQUENCE: 426
atgttaggga tgtggat                                                      17

<210> SEQ ID NO 427
<211> LENGTH: 17
<212> TYPE: DNA
<213> ORGANISM: Homo sapiens

<400> SEQUENCE: 427
cacttgccct taaaaac                                                      17

<210> SEQ ID NO 428
<211> LENGTH: 17
<212> TYPE: DNA
<213> ORGANISM: Homo sapiens

<400> SEQUENCE: 428
tgtcccctca ctctgtc                                                      17

<210> SEQ ID NO 429
<211> LENGTH: 17
<212> TYPE: DNA
<213> ORGANISM: Homo sapiens

<400> SEQUENCE: 429
ggtcccctcc cctctca                                                      17

<210> SEQ ID NO 430
<211> LENGTH: 17
<212> TYPE: DNA
<213> ORGANISM: Homo sapiens

<400> SEQUENCE: 430
aatactttag ggtgggg                                                      17

<210> SEQ ID NO 431
<211> LENGTH: 17
<212> TYPE: DNA
<213> ORGANISM: Homo sapiens

<400> SEQUENCE: 431
gaaagcatac ctcagtg                                                      17

<210> SEQ ID NO 432
<211> LENGTH: 17
<212> TYPE: DNA
<213> ORGANISM: Homo sapiens

<400> SEQUENCE: 432
agtatctggg atgtgaa                                                      17
```

```
<210> SEQ ID NO 433
<211> LENGTH: 17
<212> TYPE: DNA
<213> ORGANISM: Homo sapiens

<400> SEQUENCE: 433 tggcccttc aatattt                                                    17

<210> SEQ ID NO 434
<211> LENGTH: 17
<212> TYPE: DNA
<213> ORGANISM: Homo sapiens

<400> SEQUENCE: 434
gacagacatc actactg                                                   17

<210> SEQ ID NO 435
<211> LENGTH: 17
<212> TYPE: DNA
<213> ORGANISM: Homo sapiens

<400> SEQUENCE: 435
tatttattga aaaaaaa                                                   17

<210> SEQ ID NO 436
<211> LENGTH: 17
<212> TYPE: DNA
<213> ORGANISM: Homo sapiens

<400> SEQUENCE: 436
gactctctca gcttccc                                                   17

<210> SEQ ID NO 437
<211> LENGTH: 17
<212> TYPE: DNA
<213> ORGANISM: Homo sapiens

<400> SEQUENCE: 437
tctctgtgta gttccag                                                   17

<210> SEQ ID NO 438
<211> LENGTH: 17
<212> TYPE: DNA
<213> ORGANISM: Homo sapiens

<400> SEQUENCE: 438
taaacaggtt cctttgc                                                   17

<210> SEQ ID NO 439
<211> LENGTH: 17
<212> TYPE: DNA
<213> ORGANISM: Homo sapiens

<400> SEQUENCE: 439
gagcctgtaa atgtttt                                                   17

<210> SEQ ID NO 440
<211> LENGTH: 17
<212> TYPE: DNA
<213> ORGANISM: Homo sapiens

<400> SEQUENCE: 440
caagccaaaa atatacc                                                   17
```

<210> SEQ ID NO 441
<211> LENGTH: 17
<212> TYPE: DNA
<213> ORGANISM: Homo sapiens

<400> SEQUENCE: 441
gacggggtgg agatgga                                                              17

<210> SEQ ID NO 442
<211> LENGTH: 17
<212> TYPE: DNA
<213> ORGANISM: Homo sapiens

<400> SEQUENCE: 442
aacgggccgg cggacgg                                                              17

<210> SEQ ID NO 443
<211> LENGTH: 17
<212> TYPE: DNA
<213> ORGANISM: Homo sapiens

<400> SEQUENCE: 443
aatggcattg atgctaa                                                              17

<210> SEQ ID NO 444
<211> LENGTH: 17
<212> TYPE: DNA
<213> ORGANISM: Homo sapiens

<400> SEQUENCE: 444
tgtgacatcc ggagtcc                                                              17

<210> SEQ ID NO 445
<211> LENGTH: 17
<212> TYPE: DNA
<213> ORGANISM: Homo sapiens

<400> SEQUENCE: 445
tctagagttc tgctgga                                                              17

<210> SEQ ID NO 446
<211> LENGTH: 17
<212> TYPE: DNA
<213> ORGANISM: Homo sapiens

<400> SEQUENCE: 446
tcaaactgct ttattac                                                              17

<210> SEQ ID NO 447
<211> LENGTH: 17
<212> TYPE: DNA
<213> ORGANISM: Homo sapiens

<400> SEQUENCE: 447
ttaaacccac caaaata                                                              17

<210> SEQ ID NO 448
<211> LENGTH: 17
<212> TYPE: DNA
<213> ORGANISM: Homo sapiens

<400> SEQUENCE: 448
gtgtgctggc ttaaaat                                                              17

```
<210> SEQ ID NO 449
<211> LENGTH: 17
<212> TYPE: DNA
<213> ORGANISM: Homo sapiens

<400> SEQUENCE: 449
atttttggtg gaatgtt                                                  17

<210> SEQ ID NO 450
<211> LENGTH: 17
<212> TYPE: DNA
<213> ORGANISM: Homo sapiens

<400> SEQUENCE: 450
tgtttcattc tgatctt                                                  17

<210> SEQ ID NO 451
<211> LENGTH: 17
<212> TYPE: DNA
<213> ORGANISM: Homo sapiens

<400> SEQUENCE: 451
tcaaaaactt ggagtca                                                  17

<210> SEQ ID NO 452
<211> LENGTH: 17
<212> TYPE: DNA
<213> ORGANISM: Homo sapiens

<400> SEQUENCE: 452
ccagccctac tgccgat                                                  17

<210> SEQ ID NO 453
<211> LENGTH: 17
<212> TYPE: DNA
<213> ORGANISM: Homo sapiens

<400> SEQUENCE: 453
gggagccgag tcttctg                                                  17

<210> SEQ ID NO 454
<211> LENGTH: 17
<212> TYPE: DNA
<213> ORGANISM: Homo sapiens

<400> SEQUENCE: 454
tcaactggtt ccggcgt                                                  17

<210> SEQ ID NO 455
<211> LENGTH: 17
<212> TYPE: DNA
<213> ORGANISM: Homo sapiens

<400> SEQUENCE: 455
gtggtgggca cctgtaa                                                  17

<210> SEQ ID NO 456
<211> LENGTH: 17
<212> TYPE: DNA
<213> ORGANISM: Homo sapiens

<400> SEQUENCE: 456
```
ttttttgaaa gcactgg 17

<210> SEQ ID NO 457
<211> LENGTH: 17
<212> TYPE: DNA
<213> ORGANISM: Homo sapiens

<400> SEQUENCE: 457
gggagtaata ggaccag 17

<210> SEQ ID NO 458
<211> LENGTH: 17
<212> TYPE: DNA
<213> ORGANISM: Homo sapiens

<400> SEQUENCE: 458
tggggcctgg gtgggca 17

<210> SEQ ID NO 459
<211> LENGTH: 17
<212> TYPE: DNA
<213> ORGANISM: Homo sapiens

<400> SEQUENCE: 459
tccactcagt aacaagt 17

<210> SEQ ID NO 460
<211> LENGTH: 17
<212> TYPE: DNA
<213> ORGANISM: Homo sapiens

<400> SEQUENCE: 460
gttgtataat atttcat 17

<210> SEQ ID NO 461
<211> LENGTH: 17
<212> TYPE: DNA
<213> ORGANISM: Homo sapiens

<400> SEQUENCE: 461
cttaaaaacg cagagag 17

<210> SEQ ID NO 462
<211> LENGTH: 17
<212> TYPE: DNA
<213> ORGANISM: Homo sapiens

<400> SEQUENCE: 462
tttaaacttt gtgcctt 17

<210> SEQ ID NO 463
<211> LENGTH: 17
<212> TYPE: DNA
<213> ORGANISM: Homo sapiens

<400> SEQUENCE: 463 tttttttataa taaaaca 17

<210> SEQ ID NO 464
<211> LENGTH: 17
<212> TYPE: DNA
<213> ORGANISM: Homo sapiens

<400> SEQUENCE: 464
ctaaaaaatg tagaaga				17

<210> SEQ ID NO 465
<211> LENGTH: 17
<212> TYPE: DNA
<213> ORGANISM: Homo sapiens

<400> SEQUENCE: 465
atattgggaa ccatctc				17

<210> SEQ ID NO 466
<211> LENGTH: 17
<212> TYPE: DNA
<213> ORGANISM: Homo sapiens

<400> SEQUENCE: 466
attaggcctg attatct				17

<210> SEQ ID NO 467
<211> LENGTH: 17
<212> TYPE: DNA
<213> ORGANISM: Homo sapiens

<400> SEQUENCE: 467
ttcttgctta agccatt				17

<210> SEQ ID NO 468
<211> LENGTH: 17
<212> TYPE: DNA
<213> ORGANISM: Homo sapiens

<400> SEQUENCE: 468
atggttacac ttttggt				17

<210> SEQ ID NO 469
<211> LENGTH: 17
<212> TYPE: DNA
<213> ORGANISM: Homo sapiens

<400> SEQUENCE: 469
ctgttactgt acttatg				17

<210> SEQ ID NO 470
<211> LENGTH: 17
<212> TYPE: DNA
<213> ORGANISM: Homo sapiens

<400> SEQUENCE: 470
ggcccccctc ctgggat				17

<210> SEQ ID NO 471
<211> LENGTH: 17
<212> TYPE: DNA
<213> ORGANISM: Homo sapiens

<400> SEQUENCE: 471
cccgtgagcg agctgac				17

<210> SEQ ID NO 472
<211> LENGTH: 17
<212> TYPE: DNA
<213> ORGANISM: Homo sapiens

<400> SEQUENCE: 472
tgaaatctga tttttat                                                  17

<210> SEQ ID NO 473
<211> LENGTH: 17
<212> TYPE: DNA
<213> ORGANISM: Homo sapiens

<400> SEQUENCE: 473
gagttcgacc tgggagc                                                  17

<210> SEQ ID NO 474
<211> LENGTH: 17
<212> TYPE: DNA
<213> ORGANISM: Homo sapiens

<400> SEQUENCE: 474
gccccgccct ccccgcg                                                  17

<210> SEQ ID NO 475
<211> LENGTH: 17
<212> TYPE: DNA
<213> ORGANISM: Homo sapiens

<400> SEQUENCE: 475
ccattctctt tcagctg                                                  17

<210> SEQ ID NO 476
<211> LENGTH: 17
<212> TYPE: DNA
<213> ORGANISM: Homo sapiens

<400> SEQUENCE: 476
agccaccgtg cctggcc                                                  17

<210> SEQ ID NO 477
<211> LENGTH: 17
<212> TYPE: DNA
<213> ORGANISM: Homo sapiens

<400> SEQUENCE: 477
gaccccaagg ccgccga                                                  17

<210> SEQ ID NO 478
<211> LENGTH: 17
<212> TYPE: DNA
<213> ORGANISM: Homo sapiens

<400> SEQUENCE: 478
acatcccaga agaggac                                                  17

<210> SEQ ID NO 479
<211> LENGTH: 17
<212> TYPE: DNA
<213> ORGANISM: Homo sapiens

<400> SEQUENCE: 479
cattaaaggg tctatta                                                  17

<210> SEQ ID NO 480
<211> LENGTH: 17
<212> TYPE: DNA
<213> ORGANISM: Homo sapiens

```
<400> SEQUENCE: 480
gaggccgctg actaccg                                                  17

<210> SEQ ID NO 481
<211> LENGTH: 17
<212> TYPE: DNA
<213> ORGANISM: Homo sapiens

<400> SEQUENCE: 481
tgcacttcac cgccctg                                                  17

<210> SEQ ID NO 482
<211> LENGTH: 17
<212> TYPE: DNA
<213> ORGANISM: Homo sapiens

<400> SEQUENCE: 482
aggtactact acaaacg                                                  17

<210> SEQ ID NO 483
<211> LENGTH: 17
<212> TYPE: DNA
<213> ORGANISM: Homo sapiens

<400> SEQUENCE: 483
taaaaaccca gggttct                                                  17

<210> SEQ ID NO 484
<211> LENGTH: 17
<212> TYPE: DNA
<213> ORGANISM: Homo sapiens

<400> SEQUENCE: 484
tttaatacat aggtgat                                                  17

<210> SEQ ID NO 485
<211> LENGTH: 17
<212> TYPE: DNA
<213> ORGANISM: Homo sapiens

<400> SEQUENCE: 485
aatggcactt aaaataa                                                  17

<210> SEQ ID NO 486
<211> LENGTH: 17
<212> TYPE: DNA
<213> ORGANISM: Homo sapiens

<400> SEQUENCE: 486
cccactgaat tcaggtc                                                  17

<210> SEQ ID NO 487
<211> LENGTH: 17
<212> TYPE: DNA
<213> ORGANISM: Homo sapiens

<400> SEQUENCE: 487
accccagcaa ctgtggt                                                  17

<210> SEQ ID NO 488
<211> LENGTH: 17
<212> TYPE: DNA
```

```
<213> ORGANISM: Homo sapiens

<400> SEQUENCE: 488
gtggaggttc acaacaa                                                    17

<210> SEQ ID NO 489
<211> LENGTH: 17
<212> TYPE: DNA
<213> ORGANISM: Homo sapiens

<400> SEQUENCE: 489
aagttccaga accagaa                                                    17

<210> SEQ ID NO 490
<211> LENGTH: 17
<212> TYPE: DNA
<213> ORGANISM: Homo sapiens

<400> SEQUENCE: 490
gaagtggcag tgaaaaa                                                    17

<210> SEQ ID NO 491
<211> LENGTH: 17
<212> TYPE: DNA
<213> ORGANISM: Homo sapiens

<400> SEQUENCE: 491
gaagaagtag actaatc                                                    17

<210> SEQ ID NO 492
<211> LENGTH: 17
<212> TYPE: DNA
<213> ORGANISM: Homo sapiens

<400> SEQUENCE: 492
cctggcagtt gtactac                                                    17

<210> SEQ ID NO 493
<211> LENGTH: 17
<212> TYPE: DNA
<213> ORGANISM: Homo sapiens

<400> SEQUENCE: 493
ggtccagggc ctgacac                                                    17

<210> SEQ ID NO 494
<211> LENGTH: 17
<212> TYPE: DNA
<213> ORGANISM: Homo sapiens

<400> SEQUENCE: 494
tgttcagttg tggacct                                                    17

<210> SEQ ID NO 495
<211> LENGTH: 17
<212> TYPE: DNA
<213> ORGANISM: Homo sapiens

<400> SEQUENCE: 495
gctgctcatc cattact                                                    17

<210> SEQ ID NO 496
<211> LENGTH: 17
```

<212> TYPE: DNA
<213> ORGANISM: Homo sapiens

<400> SEQUENCE: 496
ctttgtttaa tggattt                                                17

<210> SEQ ID NO 497
<211> LENGTH: 17
<212> TYPE: DNA
<213> ORGANISM: Homo sapiens

<400> SEQUENCE: 497
ttaaattctt aaatgcc                                                17

<210> SEQ ID NO 498
<211> LENGTH: 17
<212> TYPE: DNA
<213> ORGANISM: Homo sapiens

<400> SEQUENCE: 498
tgtaagaaaa ggcccat                                                17

<210> SEQ ID NO 499
<211> LENGTH: 17
<212> TYPE: DNA
<213> ORGANISM: Homo sapiens

<400> SEQUENCE: 499
tccaggctct ggtgggg                                                17

<210> SEQ ID NO 500
<211> LENGTH: 17
<212> TYPE: DNA
<213> ORGANISM: Homo sapiens

<400> SEQUENCE: 500
cttattgtcc caatatc                                                17

<210> SEQ ID NO 501
<211> LENGTH: 17
<212> TYPE: DNA
<213> ORGANISM: Homo sapiens

<400> SEQUENCE: 501
gtttacccgc agacctt                                                17

<210> SEQ ID NO 502
<211> LENGTH: 17
<212> TYPE: DNA
<213> ORGANISM: Homo sapiens

<400> SEQUENCE: 502
tacaaacctg gattttt                                                17

<210> SEQ ID NO 503
<211> LENGTH: 17
<212> TYPE: DNA
<213> ORGANISM: Homo sapiens

<400> SEQUENCE: 503
cagggaatgc cagtccg                                                17

<210> SEQ ID NO 504

-continued

```
<211> LENGTH: 17
<212> TYPE: DNA
<213> ORGANISM: Homo sapiens

<400> SEQUENCE: 504
ctctgccctc ccttctg                                                    17

<210> SEQ ID NO 505
<211> LENGTH: 17
<212> TYPE: DNA
<213> ORGANISM: Homo sapiens

<400> SEQUENCE: 505
cccacaatcc ctttcta                                                    17

<210> SEQ ID NO 506
<211> LENGTH: 17
<212> TYPE: DNA
<213> ORGANISM: Homo sapiens

<400> SEQUENCE: 506
actgctcatt gtagatg                                                    17

<210> SEQ ID NO 507
<211> LENGTH: 17
<212> TYPE: DNA
<213> ORGANISM: Homo sapiens

<400> SEQUENCE: 507
gaagacggtg aaattga                                                    17

<210> SEQ ID NO 508
<211> LENGTH: 17
<212> TYPE: DNA
<213> ORGANISM: Homo sapiens

<400> SEQUENCE: 508
gtcccaaaat gtcattg                                                    17

<210> SEQ ID NO 509
<211> LENGTH: 17
<212> TYPE: DNA
<213> ORGANISM: Homo sapiens

<400> SEQUENCE: 509
tctactgtta ggtgagg                                                    17

<210> SEQ ID NO 510
<211> LENGTH: 17
<212> TYPE: DNA
<213> ORGANISM: Homo sapiens

<400> SEQUENCE: 510
tgatagtcag ttgtaca                                                    17

<210> SEQ ID NO 511
<211> LENGTH: 17
<212> TYPE: DNA
<213> ORGANISM: Homo sapiens

<400> SEQUENCE: 511
cttatttgtt ttaaaac                                                    17
```

```
<210> SEQ ID NO 512
<211> LENGTH: 17
<212> TYPE: DNA
<213> ORGANISM: Homo sapiens

<400> SEQUENCE: 512
aagggtaacc atcatcg                                                    17

<210> SEQ ID NO 513
<211> LENGTH: 17
<212> TYPE: DNA
<213> ORGANISM: Homo sapiens

<400> SEQUENCE: 513
aatgggggtt atggggt                                                    17

<210> SEQ ID NO 514
<211> LENGTH: 17
<212> TYPE: DNA
<213> ORGANISM: Homo sapiens

<400> SEQUENCE: 514
ggaggacgaa gcagtgg                                                    17

<210> SEQ ID NO 515
<211> LENGTH: 17
<212> TYPE: DNA
<213> ORGANISM: Homo sapiens

<400> SEQUENCE: 515
agaaaattca taaaggg                                                    17

<210> SEQ ID NO 516
<211> LENGTH: 17
<212> TYPE: DNA
<213> ORGANISM: Homo sapiens

<400> SEQUENCE: 516
cccaccagga gcaagct                                                    17

<210> SEQ ID NO 517
<211> LENGTH: 17
<212> TYPE: DNA
<213> ORGANISM: Homo sapiens

<400> SEQUENCE: 517
gcctctgtct ccgagct                                                    17

<210> SEQ ID NO 518
<211> LENGTH: 17
<212> TYPE: DNA
<213> ORGANISM: Homo sapiens

<400> SEQUENCE: 518
ggatttggcc tttttgc                                                    17

<210> SEQ ID NO 519
<211> LENGTH: 17
<212> TYPE: DNA
<213> ORGANISM: Homo sapiens

<400> SEQUENCE: 519
aagtttgtgg atggcct                                                    17
```

```
<210> SEQ ID NO 520
<211> LENGTH: 17
<212> TYPE: DNA
<213> ORGANISM: Homo sapiens

<400> SEQUENCE: 520
aattctgaaa gcaagcc                                                    17

<210> SEQ ID NO 521
<211> LENGTH: 17
<212> TYPE: DNA
<213> ORGANISM: Homo sapiens

<400> SEQUENCE: 521
gttggtccct gcggtgg                                                    17

<210> SEQ ID NO 522
<211> LENGTH: 17
<212> TYPE: DNA
<213> ORGANISM: Homo sapiens

<400> SEQUENCE: 522
aaatgccaca cacatag                                                    17

<210> SEQ ID NO 523
<211> LENGTH: 17
<212> TYPE: DNA
<213> ORGANISM: Homo sapiens

<400> SEQUENCE: 523
tctgtgctca ggaagag                                                    17

<210> SEQ ID NO 524
<211> LENGTH: 17
<212> TYPE: DNA
<213> ORGANISM: Homo sapiens

<400> SEQUENCE: 524
ccctgtaata aaattag                                                    17

<210> SEQ ID NO 525
<211> LENGTH: 17
<212> TYPE: DNA
<213> ORGANISM: Homo sapiens

<400> SEQUENCE: 525
aatttgtgaa ggtggaa                                                    17

<210> SEQ ID NO 526
<211> LENGTH: 17
<212> TYPE: DNA
<213> ORGANISM: Homo sapiens

<400> SEQUENCE: 526
tccaagttcc gtcttct                                                    17

<210> SEQ ID NO 527
<211> LENGTH: 17
<212> TYPE: DNA
<213> ORGANISM: Homo sapiens

<400> SEQUENCE: 527
gcatttagtt cagagtg                                                    17
```

```
<210> SEQ ID NO 528
<211> LENGTH: 17
<212> TYPE: DNA
<213> ORGANISM: Homo sapiens

<400> SEQUENCE: 528
agaaggatgc ttatttt                                                  17

<210> SEQ ID NO 529
<211> LENGTH: 17
<212> TYPE: DNA
<213> ORGANISM: Homo sapiens

<400> SEQUENCE: 529
gatttaaaaa tcaagtt                                                  17

<210> SEQ ID NO 530
<211> LENGTH: 17
<212> TYPE: DNA
<213> ORGANISM: Homo sapiens

<400> SEQUENCE: 530
ttggaactca gaccagg                                                  17

<210> SEQ ID NO 531
<211> LENGTH: 17
<212> TYPE: DNA
<213> ORGANISM: Homo sapiens

<400> SEQUENCE: 531
tgcctatagt cccagct                                                  17

<210> SEQ ID NO 532
<211> LENGTH: 17
<212> TYPE: DNA
<213> ORGANISM: Homo sapiens

<400> SEQUENCE: 532
aagtttctga tatctcc                                                  17

<210> SEQ ID NO 533
<211> LENGTH: 17
<212> TYPE: DNA
<213> ORGANISM: Homo sapiens

<400> SEQUENCE: 533
ctggcccgga gaaggaa                                                  17

<210> SEQ ID NO 534
<211> LENGTH: 17
<212> TYPE: DNA
<213> ORGANISM: Homo sapiens

<400> SEQUENCE: 534
accaatgtgt cctagaa                                                  17

<210> SEQ ID NO 535
<211> LENGTH: 17
<212> TYPE: DNA
<213> ORGANISM: Homo sapiens

<400> SEQUENCE: 535
```

```
attcttcgga ctgactg                                              17

<210> SEQ ID NO 536
<211> LENGTH: 17
<212> TYPE: DNA
<213> ORGANISM: Homo sapiens

<400> SEQUENCE: 536
atgaaaccct gtctcta                                              17

<210> SEQ ID NO 537
<211> LENGTH: 17
<212> TYPE: DNA
<213> ORGANISM: Homo sapiens

<400> SEQUENCE: 537
gatttaaaaa aaaaaaa                                              17

<210> SEQ ID NO 538
<211> LENGTH: 17
<212> TYPE: DNA
<213> ORGANISM: Homo sapiens

<400> SEQUENCE: 538
ttccctggga agacggg                                              17

<210> SEQ ID NO 539
<211> LENGTH: 17
<212> TYPE: DNA
<213> ORGANISM: Homo sapiens

<400> SEQUENCE: 539
ctgggtgccc cagcctg                                              17

<210> SEQ ID NO 540
<211> LENGTH: 17
<212> TYPE: DNA
<213> ORGANISM: Homo sapiens

<400> SEQUENCE: 540
tcatctgtga ataaagt                                              17

<210> SEQ ID NO 541
<211> LENGTH: 17
<212> TYPE: DNA
<213> ORGANISM: Homo sapiens

<400> SEQUENCE: 541
ggtactcgat gtgtaat                                              17

<210> SEQ ID NO 542
<211> LENGTH: 17
<212> TYPE: DNA
<213> ORGANISM: Homo sapiens

<400> SEQUENCE: 542
tttcgtagat ggggttt                                              17

<210> SEQ ID NO 543
<211> LENGTH: 17
<212> TYPE: DNA
<213> ORGANISM: Homo sapiens

<400> SEQUENCE: 543
```

```
gaaggcaaga ttgtgtc                                                      17

<210> SEQ ID NO 544
<211> LENGTH: 17
<212> TYPE: DNA
<213> ORGANISM: Homo sapiens

<400> SEQUENCE: 544
ctcacaagtt ttgggaa                                                      17

<210> SEQ ID NO 545
<211> LENGTH: 17
<212> TYPE: DNA
<213> ORGANISM: Homo sapiens

<400> SEQUENCE: 545
attggtaccc tgactgc                                                      17

<210> SEQ ID NO 546
<211> LENGTH: 17
<212> TYPE: DNA
<213> ORGANISM: Homo sapiens

<400> SEQUENCE: 546
aaggccgagt aactgga                                                      17

<210> SEQ ID NO 547
<211> LENGTH: 17
<212> TYPE: DNA
<213> ORGANISM: Homo sapiens

<400> SEQUENCE: 547
gccctgacca caggggg                                                      17

<210> SEQ ID NO 548
<211> LENGTH: 17
<212> TYPE: DNA
<213> ORGANISM: Homo sapiens

<400> SEQUENCE: 548
cagggaagcc accagct                                                      17

<210> SEQ ID NO 549
<211> LENGTH: 17
<212> TYPE: DNA
<213> ORGANISM: Homo sapiens

<400> SEQUENCE: 549
ttgaacaaag ttaagtc                                                      17

<210> SEQ ID NO 550
<211> LENGTH: 17
<212> TYPE: DNA
<213> ORGANISM: Homo sapiens

<400> SEQUENCE: 550
gagcccccgt gattagt                                                      17

<210> SEQ ID NO 551
<211> LENGTH: 17
<212> TYPE: DNA
<213> ORGANISM: Homo sapiens
```

```
<400> SEQUENCE: 551
taaatacaaa ttttgta                                                    17

<210> SEQ ID NO 552
<211> LENGTH: 17
<212> TYPE: DNA
<213> ORGANISM: Homo sapiens

<400> SEQUENCE: 552
cggtttaatt gtgggag                                                    17

<210> SEQ ID NO 553
<211> LENGTH: 17
<212> TYPE: DNA
<213> ORGANISM: Homo sapiens

<400> SEQUENCE: 553
gggctccagg aagcctg                                                    17

<210> SEQ ID NO 554
<211> LENGTH: 17
<212> TYPE: DNA
<213> ORGANISM: Homo sapiens

<400> SEQUENCE: 554
ttcacagtgc agctcct                                                    17

<210> SEQ ID NO 555
<211> LENGTH: 17
<212> TYPE: DNA
<213> ORGANISM: Homo sapiens

<400> SEQUENCE: 555
gctgctgcct gggcctc                                                    17

<210> SEQ ID NO 556
<211> LENGTH: 17
<212> TYPE: DNA
<213> ORGANISM: Homo sapiens

<400> SEQUENCE: 556
cacgttccct agatgca                                                    17

<210> SEQ ID NO 557
<211> LENGTH: 17
<212> TYPE: DNA
<213> ORGANISM: Homo sapiens

<400> SEQUENCE: 557
ctgcagggcc aaaagga                                                    17

<210> SEQ ID NO 558
<211> LENGTH: 17
<212> TYPE: DNA
<213> ORGANISM: Homo sapiens

<400> SEQUENCE: 558
agcactgtac ttcataa                                                    17

<210> SEQ ID NO 559
<211> LENGTH: 17
<212> TYPE: DNA
<213> ORGANISM: Homo sapiens
```

```
<400> SEQUENCE: 559
ccaagggtcc aggctgc                                                  17

<210> SEQ ID NO 560
<211> LENGTH: 17
<212> TYPE: DNA
<213> ORGANISM: Homo sapiens

<400> SEQUENCE: 560
atagacgcaa tgcattg                                                  17

<210> SEQ ID NO 561
<211> LENGTH: 17
<212> TYPE: DNA
<213> ORGANISM: Homo sapiens

<400> SEQUENCE: 561
atcgaacaaa cctgaaa                                                  17

<210> SEQ ID NO 562
<211> LENGTH: 17
<212> TYPE: DNA
<213> ORGANISM: Homo sapiens

<400> SEQUENCE: 562
gcgaaaccct gtctcta                                                  17

<210> SEQ ID NO 563
<211> LENGTH: 17
<212> TYPE: DNA
<213> ORGANISM: Homo sapiens

<400> SEQUENCE: 563
gctgacggaa atctctt                                                  17

<210> SEQ ID NO 564
<211> LENGTH: 17
<212> TYPE: DNA
<213> ORGANISM: Homo sapiens

<400> SEQUENCE: 564
gtactgtctc cacagcc                                                  17

<210> SEQ ID NO 565
<211> LENGTH: 17
<212> TYPE: DNA
<213> ORGANISM: Homo sapiens

<400> SEQUENCE: 565
tcttcttcga agtggct                                                  17

<210> SEQ ID NO 566
<211> LENGTH: 17
<212> TYPE: DNA
<213> ORGANISM: Homo sapiens

<400> SEQUENCE: 566
gttaattgct agttggt                                                  17

<210> SEQ ID NO 567
<211> LENGTH: 17
<212> TYPE: DNA
```

<213> ORGANISM: Homo sapiens

<400> SEQUENCE: 567
aagggagggt ccctgtg                                                          17

<210> SEQ ID NO 568
<211> LENGTH: 17
<212> TYPE: DNA
<213> ORGANISM: Homo sapiens

<400> SEQUENCE: 568
taaacgtggc agccagc                                                          17

<210> SEQ ID NO 569
<211> LENGTH: 17
<212> TYPE: DNA
<213> ORGANISM: Homo sapiens

<400> SEQUENCE: 569
acagcgtctg cttgcgt                                                          17

<210> SEQ ID NO 570
<211> LENGTH: 17
<212> TYPE: DNA
<213> ORGANISM: Homo sapiens

<400> SEQUENCE: 570
tggtacttct cttttcc                                                          17

<210> SEQ ID NO 571
<211> LENGTH: 17
<212> TYPE: DNA
<213> ORGANISM: Homo sapiens

<400> SEQUENCE: 571
caagggccaa gcaaagg                                                          17

<210> SEQ ID NO 572
<211> LENGTH: 17
<212> TYPE: DNA
<213> ORGANISM: Homo sapiens

<400> SEQUENCE: 572
tgtctgatgc tgctgag                                                          17

<210> SEQ ID NO 573
<211> LENGTH: 17
<212> TYPE: DNA
<213> ORGANISM: Homo sapiens

<400> SEQUENCE: 573
tttgcggtcc gggagga                                                          17

<210> SEQ ID NO 574
<211> LENGTH: 17
<212> TYPE: DNA
<213> ORGANISM: Homo sapiens

<400> SEQUENCE: 574
gtgaaacccc atctcta                                                          17

<210> SEQ ID NO 575
<211> LENGTH: 17

```
<212> TYPE: DNA
<213> ORGANISM: Homo sapiens

<400> SEQUENCE: 575
ctacccggta tgactgg                                                    17

<210> SEQ ID NO 576
<211> LENGTH: 17
<212> TYPE: DNA
<213> ORGANISM: Homo sapiens

<400> SEQUENCE: 576
tggaccaggc gcccagc                                                    17

<210> SEQ ID NO 577
<211> LENGTH: 17
<212> TYPE: DNA
<213> ORGANISM: Homo sapiens

<400> SEQUENCE: 577
gttcctcagc caggtgg                                                    17

<210> SEQ ID NO 578
<211> LENGTH: 17
<212> TYPE: DNA
<213> ORGANISM: Homo sapiens

<400> SEQUENCE: 578
aataaaagtg gatttca                                                    17

<210> SEQ ID NO 579
<211> LENGTH: 17
<212> TYPE: DNA
<213> ORGANISM: Homo sapiens

<400> SEQUENCE: 579
cgtgctggcc acggctt                                                    17

<210> SEQ ID NO 580
<211> LENGTH: 17
<212> TYPE: DNA
<213> ORGANISM: Homo sapiens

<400> SEQUENCE: 580
cctgcacact cctcccc                                                    17

<210> SEQ ID NO 581
<211> LENGTH: 17
<212> TYPE: DNA
<213> ORGANISM: Homo sapiens

<400> SEQUENCE: 581
aattcagtga actcttt                                                    17

<210> SEQ ID NO 582
<211> LENGTH: 17
<212> TYPE: DNA
<213> ORGANISM: Homo sapiens

<400> SEQUENCE: 582
tgaaactcat ctcatta                                                    17

<210> SEQ ID NO 583
```

<211> LENGTH: 17
<212> TYPE: DNA
<213> ORGANISM: Homo sapiens

<400> SEQUENCE: 583
ttacttcaac taaaagt                                                    17

<210> SEQ ID NO 584
<211> LENGTH: 17
<212> TYPE: DNA
<213> ORGANISM: Homo sapiens

<400> SEQUENCE: 584
ctgaactgga tcgtagg                                                    17

<210> SEQ ID NO 585
<211> LENGTH: 17
<212> TYPE: DNA
<213> ORGANISM: Homo sapiens

<400> SEQUENCE: 585
aatttagagc attccac                                                    17

<210> SEQ ID NO 586
<211> LENGTH: 17
<212> TYPE: DNA
<213> ORGANISM: Homo sapiens

<400> SEQUENCE: 586
gcgcagactt ccaaata                                                    17

<210> SEQ ID NO 587
<211> LENGTH: 17
<212> TYPE: DNA
<213> ORGANISM: Homo sapiens

<400> SEQUENCE: 587
ttatatactt ttcagta                                                    17

<210> SEQ ID NO 588
<211> LENGTH: 17
<212> TYPE: DNA
<213> ORGANISM: Homo sapiens

<400> SEQUENCE: 588
tttcacccct tttcttc                                                    17

<210> SEQ ID NO 589
<211> LENGTH: 17
<212> TYPE: DNA
<213> ORGANISM: Homo sapiens

<400> SEQUENCE: 589
tacaaataat aaaatgt                                                    17

<210> SEQ ID NO 590
<211> LENGTH: 17
<212> TYPE: DNA
<213> ORGANISM: Homo sapiens

<400> SEQUENCE: 590
tgaaggtgga ttggtcg                                                    17

```
<210> SEQ ID NO 591
<211> LENGTH: 17
<212> TYPE: DNA
<213> ORGANISM: Homo sapiens

<400> SEQUENCE: 591
gccgtgaact ttatgct                                                  17

<210> SEQ ID NO 592
<211> LENGTH: 17
<212> TYPE: DNA
<213> ORGANISM: Homo sapiens

<400> SEQUENCE: 592
tttgatttta gtagtat                                                  17

<210> SEQ ID NO 593
<211> LENGTH: 17
<212> TYPE: DNA
<213> ORGANISM: Homo sapiens

<400> SEQUENCE: 593
ttggtcaggc tggtctg                                                  17

<210> SEQ ID NO 594
<211> LENGTH: 17
<212> TYPE: DNA
<213> ORGANISM: Homo sapiens

<400> SEQUENCE: 594
gagcaattct aggggct                                                  17

<210> SEQ ID NO 595
<211> LENGTH: 17
<212> TYPE: DNA
<213> ORGANISM: Homo sapiens

<400> SEQUENCE: 595
cagataaact tcttcag                                                  17

<210> SEQ ID NO 596
<211> LENGTH: 17
<212> TYPE: DNA
<213> ORGANISM: Homo sapiens

<400> SEQUENCE: 596
ttgcctcctg agcaaag                                                  17

<210> SEQ ID NO 597
<211> LENGTH: 17
<212> TYPE: DNA
<213> ORGANISM: Homo sapiens

<400> SEQUENCE: 597
gtctctttgg gcggaag                                                  17

<210> SEQ ID NO 598
<211> LENGTH: 17
<212> TYPE: DNA
<213> ORGANISM: Homo sapiens

<400> SEQUENCE: 598
aacctgaaca aagaaag                                                  17
```

```
<210> SEQ ID NO 599
<211> LENGTH: 17
<212> TYPE: DNA
<213> ORGANISM: Homo sapiens

<400> SEQUENCE: 599
gtgctgttta attgtaa                                                17

<210> SEQ ID NO 600
<211> LENGTH: 17
<212> TYPE: DNA
<213> ORGANISM: Homo sapiens

<400> SEQUENCE: 600
cattgttggc tatttga                                                17

<210> SEQ ID NO 601
<211> LENGTH: 17
<212> TYPE: DNA
<213> ORGANISM: Homo sapiens

<400> SEQUENCE: 601
ccagggagat ctttgac                                                17

<210> SEQ ID NO 602
<211> LENGTH: 17
<212> TYPE: DNA
<213> ORGANISM: Homo sapiens

<400> SEQUENCE: 602
tcaattcata aaaacaa                                                17

<210> SEQ ID NO 603
<211> LENGTH: 17
<212> TYPE: DNA
<213> ORGANISM: Homo sapiens

<400> SEQUENCE: 603
aaatcctaga atgtatg                                                17

<210> SEQ ID NO 604
<211> LENGTH: 17
<212> TYPE: DNA
<213> ORGANISM: Homo sapiens

<400> SEQUENCE: 604
gtttgttggg aaggtaa                                                17

<210> SEQ ID NO 605
<211> LENGTH: 17
<212> TYPE: DNA
<213> ORGANISM: Homo sapiens

<400> SEQUENCE: 605
tggcggagta ccaagac                                                17

<210> SEQ ID NO 606
<211> LENGTH: 17
<212> TYPE: DNA
<213> ORGANISM: Homo sapiens

<400> SEQUENCE: 606
cgttgtctgc ccacccc                                                17
```

<210> SEQ ID NO 607
<211> LENGTH: 17
<212> TYPE: DNA
<213> ORGANISM: Homo sapiens

<400> SEQUENCE: 607
tgtaagatgc acagtat                                                  17

<210> SEQ ID NO 608
<211> LENGTH: 17
<212> TYPE: DNA
<213> ORGANISM: Homo sapiens

<400> SEQUENCE: 608
ctcggattca agcagct                                                  17

<210> SEQ ID NO 609
<211> LENGTH: 17
<212> TYPE: DNA
<213> ORGANISM: Homo sapiens

<400> SEQUENCE: 609
ccaccacaaa ggccctt                                                  17

<210> SEQ ID NO 610
<211> LENGTH: 17
<212> TYPE: DNA
<213> ORGANISM: Homo sapiens

<400> SEQUENCE: 610
tcccccgtgc acggttc                                                  17

<210> SEQ ID NO 611
<211> LENGTH: 17
<212> TYPE: DNA
<213> ORGANISM: Homo sapiens

<400> SEQUENCE: 611
gttctctttg tacgata                                                  17

<210> SEQ ID NO 612
<211> LENGTH: 17
<212> TYPE: DNA
<213> ORGANISM: Homo sapiens

<400> SEQUENCE: 612
gagtgaaatt cttgttt                                                  17

<210> SEQ ID NO 613
<211> LENGTH: 17
<212> TYPE: DNA
<213> ORGANISM: Homo sapiens

<400> SEQUENCE: 613
taaaacaatg taattga                                                  17

<210> SEQ ID NO 614
<211> LENGTH: 17
<212> TYPE: DNA
<213> ORGANISM: Homo sapiens

<400> SEQUENCE: 614
tggatcacca agataca 17

<210> SEQ ID NO 615
<211> LENGTH: 17
<212> TYPE: DNA
<213> ORGANISM: Homo sapiens

<400> SEQUENCE: 615
ctttgctgta tgtcttc 17

<210> SEQ ID NO 616
<211> LENGTH: 17
<212> TYPE: DNA
<213> ORGANISM: Homo sapiens

<400> SEQUENCE: 616
tttttaggtg acttttt 17

<210> SEQ ID NO 617
<211> LENGTH: 17
<212> TYPE: DNA
<213> ORGANISM: Homo sapiens

<400> SEQUENCE: 617
cctgtggttt tgtgttt 17

<210> SEQ ID NO 618
<211> LENGTH: 17
<212> TYPE: DNA
<213> ORGANISM: Homo sapiens

<400> SEQUENCE: 618
cccttcactt aactagg 17

<210> SEQ ID NO 619
<211> LENGTH: 17
<212> TYPE: DNA
<213> ORGANISM: Homo sapiens

<400> SEQUENCE: 619
tcctgctgcc ggcaaaa 17

<210> SEQ ID NO 620
<211> LENGTH: 17
<212> TYPE: DNA
<213> ORGANISM: Homo sapiens

<400> SEQUENCE: 620
tacttacaaa aactgag 17

<210> SEQ ID NO 621
<211> LENGTH: 17
<212> TYPE: DNA
<213> ORGANISM: Homo sapiens

<400> SEQUENCE: 621
ggctgtaagt tgtactt 17

<210> SEQ ID NO 622
<211> LENGTH: 17
<212> TYPE: DNA
<213> ORGANISM: Homo sapiens

<400> SEQUENCE: 622
ttagccaggc tggtctt                                                    17

<210> SEQ ID NO 623
<211> LENGTH: 17
<212> TYPE: DNA
<213> ORGANISM: Homo sapiens

<400> SEQUENCE: 623
taaattattt catatat                                                    17

<210> SEQ ID NO 624
<211> LENGTH: 17
<212> TYPE: DNA
<213> ORGANISM: Homo sapiens

<400> SEQUENCE: 624
gatcaaaatt tgtgtaa                                                    17

<210> SEQ ID NO 625
<211> LENGTH: 17
<212> TYPE: DNA
<213> ORGANISM: Homo sapiens

<400> SEQUENCE: 625
ttttccaaaa tgttttt                                                    17

<210> SEQ ID NO 626
<211> LENGTH: 17
<212> TYPE: DNA
<213> ORGANISM: Homo sapiens

<400> SEQUENCE: 626
gtggcatagc atctgag                                                    17

<210> SEQ ID NO 627
<211> LENGTH: 17
<212> TYPE: DNA
<213> ORGANISM: Homo sapiens

<400> SEQUENCE: 627
tcactgatgg tcagatt                                                    17

<210> SEQ ID NO 628
<211> LENGTH: 17
<212> TYPE: DNA
<213> ORGANISM: Homo sapiens

<400> SEQUENCE: 628
aaataaaaaa taaaaat                                                    17

<210> SEQ ID NO 629
<211> LENGTH: 17
<212> TYPE: DNA
<213> ORGANISM: Homo sapiens

<400> SEQUENCE: 629
cagaggccct caagtga                                                    17

<210> SEQ ID NO 630
<211> LENGTH: 17
<212> TYPE: DNA
<213> ORGANISM: Homo sapiens

```
<400> SEQUENCE: 630
gctccggtgt ccggctc                                                  17

<210> SEQ ID NO 631
<211> LENGTH: 17
<212> TYPE: DNA
<213> ORGANISM: Homo sapiens

<400> SEQUENCE: 631
tagtaaagac atcttat                                                  17

<210> SEQ ID NO 632
<211> LENGTH: 17
<212> TYPE: DNA
<213> ORGANISM: Homo sapiens

<400> SEQUENCE: 632
atttataatt tcactga                                                  17

<210> SEQ ID NO 633
<211> LENGTH: 17
<212> TYPE: DNA
<213> ORGANISM: Homo sapiens

<400> SEQUENCE: 633
atgtatgggg attagaa                                                  17

<210> SEQ ID NO 634
<211> LENGTH: 17
<212> TYPE: DNA
<213> ORGANISM: Homo sapiens

<400> SEQUENCE: 634
ttgtccctgg caaacct                                                  17

<210> SEQ ID NO 635
<211> LENGTH: 17
<212> TYPE: DNA
<213> ORGANISM: Homo sapiens

<400> SEQUENCE: 635
atcagttaag tcactct                                                  17

<210> SEQ ID NO 636
<211> LENGTH: 17
<212> TYPE: DNA
<213> ORGANISM: Homo sapiens

<400> SEQUENCE: 636
gtttttaaat aagatta                                                  17

<210> SEQ ID NO 637
<211> LENGTH: 17
<212> TYPE: DNA
<213> ORGANISM: Homo sapiens

<400> SEQUENCE: 637
attctggtgg agattcc                                                  17

<210> SEQ ID NO 638
<211> LENGTH: 17
<212> TYPE: DNA
<213> ORGANISM: Homo sapiens
```

<400> SEQUENCE: 638
gccctgaaac acacaca                                                    17

<210> SEQ ID NO 639
<211> LENGTH: 17
<212> TYPE: DNA
<213> ORGANISM: Homo sapiens

<400> SEQUENCE: 639
gcaatatgta tttccct                                                    17

<210> SEQ ID NO 640
<211> LENGTH: 17
<212> TYPE: DNA
<213> ORGANISM: Homo sapiens

<400> SEQUENCE: 640
ataggattgc ctagtgt                                                    17

<210> SEQ ID NO 641
<211> LENGTH: 17
<212> TYPE: DNA
<213> ORGANISM: Homo sapiens

<400> SEQUENCE: 641
gcgagaatcc agctttg                                                    17

<210> SEQ ID NO 642
<211> LENGTH: 17
<212> TYPE: DNA
<213> ORGANISM: Homo sapiens

<400> SEQUENCE: 642
cttttctgaa gagccgg                                                    17

<210> SEQ ID NO 643
<211> LENGTH: 17
<212> TYPE: DNA
<213> ORGANISM: Homo sapiens

<400> SEQUENCE: 643
aatggattac caacaaa                                                    17

<210> SEQ ID NO 644
<211> LENGTH: 17
<212> TYPE: DNA
<213> ORGANISM: Homo sapiens

<400> SEQUENCE: 644
gacaagatct atgaagg                                                    17

<210> SEQ ID NO 645
<211> LENGTH: 17
<212> TYPE: DNA
<213> ORGANISM: Homo sapiens

<400> SEQUENCE: 645
tgttcatcat cttaagt                                                    17

<210> SEQ ID NO 646
<211> LENGTH: 17
<212> TYPE: DNA

<213> ORGANISM: Homo sapiens

<400> SEQUENCE: 646
cagcgcacag atgtgct                                                17

<210> SEQ ID NO 647
<211> LENGTH: 17
<212> TYPE: DNA
<213> ORGANISM: Homo sapiens

<400> SEQUENCE: 647
tcttttcttg tcatcct                                                17

<210> SEQ ID NO 648
<211> LENGTH: 17
<212> TYPE: DNA
<213> ORGANISM: Homo sapiens

<400> SEQUENCE: 648
cactcagtgt ggactgg                                                17

<210> SEQ ID NO 649
<211> LENGTH: 17
<212> TYPE: DNA
<213> ORGANISM: Homo sapiens

<400> SEQUENCE: 649
accaggtcca ctgtgga                                                17

<210> SEQ ID NO 650
<211> LENGTH: 17
<212> TYPE: DNA
<213> ORGANISM: Homo sapiens

<400> SEQUENCE: 650
ggactgggtc gtctgaa                                                17

<210> SEQ ID NO 651
<211> LENGTH: 17
<212> TYPE: DNA
<213> ORGANISM: Homo sapiens

<400> SEQUENCE: 651
ggttgtattt ttctggt                                                17

<210> SEQ ID NO 652
<211> LENGTH: 17
<212> TYPE: DNA
<213> ORGANISM: Homo sapiens

<400> SEQUENCE: 652
aagaagtgag cttagtt                                                17

<210> SEQ ID NO 653
<211> LENGTH: 17
<212> TYPE: DNA
<213> ORGANISM: Homo sapiens

<400> SEQUENCE: 653
gtgatgcgca taggcct                                                17

<210> SEQ ID NO 654
<211> LENGTH: 17

```
<212> TYPE: DNA
<213> ORGANISM: Homo sapiens

<400> SEQUENCE: 654
ccactgcact ccagact                                            17

<210> SEQ ID NO 655
<211> LENGTH: 17
<212> TYPE: DNA
<213> ORGANISM: Homo sapiens

<400> SEQUENCE: 655
gagggccttg tggacac                                            17

<210> SEQ ID NO 656
<211> LENGTH: 17
<212> TYPE: DNA
<213> ORGANISM: Homo sapiens

<400> SEQUENCE: 656
tatgtcaact cattact                                            17

<210> SEQ ID NO 657
<211> LENGTH: 17
<212> TYPE: DNA
<213> ORGANISM: Homo sapiens

<400> SEQUENCE: 657
ttgatcctct tgcaagc                                            17

<210> SEQ ID NO 658
<211> LENGTH: 17
<212> TYPE: DNA
<213> ORGANISM: Homo sapiens

<400> SEQUENCE: 658
taggagaatc caagcga                                            17

<210> SEQ ID NO 659
<211> LENGTH: 17
<212> TYPE: DNA
<213> ORGANISM: Homo sapiens

<400> SEQUENCE: 659
aatatttcag tgctgct                                            17

<210> SEQ ID NO 660
<211> LENGTH: 17
<212> TYPE: DNA
<213> ORGANISM: Homo sapiens

<400> SEQUENCE: 660
agtacctatt tatgtgg                                            17

<210> SEQ ID NO 661
<211> LENGTH: 17
<212> TYPE: DNA
<213> ORGANISM: Homo sapiens

<400> SEQUENCE: 661
taaatgttaa caattag                                            17

<210> SEQ ID NO 662
```

```
<211> LENGTH: 17
<212> TYPE: DNA
<213> ORGANISM: Homo sapiens

<400> SEQUENCE: 662
gtctgccagc ctggctc                                                   17

<210> SEQ ID NO 663
<211> LENGTH: 17
<212> TYPE: DNA
<213> ORGANISM: Homo sapiens

<400> SEQUENCE: 663 aggggggctga gaggttt                                                  17

<210> SEQ ID NO 664
<211> LENGTH: 17
<212> TYPE: DNA
<213> ORGANISM: Homo sapiens

<400> SEQUENCE: 664
tcaccggtca gtgcctt                                                   17

<210> SEQ ID NO 665
<211> LENGTH: 17
<212> TYPE: DNA
<213> ORGANISM: Homo sapiens

<400> SEQUENCE: 665
caggggagtg ggcccgg                                                   17

<210> SEQ ID NO 666
<211> LENGTH: 17
<212> TYPE: DNA
<213> ORGANISM: Homo sapiens

<400> SEQUENCE: 666
cctccctgat gggtggg                                                   17

<210> SEQ ID NO 667
<211> LENGTH: 17
<212> TYPE: DNA
<213> ORGANISM: Homo sapiens

<400> SEQUENCE: 667
gtactgtagc aggggaa                                                   17

<210> SEQ ID NO 668
<211> LENGTH: 17
<212> TYPE: DNA
<213> ORGANISM: Homo sapiens

<400> SEQUENCE: 668
acctgcccct ctttact                                                   17

<210> SEQ ID NO 669
<211> LENGTH: 17
<212> TYPE: DNA
<213> ORGANISM: Homo sapiens

<400> SEQUENCE: 669
aaggtggagt gtgacct                                                   17
```

<210> SEQ ID NO 670
<211> LENGTH: 17
<212> TYPE: DNA
<213> ORGANISM: Homo sapiens

<400> SEQUENCE: 670
ttggtaaggc tgatctc                                                  17

<210> SEQ ID NO 671
<211> LENGTH: 17
<212> TYPE: DNA
<213> ORGANISM: Homo sapiens

<400> SEQUENCE: 671
gtcctagatt gtggata                                                  17

<210> SEQ ID NO 672
<211> LENGTH: 17
<212> TYPE: DNA
<213> ORGANISM: Homo sapiens

<400> SEQUENCE: 672
gtggcgcaca cctgtaa                                                  17

<210> SEQ ID NO 673
<211> LENGTH: 17
<212> TYPE: DNA
<213> ORGANISM: Homo sapiens

<400> SEQUENCE: 673
cttctgaaaa caacagg                                                  17

<210> SEQ ID NO 674
<211> LENGTH: 17
<212> TYPE: DNA
<213> ORGANISM: Homo sapiens

<400> SEQUENCE: 674
tatttgttga gttttgc                                                  17

<210> SEQ ID NO 675
<211> LENGTH: 17
<212> TYPE: DNA
<213> ORGANISM: Homo sapiens

<400> SEQUENCE: 675
gtggcttaca cctgtaa                                                  17

<210> SEQ ID NO 676
<211> LENGTH: 17
<212> TYPE: DNA
<213> ORGANISM: Homo sapiens

<400> SEQUENCE: 676
aaagtggaaa cattggt                                                  17

<210> SEQ ID NO 677
<211> LENGTH: 17
<212> TYPE: DNA
<213> ORGANISM: Homo sapiens

<400> SEQUENCE: 677
ccactgcact ccagtct                                                  17

```
<210> SEQ ID NO 678
<211> LENGTH: 17
<212> TYPE: DNA
<213> ORGANISM: Homo sapiens

<400> SEQUENCE: 678
gcaatgaaaa ttttaag                                                 17

<210> SEQ ID NO 679
<211> LENGTH: 17
<212> TYPE: DNA
<213> ORGANISM: Homo sapiens

<400> SEQUENCE: 679
tatttttact gatcaca                                                 17

<210> SEQ ID NO 680
<211> LENGTH: 17
<212> TYPE: DNA
<213> ORGANISM: Homo sapiens

<400> SEQUENCE: 680
ggaaaaaaaa atcctgt                                                 17

<210> SEQ ID NO 681
<211> LENGTH: 17
<212> TYPE: DNA
<213> ORGANISM: Homo sapiens

<400> SEQUENCE: 681
tttgcctgtt aagttgt                                                 17

<210> SEQ ID NO 682
<211> LENGTH: 17
<212> TYPE: DNA
<213> ORGANISM: Homo sapiens

<400> SEQUENCE: 682
ctaaagtact ttaactg                                                 17

<210> SEQ ID NO 683
<211> LENGTH: 17
<212> TYPE: DNA
<213> ORGANISM: Homo sapiens

<400> SEQUENCE: 683
ctgaaaattg ctgagat                                                 17

<210> SEQ ID NO 684
<211> LENGTH: 17
<212> TYPE: DNA
<213> ORGANISM: Homo sapiens

<400> SEQUENCE: 684
ttctgaaagg attcact                                                 17

<210> SEQ ID NO 685
<211> LENGTH: 17
<212> TYPE: DNA
<213> ORGANISM: Homo sapiens

<400> SEQUENCE: 685
aagaagcagg gcctcta                                                 17
```

```
<210> SEQ ID NO 686
<211> LENGTH: 17
<212> TYPE: DNA
<213> ORGANISM: Homo sapiens

<400> SEQUENCE: 686
agcaagaaac tgcctgc                                                 17

<210> SEQ ID NO 687
<211> LENGTH: 17
<212> TYPE: DNA
<213> ORGANISM: Homo sapiens

<400> SEQUENCE: 687
tattagagaa tgaaaag                                                 17

<210> SEQ ID NO 688
<211> LENGTH: 17
<212> TYPE: DNA
<213> ORGANISM: Homo sapiens

<400> SEQUENCE: 688
tcaagagccg aaggaat                                                 17

<210> SEQ ID NO 689
<211> LENGTH: 18
<212> TYPE: DNA
<213> ORGANISM: Homo sapiens

<400> SEQUENCE: 689
ccccagttgc tgatcasa                                                18

<210> SEQ ID NO 690
<211> LENGTH: 17
<212> TYPE: DNA
<213> ORGANISM: Homo sapiens

<400> SEQUENCE: 690
tgctaatcaa acctgct                                                 17

<210> SEQ ID NO 691
<211> LENGTH: 17
<212> TYPE: DNA
<213> ORGANISM: Homo sapiens

<400> SEQUENCE: 691
tgtttaatac aagttaa                                                 17

<210> SEQ ID NO 692
<211> LENGTH: 17
<212> TYPE: DNA
<213> ORGANISM: Homo sapiens

<400> SEQUENCE: 692
gtccagaatg atgtttg                                                 17

<210> SEQ ID NO 693
<211> LENGTH: 17
<212> TYPE: DNA
<213> ORGANISM: Homo sapiens

<400> SEQUENCE: 693
```
gctcggccgc tagtgcc                                              17

<210> SEQ ID NO 694
<211> LENGTH: 17
<212> TYPE: DNA
<213> ORGANISM: Homo sapiens

<400> SEQUENCE: 694
aaagtgggtg gagccca                                              17

<210> SEQ ID NO 695
<211> LENGTH: 17
<212> TYPE: DNA
<213> ORGANISM: Homo sapiens

<400> SEQUENCE: 695
taaggtattg caaataa                                              17

<210> SEQ ID NO 696
<211> LENGTH: 17
<212> TYPE: DNA
<213> ORGANISM: Homo sapiens

<400> SEQUENCE: 696
ttaccgtccc ctacctc                                              17

<210> SEQ ID NO 697
<211> LENGTH: 17
<212> TYPE: DNA
<213> ORGANISM: Homo sapiens

<400> SEQUENCE: 697
tccaaagcat tgactgt                                              17

<210> SEQ ID NO 698
<211> LENGTH: 17
<212> TYPE: DNA
<213> ORGANISM: Homo sapiens

<400> SEQUENCE: 698
tcttgtcata caaattt                                              17

<210> SEQ ID NO 699
<211> LENGTH: 17
<212> TYPE: DNA
<213> ORGANISM: Homo sapiens

<400> SEQUENCE: 699
tcaacacaga tcgagaa                                              17

<210> SEQ ID NO 700
<211> LENGTH: 17
<212> TYPE: DNA
<213> ORGANISM: Homo sapiens

<400> SEQUENCE: 700
cctgtggtcc cagctac                                              17

<210> SEQ ID NO 701
<211> LENGTH: 17
<212> TYPE: DNA
<213> ORGANISM: Homo sapiens

<400> SEQUENCE: 701
cgggagacat ctttggc					17

<210> SEQ ID NO 702
<211> LENGTH: 17
<212> TYPE: DNA
<213> ORGANISM: Homo sapiens

<400> SEQUENCE: 702
cgggagcacc cggcgct					17

<210> SEQ ID NO 703
<211> LENGTH: 17
<212> TYPE: DNA
<213> ORGANISM: Homo sapiens

<400> SEQUENCE: 703
ctcccttgcc ctgacat					17

<210> SEQ ID NO 704
<211> LENGTH: 17
<212> TYPE: DNA
<213> ORGANISM: Homo sapiens

<400> SEQUENCE: 704
tgtctggatg aagctgg					17

<210> SEQ ID NO 705
<211> LENGTH: 17
<212> TYPE: DNA
<213> ORGANISM: Homo sapiens

<400> SEQUENCE: 705
tagacaatgc tgctaag					17

<210> SEQ ID NO 706
<211> LENGTH: 17
<212> TYPE: DNA
<213> ORGANISM: Homo sapiens

<400> SEQUENCE: 706
tacagaacac acaattt					17

<210> SEQ ID NO 707
<211> LENGTH: 17
<212> TYPE: DNA
<213> ORGANISM: Homo sapiens

<400> SEQUENCE: 707
actatagaga ccccgtg					17

<210> SEQ ID NO 708
<211> LENGTH: 17
<212> TYPE: DNA
<213> ORGANISM: Homo sapiens

<400> SEQUENCE: 708
aaggcccctg ccgccat					17

<210> SEQ ID NO 709
<211> LENGTH: 17
<212> TYPE: DNA
<213> ORGANISM: Homo sapiens

```
<400> SEQUENCE: 709
aatatgggtg attttga                                                    17

<210> SEQ ID NO 710
<211> LENGTH: 17
<212> TYPE: DNA
<213> ORGANISM: Homo sapiens

<400> SEQUENCE: 710 ggctcactttt aaaaaaa                                                   17

<210> SEQ ID NO 711
<211> LENGTH: 17
<212> TYPE: DNA
<213> ORGANISM: Homo sapiens

<400> SEQUENCE: 711
cctgtggcca agctggc                                                    17

<210> SEQ ID NO 712
<211> LENGTH: 17
<212> TYPE: DNA
<213> ORGANISM: Homo sapiens

<400> SEQUENCE: 712
aatgtggctg accttat                                                    17

<210> SEQ ID NO 713
<211> LENGTH: 17
<212> TYPE: DNA
<213> ORGANISM: Homo sapiens

<400> SEQUENCE: 713
gtcggggcgt ccacgcc                                                    17

<210> SEQ ID NO 714
<211> LENGTH: 17
<212> TYPE: DNA
<213> ORGANISM: Homo sapiens

<400> SEQUENCE: 714
cagcagataa ttgttca                                                    17

<210> SEQ ID NO 715
<211> LENGTH: 17
<212> TYPE: DNA
<213> ORGANISM: Homo sapiens

<400> SEQUENCE: 715
aaaaaactcc aaataag                                                    17

<210> SEQ ID NO 716
<211> LENGTH: 17
<212> TYPE: DNA
<213> ORGANISM: Homo sapiens

<400> SEQUENCE: 716
agcagtgacg gatagtt                                                    17

<210> SEQ ID NO 717
<211> LENGTH: 17
<212> TYPE: DNA
<213> ORGANISM: Homo sapiens
```

```
<400> SEQUENCE: 717
aaactaacat tccaagg                                                     17

<210> SEQ ID NO 718
<211> LENGTH: 17
<212> TYPE: DNA
<213> ORGANISM: Homo sapiens

<400> SEQUENCE: 718
agggtgtctt catttgt                                                     17

<210> SEQ ID NO 719
<211> LENGTH: 17
<212> TYPE: DNA
<213> ORGANISM: Homo sapiens

<400> SEQUENCE: 719
tgaatgtggg tgagttt                                                     17

<210> SEQ ID NO 720
<211> LENGTH: 17
<212> TYPE: DNA
<213> ORGANISM: Homo sapiens

<400> SEQUENCE: 720
tgattgattt gtaattt                                                     17

<210> SEQ ID NO 721
<211> LENGTH: 17
<212> TYPE: DNA
<213> ORGANISM: Homo sapiens

<400> SEQUENCE: 721
taaacggcct catttct                                                     17

<210> SEQ ID NO 722
<211> LENGTH: 17
<212> TYPE: DNA
<213> ORGANISM: Homo sapiens

<400> SEQUENCE: 722
cacaccagtt acttcct                                                     17

<210> SEQ ID NO 723
<211> LENGTH: 17
<212> TYPE: DNA
<213> ORGANISM: Homo sapiens

<400> SEQUENCE: 723
taagcagcac gttttaa                                                     17

<210> SEQ ID NO 724
<211> LENGTH: 17
<212> TYPE: DNA
<213> ORGANISM: Homo sapiens

<400> SEQUENCE: 724
ctgccctcgg cctgttc                                                     17

<210> SEQ ID NO 725
<211> LENGTH: 17
<212> TYPE: DNA
```

```
<213> ORGANISM: Homo sapiens

<400> SEQUENCE: 725
cacacagcac aattcag                                                    17

<210> SEQ ID NO 726
<211> LENGTH: 17
<212> TYPE: DNA
<213> ORGANISM: Homo sapiens

<400> SEQUENCE: 726
tttgaaaatt taattaa                                                    17

<210> SEQ ID NO 727
<211> LENGTH: 17
<212> TYPE: DNA
<213> ORGANISM: Homo sapiens

<400> SEQUENCE: 727
cctgctgagg agttcag                                                    17

<210> SEQ ID NO 728
<211> LENGTH: 17
<212> TYPE: DNA
<213> ORGANISM: Homo sapiens

<400> SEQUENCE: 728
acgtcgtcga ccttggc                                                    17

<210> SEQ ID NO 729
<211> LENGTH: 17
<212> TYPE: DNA
<213> ORGANISM: Homo sapiens

<400> SEQUENCE: 729
agccactgca cctggcc                                                    17

<210> SEQ ID NO 730
<211> LENGTH: 17
<212> TYPE: DNA
<213> ORGANISM: Homo sapiens

<400> SEQUENCE: 730
gatcttttgt cctcact                                                    17

<210> SEQ ID NO 731
<211> LENGTH: 17
<212> TYPE: DNA
<213> ORGANISM: Homo sapiens

<400> SEQUENCE: 731
ggcgtttaga gttatac                                                    17

<210> SEQ ID NO 732
<211> LENGTH: 17
<212> TYPE: DNA
<213> ORGANISM: Homo sapiens

<400> SEQUENCE: 732
aactgggcac ctccggg                                                    17

<210> SEQ ID NO 733
<211> LENGTH: 17
```

<212> TYPE: DNA
<213> ORGANISM: Homo sapiens

<400> SEQUENCE: 733
tacttgctat attgagg                                                17

<210> SEQ ID NO 734
<211> LENGTH: 17
<212> TYPE: DNA
<213> ORGANISM: Homo sapiens

<400> SEQUENCE: 734
taccagctct tccgcag                                                17

<210> SEQ ID NO 735
<211> LENGTH: 17
<212> TYPE: DNA
<213> ORGANISM: Homo sapiens

<400> SEQUENCE: 735
aacttacaga attaaag                                                17

<210> SEQ ID NO 736
<211> LENGTH: 17
<212> TYPE: DNA
<213> ORGANISM: Homo sapiens

<400> SEQUENCE: 736
tgcctgtggt cccagct                                                17

<210> SEQ ID NO 737
<211> LENGTH: 17
<212> TYPE: DNA
<213> ORGANISM: Homo sapiens

<400> SEQUENCE: 737
gactatgggg gtgccgg                                                17

<210> SEQ ID NO 738
<211> LENGTH: 17
<212> TYPE: DNA
<213> ORGANISM: Homo sapiens

<400> SEQUENCE: 738
gatttctact gagttgg                                                17

<210> SEQ ID NO 739
<211> LENGTH: 17
<212> TYPE: DNA
<213> ORGANISM: Homo sapiens

<400> SEQUENCE: 739
ctaaactttt tataaaa                                                17

<210> SEQ ID NO 740
<211> LENGTH: 17
<212> TYPE: DNA
<213> ORGANISM: Homo sapiens

<400> SEQUENCE: 740
gcaaaaccct gtctcta                                                17

<210> SEQ ID NO 741

```
<211> LENGTH: 17
<212> TYPE: DNA
<213> ORGANISM: Homo sapiens

<400> SEQUENCE: 741
tcaccttagg tagtagg                                                17

<210> SEQ ID NO 742
<211> LENGTH: 17
<212> TYPE: DNA
<213> ORGANISM: Homo sapiens

<400> SEQUENCE: 742
acacagtatt cgctctt                                                17

<210> SEQ ID NO 743
<211> LENGTH: 17
<212> TYPE: DNA
<213> ORGANISM: Homo sapiens

<400> SEQUENCE: 743
gctgttggtg ggacccg                                                17

<210> SEQ ID NO 744
<211> LENGTH: 17
<212> TYPE: DNA
<213> ORGANISM: Homo sapiens

<400> SEQUENCE: 744
ctgatgccca agggcaa                                                17

<210> SEQ ID NO 745
<211> LENGTH: 17
<212> TYPE: DNA
<213> ORGANISM: Homo sapiens

<400> SEQUENCE: 745
tgttaattta ttgagtg                                                17

<210> SEQ ID NO 746
<211> LENGTH: 17
<212> TYPE: DNA
<213> ORGANISM: Homo sapiens

<400> SEQUENCE: 746
aaaggaatga gccctag                                                17

<210> SEQ ID NO 747
<211> LENGTH: 17
<212> TYPE: DNA
<213> ORGANISM: Homo sapiens

<400> SEQUENCE: 747
ctgctaaggt agtgaat                                                17

<210> SEQ ID NO 748
<211> LENGTH: 17
<212> TYPE: DNA
<213> ORGANISM: Homo sapiens

<400> SEQUENCE: 748
tatcccagaa cttaaag                                                17
```

```
<210> SEQ ID NO 749
<211> LENGTH: 17
<212> TYPE: DNA
<213> ORGANISM: Homo sapiens

<400> SEQUENCE: 749
agatgagatg accacca                                                17

<210> SEQ ID NO 750
<211> LENGTH: 17
<212> TYPE: DNA
<213> ORGANISM: Homo sapiens

<400> SEQUENCE: 750
gccttgggtg acaaatt                                                17

<210> SEQ ID NO 751
<211> LENGTH: 17
<212> TYPE: DNA
<213> ORGANISM: Homo sapiens

<400> SEQUENCE: 751
taaagagtgg tggactt                                                17

<210> SEQ ID NO 752
<211> LENGTH: 17
<212> TYPE: DNA
<213> ORGANISM: Homo sapiens

<400> SEQUENCE: 752
gatgaagaga ttaaacc                                                17

<210> SEQ ID NO 753
<211> LENGTH: 17
<212> TYPE: DNA
<213> ORGANISM: Homo sapiens

<400> SEQUENCE: 753
taaattacaa gccccag                                                17

<210> SEQ ID NO 754
<211> LENGTH: 17
<212> TYPE: DNA
<213> ORGANISM: Homo sapiens

<400> SEQUENCE: 754
tcaataaatt catactt                                                17

<210> SEQ ID NO 755
<211> LENGTH: 17
<212> TYPE: DNA
<213> ORGANISM: Homo sapiens

<400> SEQUENCE: 755
agtggatttt atttacc                                                17

<210> SEQ ID NO 756
<211> LENGTH: 17
<212> TYPE: DNA
<213> ORGANISM: Homo sapiens

<400> SEQUENCE: 756
ttcaaaaagg aattaca                                                17
```

```
<210> SEQ ID NO 757
<211> LENGTH: 17
<212> TYPE: DNA
<213> ORGANISM: Homo sapiens

<400> SEQUENCE: 757
tgcatcgcgg agcagcc                                                 17

<210> SEQ ID NO 758
<211> LENGTH: 17
<212> TYPE: DNA
<213> ORGANISM: Homo sapiens

<400> SEQUENCE: 758
ttttagacct agaaaag                                                 17

<210> SEQ ID NO 759
<211> LENGTH: 17
<212> TYPE: DNA
<213> ORGANISM: Homo sapiens

<400> SEQUENCE: 759
gctaggagtc ccaggga                                                 17

<210> SEQ ID NO 760
<211> LENGTH: 17
<212> TYPE: DNA
<213> ORGANISM: Homo sapiens

<400> SEQUENCE: 760
aaacagtagt gttccca                                                 17

<210> SEQ ID NO 761
<211> LENGTH: 17
<212> TYPE: DNA
<213> ORGANISM: Homo sapiens

<400> SEQUENCE: 761
tctcctaccc ctcactg                                                 17

<210> SEQ ID NO 762
<211> LENGTH: 17
<212> TYPE: DNA
<213> ORGANISM: Homo sapiens

<400> SEQUENCE: 762
gtgctattat taggctt                                                 17

<210> SEQ ID NO 763
<211> LENGTH: 17
<212> TYPE: DNA
<213> ORGANISM: Homo sapiens

<400> SEQUENCE: 763
cagtagatag aggggag                                                 17

<210> SEQ ID NO 764
<211> LENGTH: 17
<212> TYPE: DNA
<213> ORGANISM: Homo sapiens

<400> SEQUENCE: 764
gagaaacccc gtctcta                                                 17
```

<210> SEQ ID NO 765
<211> LENGTH: 17
<212> TYPE: DNA
<213> ORGANISM: Homo sapiens

<400> SEQUENCE: 765
agcaatttca tcaaatc                                                17

<210> SEQ ID NO 766
<211> LENGTH: 17
<212> TYPE: DNA
<213> ORGANISM: Homo sapiens

<400> SEQUENCE: 766
tctgcaagaa ggcctcc                                                17

<210> SEQ ID NO 767
<211> LENGTH: 17
<212> TYPE: DNA
<213> ORGANISM: Homo sapiens

<400> SEQUENCE: 767
acttgcacaa gatggca                                                17

<210> SEQ ID NO 768
<211> LENGTH: 17
<212> TYPE: DNA
<213> ORGANISM: Homo sapiens

<400> SEQUENCE: 768
ctaggtatgg atctcct                                                17

<210> SEQ ID NO 769
<211> LENGTH: 17
<212> TYPE: DNA
<213> ORGANISM: Homo sapiens

<400> SEQUENCE: 769
gtgggggcaa ctcaaac                                                17

<210> SEQ ID NO 770
<211> LENGTH: 17
<212> TYPE: DNA
<213> ORGANISM: Homo sapiens

<400> SEQUENCE: 770
aaatgactta tggggga                                                17

<210> SEQ ID NO 771
<211> LENGTH: 17
<212> TYPE: DNA
<213> ORGANISM: Homo sapiens

<400> SEQUENCE: 771
ccccctgctc ctgtgcc                                                17

<210> SEQ ID NO 772
<211> LENGTH: 17
<212> TYPE: DNA
<213> ORGANISM: Homo sapiens

<400> SEQUENCE: 772

```
tccaggcagt gtgagga                                                    17

<210> SEQ ID NO 773
<211> LENGTH: 17
<212> TYPE: DNA
<213> ORGANISM: Homo sapiens

<400> SEQUENCE: 773
ataaatataa tcagtat                                                    17

<210> SEQ ID NO 774
<211> LENGTH: 17
<212> TYPE: DNA
<213> ORGANISM: Homo sapiens

<400> SEQUENCE: 774
tgccagcctc attcgaa                                                    17

<210> SEQ ID NO 775
<211> LENGTH: 17
<212> TYPE: DNA
<213> ORGANISM: Homo sapiens

<400> SEQUENCE: 775
ttatgagagt tctggag                                                    17

<210> SEQ ID NO 776
<211> LENGTH: 17
<212> TYPE: DNA
<213> ORGANISM: Homo sapiens

<400> SEQUENCE: 776
ggctgccgag tcctgcc                                                    17

<210> SEQ ID NO 777
<211> LENGTH: 17
<212> TYPE: DNA
<213> ORGANISM: Homo sapiens

<400> SEQUENCE: 777
gtgtttattt tctttct                                                    17

<210> SEQ ID NO 778
<211> LENGTH: 17
<212> TYPE: DNA
<213> ORGANISM: Homo sapiens

<400> SEQUENCE: 778
caagctgtaa cttccct                                                    17

<210> SEQ ID NO 779
<211> LENGTH: 17
<212> TYPE: DNA
<213> ORGANISM: Homo sapiens

<400> SEQUENCE: 779
gggaagtgtg cccagct                                                    17

<210> SEQ ID NO 780
<211> LENGTH: 17
<212> TYPE: DNA
<213> ORGANISM: Homo sapiens

<400> SEQUENCE: 780
```
gaacagcaaa cgcctgt    17

<210> SEQ ID NO 781
<211> LENGTH: 17
<212> TYPE: DNA
<213> ORGANISM: Homo sapiens

<400> SEQUENCE: 781
tgtgatcaca aagactg    17

<210> SEQ ID NO 782
<211> LENGTH: 17
<212> TYPE: DNA
<213> ORGANISM: Homo sapiens

<400> SEQUENCE: 782
agggatccta tttgtct    17

<210> SEQ ID NO 783
<211> LENGTH: 17
<212> TYPE: DNA
<213> ORGANISM: Homo sapiens

<400> SEQUENCE: 783
aagagggaag gaaaaga    17

<210> SEQ ID NO 784
<211> LENGTH: 17
<212> TYPE: DNA
<213> ORGANISM: Homo sapiens

<400> SEQUENCE: 784
aggagagaag accctgc    17

<210> SEQ ID NO 785
<211> LENGTH: 17
<212> TYPE: DNA
<213> ORGANISM: Homo sapiens

<400> SEQUENCE: 785
gtattaggtt ttttgag    17

<210> SEQ ID NO 786
<211> LENGTH: 17
<212> TYPE: DNA
<213> ORGANISM: Homo sapiens

<400> SEQUENCE: 786
tgggccttcc ccaggag    17

<210> SEQ ID NO 787
<211> LENGTH: 17
<212> TYPE: DNA
<213> ORGANISM: Homo sapiens

<400> SEQUENCE: 787
agttcttcca ggggacc    17

<210> SEQ ID NO 788
<211> LENGTH: 17
<212> TYPE: DNA
<213> ORGANISM: Homo sapiens

```
<400> SEQUENCE: 788
tccttactag gtgtttt                                              17

<210> SEQ ID NO 789
<211> LENGTH: 17
<212> TYPE: DNA
<213> ORGANISM: Homo sapiens

<400> SEQUENCE: 789
cctcctatta ctgaagt                                              17

<210> SEQ ID NO 790
<211> LENGTH: 17
<212> TYPE: DNA
<213> ORGANISM: Homo sapiens

<400> SEQUENCE: 790
agctgtctgg cctgtga                                              17

<210> SEQ ID NO 791
<211> LENGTH: 17
<212> TYPE: DNA
<213> ORGANISM: Homo sapiens

<400> SEQUENCE: 791 gtccctctg gggcgtc                                               17

<210> SEQ ID NO 792
<211> LENGTH: 17
<212> TYPE: DNA
<213> ORGANISM: Homo sapiens

<400> SEQUENCE: 792
tggtactact gaagaag                                              17

<210> SEQ ID NO 793
<211> LENGTH: 17
<212> TYPE: DNA
<213> ORGANISM: Homo sapiens

<400> SEQUENCE: 793
ctcacctgct acagccg                                              17

<210> SEQ ID NO 794
<211> LENGTH: 17
<212> TYPE: DNA
<213> ORGANISM: Homo sapiens

<400> SEQUENCE: 794
gcccacagta gaatatc                                              17

<210> SEQ ID NO 795
<211> LENGTH: 17
<212> TYPE: DNA
<213> ORGANISM: Homo sapiens

<400> SEQUENCE: 795
gacaaggaag gcaatgt                                              17

<210> SEQ ID NO 796
<211> LENGTH: 17
<212> TYPE: DNA
<213> ORGANISM: Homo sapiens
```

```
<400> SEQUENCE: 796
cagatttcca atcagtg                                                   17

<210> SEQ ID NO 797
<211> LENGTH: 17
<212> TYPE: DNA
<213> ORGANISM: Homo sapiens

<400> SEQUENCE: 797
cccctccctc cttttta                                                   17

<210> SEQ ID NO 798
<211> LENGTH: 17
<212> TYPE: DNA
<213> ORGANISM: Homo sapiens

<400> SEQUENCE: 798
cttctgcaaa ttcgaat                                                   17

<210> SEQ ID NO 799
<211> LENGTH: 17
<212> TYPE: DNA
<213> ORGANISM: Homo sapiens

<400> SEQUENCE: 799
gcagtggcct cagcctt                                                   17

<210> SEQ ID NO 800
<211> LENGTH: 17
<212> TYPE: DNA
<213> ORGANISM: Homo sapiens

<400> SEQUENCE: 800
tcccagccca catagat                                                   17

<210> SEQ ID NO 801
<211> LENGTH: 17
<212> TYPE: DNA
<213> ORGANISM: Homo sapiens

<400> SEQUENCE: 801
ccctccattt gtaagaa                                                   17

<210> SEQ ID NO 802
<211> LENGTH: 17
<212> TYPE: DNA
<213> ORGANISM: Homo sapiens

<400> SEQUENCE: 802
ctgaaacagc tagaaaa                                                   17

<210> SEQ ID NO 803
<211> LENGTH: 17
<212> TYPE: DNA
<213> ORGANISM: Homo sapiens

<400> SEQUENCE: 803
ctaaaggagg tatcttg                                                   17

<210> SEQ ID NO 804
<211> LENGTH: 17
<212> TYPE: DNA
```

<213> ORGANISM: Homo sapiens

<400> SEQUENCE: 804
gtgcactgtg aacctga                                        17

<210> SEQ ID NO 805
<211> LENGTH: 17
<212> TYPE: DNA
<213> ORGANISM: Homo sapiens

<400> SEQUENCE: 805
acaatatcga caccagt                                        17

<210> SEQ ID NO 806
<211> LENGTH: 17
<212> TYPE: DNA
<213> ORGANISM: Homo sapiens

<400> SEQUENCE: 806
ggattaactt gagggtc                                        17

<210> SEQ ID NO 807
<211> LENGTH: 17
<212> TYPE: DNA
<213> ORGANISM: Homo sapiens

<400> SEQUENCE: 807
ctaatttaac tagtcac                                        17

<210> SEQ ID NO 808
<211> LENGTH: 17
<212> TYPE: DNA
<213> ORGANISM: Homo sapiens

<400> SEQUENCE: 808
attaataaaa aaggcaa                                        17

<210> SEQ ID NO 809
<211> LENGTH: 17
<212> TYPE: DNA
<213> ORGANISM: Homo sapiens

<400> SEQUENCE: 809
tgtctttgct ctttctg                                        17

<210> SEQ ID NO 810
<211> LENGTH: 17
<212> TYPE: DNA
<213> ORGANISM: Homo sapiens

<400> SEQUENCE: 810
atttcaatct gccaaag                                        17

<210> SEQ ID NO 811
<211> LENGTH: 17
<212> TYPE: DNA
<213> ORGANISM: Homo sapiens

<400> SEQUENCE: 811
atattagcaa aggtaaa                                        17

<210> SEQ ID NO 812
<211> LENGTH: 17

```
<212> TYPE: DNA
<213> ORGANISM: Homo sapiens

<400> SEQUENCE: 812
cagtcccggc tggccac                                            17

<210> SEQ ID NO 813
<211> LENGTH: 17
<212> TYPE: DNA
<213> ORGANISM: Homo sapiens

<400> SEQUENCE: 813
gtctttcacc cagccag                                            17

<210> SEQ ID NO 814
<211> LENGTH: 17
<212> TYPE: DNA
<213> ORGANISM: Homo sapiens

<400> SEQUENCE: 814 tgatgttta gtgcttt                                             17

<210> SEQ ID NO 815
<211> LENGTH: 17
<212> TYPE: DNA
<213> ORGANISM: Homo sapiens

<400> SEQUENCE: 815
taacaggaaa ttaaatg                                            17

<210> SEQ ID NO 816
<211> LENGTH: 17
<212> TYPE: DNA
<213> ORGANISM: Homo sapiens

<400> SEQUENCE: 816
tctaaaaagg cacagaa                                            17

<210> SEQ ID NO 817
<211> LENGTH: 17
<212> TYPE: DNA
<213> ORGANISM: Homo sapiens

<400> SEQUENCE: 817
atgaacacgg tgatgac                                            17

<210> SEQ ID NO 818
<211> LENGTH: 17
<212> TYPE: DNA
<213> ORGANISM: Homo sapiens

<400> SEQUENCE: 818
gactgtctca tactgct                                            17
```

COMPOSITIONS AND METHODS OF TREATING CANCER HARBORING PIKC3A MUTATIONS

RELATED APPLICATION

This application claims priority from U.S. Provisional Application No. 61/992,541, filed May 13, 2014, the subject matter of which is incorporated herein by reference in its entirety.

GOVERNMENT FUNDING

This invention was made with government support under Grant No. CA160060 awarded by The National Institutes of Health. The United States government has certain rights to the invention.

BACKGROUND

The "Warburg effect" and "glutamine dependency" are two of the most well-known metabolic reprogramming events that occur in cancer cells and distinguish them from many types of normal cells. Normally, glucose is converted to acetyl-CoA, which enters the tricarboxylic acid (TCA) cycle and undergoes oxidative phosphorylation in mitochondria. However, cancer cells convert glucose to lactate even in the presence of oxygen ("Warburg effect"). It was previously thought that the Warburg effect was caused by impaired mitochondrial function in cancer cells. However, recent studies have demonstrated that most cancer cells retain functional mitochondria. Instead of using glucose, most cancer cells utilize glutamine to replenish the TCA cycle. As illustrated in FIG. 1, to enter the TCA cycle, glutamine is first deaminated by glutaminases (GLSs) to generate glutamate. Glutamate is then converted to α-ketoglutarate (α-KG) to replenish the TCA cycle. Three groups of enzymes convert glutamate to α-KG: (1) glutamate pyruvate transaminases (GPTs), (2) glutamate oxaloacetate transaminases (GOTs) and (3) glutamate dehydrogenases (GLUDs). Glutamine metabolites are utilized to produce ATP and synthesize macromolecules, thereby promoting tumor growth. It has long been known that most cancer cells are dependent on glutamine. Although glutamine is a non-essential amino acid, it is nevertheless a required supplement for culturing cancer cells.

Many oncogenes impact glutamine metabolism. Myc overexpression affects glutamine levels by inducing the transcription of GLS1 and the glutamine transporter SLC1A5 (aka ASCT2). In contrast, SLC1A5 expression is repressed by the Rb tumor suppressor, whereas GLS2 was identified as a transcriptional target of p53. In addition, it has been shown that p53 represses the expression of malic enzymes ME1 and ME2, thereby regulating glutamine-dependent NADPH production. A recent study showed that loss of tumor suppressor VHL renders renal cell carcinomas sensitive to glutamine deprivation through HIF-induced metabolic reprograming. Moreover, K-ras up-regulates the aminotransferase GOT1. Though all of these mechanisms impact the production or degradation of glutamine or its metabolites, the reasons that many cancer cells are dependent on glutamine are still unknown or being actively debated.

PIK3CA encodes the catalytic subunit of phosphatidylinositol 3-kinase α (PI3Kα), which plays a key role in regulating cell proliferation, survival and motility. PIK3α consists of a catalytic subunit p110α and one of several regulatory subunits (a major one being p85α). Upon growth factor stimulation, p85 is recruited to phosphorylated receptor protein kinases and adaptor proteins, thereby activating PI3Kα. Activated PI3Kα converts phosphatidylinositol-4,5-biophosphate (PIP2) to phosphatidylinositol-3,4,5-triphosphate (PIP3). The second message PIP3 then activates PDK1 and AKT signaling downstream. PIK3CA is mutated in a wide variety of human cancers.

SUMMARY

Embodiments described herein relate to methods of determining the susceptibility, resistance, and/or sensitivity of cancer cells, precancerous cells or benign tumor cells in a subject to the treatment with an inhibitor of one more enzymes of the glutamine metabolism pathway, such as inhibitors of glutaminase and/or inhibitors of aminotransferase (e.g., glutamate pyruvate transaminase, aspirate aminotransferase, and glutamate dehydrogenase).

In some embodiments, the method includes obtaining a sample of the cancer cells, the precancerous cells or the benign tumor cells from the subject, assaying the cells in the sample for the presence of a mutated PIK3CA gene or a mutant form of PIK3CA protein or a biologically active fragment thereof, and determining that the subject should be treated with the inhibitor if the cancer cells have the mutated PIK3CA gene or the mutant form of PIK3CA protein.

In other embodiments, the method includes obtaining a sample of the cancer cells, the precancerous cells or the benign tumor cells from the subject, measuring the level of GPT2 expression in the cancer cells, comparing the measured level of GPT2 expression in the cancer cells to a control level, and identifying the cancer is more susceptible to treatment with the inhibitor if there is an increase in the measured levels of GPT2 expression in the cancer cells compared to a control level.

In the above methods, the cancer cells and the precancerous cells are obtained from a tumor or a biological sample from the subject such as tumor biopsy or a biological sample comprising urine, blood, cerebrospinal fluid, sputum, serum, stool or bone marrow. In an embodiment, a DNA or RNA hybridization assay is used to detect the PIK3CA DNA or RNA in the sample. In other embodiments, a DNA or RNA hybridization assay is used to detect the GTP2 levels in the sample.

The cancer to be treated, for example, includes lung cancer, digestive and gastrointestinal cancers, gastrointestinal stromal tumors, gastrointestinal carcinoid tumors, colon cancer, rectal cancer, anal cancer, bile duct cancer, small intestine cancer, and stomach (gastric) cancer, esophageal cancer, gall bladder cancer, liver cancer, pancreatic cancer, appendix cancer, breast cancer, ovarian cancer, renal cancer, cancer of the central nervous system, skin cancer, lymphomas, choriocarcinomas, head and neck cancers, osteogenic sarcomas, and blood cancers.

Others embodiment described herein relate to a method for treating a subject having cancer, precancerous cells, or a benign tumor that has or harbors a mutated PIK3CA gene or mutant PIK3CA protein, by administering to the subject a therapeutically effective amount of one more inhibitor of enzymes of the glutamine metabolism pathway, such as inhibitors of glutaminase and/or inhibitors of aminotransferase. In some embodiments, the inhibitor can be an aminotransferase inhibitor, such as aminooxyacetate (AOA). In other embodiments, the inhibitor can be a glutaminase inhibitor such as bis-2-(5-phenylacetamido-1,2,4-thiadiazol-2-yl)ethyl sulfide or CB-839 (Calithera Bioscience, San Francisco, Calif.). In some embodiments, the glutaminase inhibitor comprises CB-839 or a pharmaceutically acceptable salt thereof. In other embodiments, the glutaminase inhibitor has the formula:

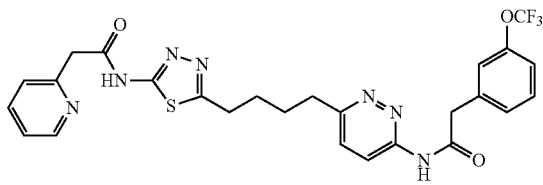 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof.

In other embodiments, the cancer is colorectal cancer.

In an embodiment, the therapeutically effective amount of the inhibitor can be from about 0.1 mg/day to about 150 mg/day.

In the method of treatment, the inhibitor(s) can be administered orally, by injection, parenterally, by inhalation spray, topically, rectally, nasally, buccally, vaginally or via an implanted reservoir. In another embodiment, the inhibitor(s) can be administered locally to the site of the cancer or benign tumor. In an embodiment, the aminotransferase inhibitor is aminooxyacetate (AOA), and the glutaminase inhibitor is bis-2-(5-phenylacetamido-1,2,4-thiadiazol-2-yl) ethyl sulfide or CB-839 (Calithera Bioscience, San Francisco, Calif.).

BRIEF DESCRIPTION OF THE DRAWINGS

FIGS. 2(A-E) illustrate plots, graphs, and immunoblots showing PIK3CA mutant colorectal cancer cells (CRC) cells are more sensitive to glutamine deprivation. (A) Allele configuration of colorectal cancer lines with either the PIK3CA WT or mutant allele knocked out. (B) PIK3CA mutant clones are more sensitive to glutamine, but not glucose, deprivation. Cells of the indicated genotypes were grown in culture and cell numbers were counted under the following conditions: normal medium in the presence of both glucose and glutamine (normal), medium without glutamine (-Gln) and medium without glucose (-Glc). (C-D) Glutamine deprivation induces more apoptosis in PIK3CA mutant clones. Cells of the indicated genotypes were grown with or without 2 mM glutamine for 72 hours. Cell apoptosis was measured by profiling sub-G1 cells and cleaved PARP. (E) Glutamine deprivation induces more apoptosis in PIK3CA mutant CRC cell line. The indicated CRC cell lines were grown without glutamine for 72 hours. Cell apoptosis was measured by profiling sub-G1 cells and cleaved PARP. PIK3CA mutant cell lines: RKO and HT29; WT PIK3CA cell lines: LoVo and SW480.

FIGS. 3(A-F) illustrate immunoblots and graphs showing the up-regulation of GPT2 by PIK3CA mutations renders CRC dependent on glutamine. (A) GPT2 expression levels are up-regulated in PIK3CA mutant clones. RT-PCR analyses of the indicated genes in the HCT116 and DLD1 CRC clones. (B) Western blot analyses of GPT2 in the PIK3CA mutant and WT clones. (C) GPT2 expression levels are higher in PIK3CA mutant CRC specimens. qRT-PCR analyses of GPT2 in tumors with no mutations in the PIK3CA pathway including PIK3CA, PTEN, PDK1 AKTs and IRS (n=10) and tumors with PIK3CA mutations (n=10). Data are plotted as Whiskers (Min to Max). $p<0.05$, t test. (D) Knockdown of GPT2 makes PIK3CA mutant cells resistant to glutamine deprivation GPT2 was knocked down with two independent shRNAs in the HCT116 PIK3CA mutant clone. Stable pools were grown with or without glutamine for three days. Relative survival=(cell number in absence of Gln)/(cell number with Gln)×100%. (E) Knockdown of GPT2 in PIK3CA WT clone does not alter its sensitivity to glutamine deprivation. (F) Overexpression (OE) of GPT2 in PIK3CA WT cells renders them more sensitive to glutamine deprivation. The HCT116 PIK3CA WT clone was transfected with a Flag-tagged GPT2 expression vector. Two stable clones that express Flag-GPT2 were grown with or without glutamine. Data are presented as mean+SEM of three independent cultures. * $p<0.05$; ** $p<0.01$ t test.

FIGS. 4(A-D) illustrate plots showing aminooxyacetate (AOA) inhibits xenograft tumor growth of PIK3CA mutant CRCs but not PIK3CA WT CRCs. (A-B) AOA inhibits growth of xenograft formed by PIK3CA mutant clones but not PIK3CA WT clones. (A) Clones derived from HCT116 cells; (B) Clones derived from DLD1. (C) AOA inhibits growth of xenograft tumors formed by four CRC cell lines harboring PIK3CA mutations. (D) AOA does not inhibit growth of xenograft tumors formed by two CRC cell lines with WT PIK3CA. N=5 mice in each experimental group. Data are presented as mean±SEM. For HCT116 and DLD1 PIK3CA mutant clones, HCT116, DLD1, RKO and HT29, AOA treatment significantly inhibits xenograft tumor growth. *** $p<0.0001$, two-way ANOVA analysis.

FIGS. 5(A-H) illustrate immunoblots and graphs showing ATF4 activates GPT2 transcription. (A-B) ATF4 protein levels correlate with that of GPT2 in PIK3CA WT and mutant clones. Western blot of lysates of cultured cells (A) or lysates of the xenograft tumors form by the HCT116 clones (B). (C) Overexpression of ATF4 in the HCT116 PIK3CA WT clone increases GPT2 protein levels. (D) Knockdown of ATF4 in the HCT116 PIK3CA mutant clone decreases GPT2 transcription. (E) Knockdown of ATF4 in the HCT116 PIK3CA mutant clone renders the cells less sensitive to glutamine deprivation. (F) Knockdown of ATF4 in the HCT116 PIK3CA mutant clone decreases transcription activity of a GPT2 promoter reporter. (G) Two putative ATF4 binding sites in the GPT2 promoter and mutant sequences that abolish ATF4 binding. (H) ATF4 binding site mutants reduces transcriptional activity of GPT2 promoter reporter. Data are presented as mean+SEM of three independent experiments. * $p<0.05$; *** $p<0.001$.

FIGS. 6(A-I) illustrate immunoblots, a schematic drawing, and graph showing he p110α-PDK1-RSK2 signaling axis regulates ATF4 protein stability. (A-B) ATF4 ubiquitnation levels are higher in the HCT116 WT clone than the mutant clone. Ubiquitination of endogenous ATF4 (A). Ubiquitination of ectopically expressed Flag-tagged ATF4 and HA-tagged ubiquitin (B). (C) Inhibitors of PI3K, PDK1 and RSK2 reduce ATF4 protein levels in the HCT116 mutant clone. (D) Schematics of the p110α signaling pathway that regulates ATF4 protein stability. (E) Overexpression of oncogenic p110α mutants in the HCT116 WT clone increases protein levels of ATF4 and GPT2. (F) Kinase-dead mutation on top of p110α E545K mutation reduces protein levels of ATF4 and GPT2 in the DLD1 PIK3CA mutant clone. (G) Kinase-dead mutation renders DLD1 PIK3CA mutant clone less sensitive to glutamine deprivation. Data are presented as mean+SEM of three independent cultures. ** $p<0.01$. (H) Knockdown of PDK1 by two independent siRNAs reduce ATF4 and GPT2 protein levels in the HCT116 PIK3CA mutant clone. (I) Knockdown of RSK2 by two independent siRNAs reduce ATF4 and GPT2 protein levels in the HCT116 PIK3CA mutant clone.

FIGS. 7(A-G) illustrate immunoblots showing phosphorylation of ATF4 S245 by RSK2 enhances its binding to USP8 and protects ATF4 from ubiquitin-mediated degradation. (A) Knockdown of RSK2 in the HCT116 PIK3CA mutant clone reduces pS245 ATF4. (B) Levels of pS245 ATF4 are higher in the HCT116 PIK3CA mutant clone than the WT clone. (C) The ATF4 S245A mutant is less stable than the WT protein. The indicated constructs were expressed in the HCT116 PIK3CA mutant clone and cell lysates were blotted with the indicated antibodies. (D) Ubiquitination levels of ATF4 S245A mutant are higher than that of WT protein. (E) The ATF4 S245A mutant binds to less USP8 than the WT protein. (F) Knockdown of USP8 in the HCT116 PIK3CA mutant clone reduces the ATF4 protein levels. (G) Knockdown of USP8 increases the levels of ATF4 ubiquitination.

FIGS. 8(A-D) illustrate graphs and schematic drawing showing metabolic profiling of PIK3CA WT and mutant clones. (A) [$^{13}C_5$-]Glutamine tracing of the TCA cycle intermediates in HCT116 WT and mutant (mut) clones. (B-C) Relative levels of ATP and NADH in the HCT116 WT and mutant clones with or without glutamine. (B) ATP; (C) NADH. (D) α-KG rescues the HCT116 mutant clone from cell death caused by glutamine (Gln) deprivation. Data are presented as mean+SEM of three independent cultures. * p<0.05; ** p<0.01.

FIGS. 9(A-C) illustrate graphs and an immunoblot showing aminooxyacetate (AOA) inhibits PIK3CA mutant tumor growth. (A) $IC_{50}$ of AOA in HCT116 and DLD1 PIK3CA WT and mutant clones. (B) Body weights of the mice with xenograft established from the indicated CRC cells before and after AOA treatment. N=5 mice in each group. (C) Western blot analyses of GPT2 protein levels in the indicated cell lines.

FIGS. 10(A-B) illustrate plots showing AOA synergizes with 5-FU to inhibit growth of HCT116 xenograft tumors.

FIGS. 11(A-C) illustrate plots and graph showing (A) enzyme kinetics of GPT2. Recombinant GPT2 was mixed with α-KG and alanine. The product pyruvate was detected by a colorimetric assay. (B) $IC_{50}$ of AOA to GPT2. (C) Relative amounts of α-KG. Xenograft tumors were treated with 10 mg/kg of AOA or vehicle. α-KG in a untreated tumor was set as 100%.

FIGS. 12(A-B) illustrate images and a plot showing the combination of CB-839 and 5-FU shrinks HCT116 xenograft tumors.

FIGS. 13(A-B) illustrate graphs showing PIK3CA mutations render cancer cells sensitive to EGCG and BPTES.

DETAILED DESCRIPTION

Figure 1:
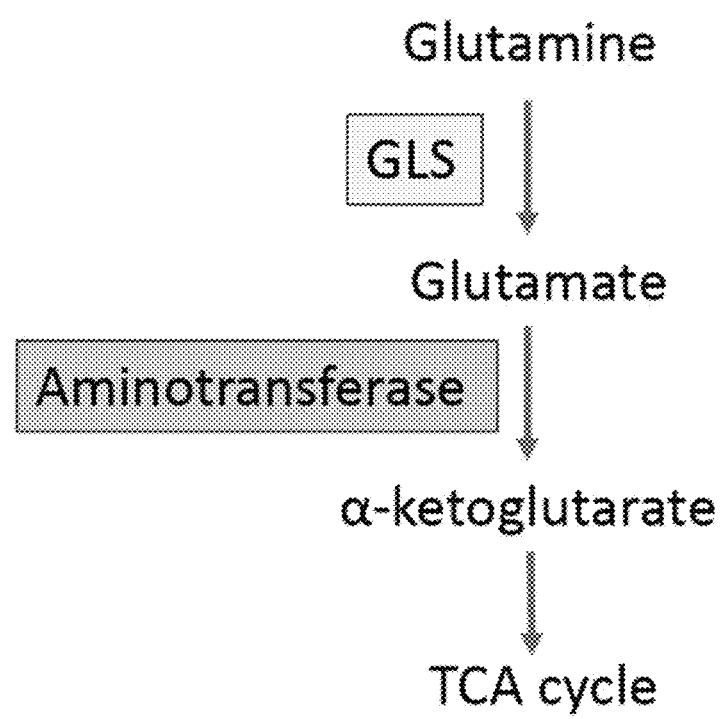
FIG. 1 is a schematic illustration of the initial steps of glutamine metabolism.

For convenience, certain terms employed in the specification, examples, and appended claims are collected here. Unless defined otherwise, all technical and scientific terms used herein have the same meaning as commonly understood by one of ordinary skill in the art to which this invention belongs.

As used in the specification and the appended claims, the singular forms "a," "an" and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

The term "agent" and "drug" are used herein to mean chemical compounds, mixtures of chemical compounds, biological macromolecules, or extracts made from biological materials, such as bacteria, plants, fungi, or animal particularly mammalian) cells or tissues that are suspected of having therapeutic properties. The agent or drug may be purified, substantially purified, or partially purified.

The term "biological sample" or "sample" as used herein includes any biological specimen obtained from a subject. Frequently, the sample will be a "clinical sample", i.e., a sample derived from a patient. Such samples include, but are not limited to, bodily fluids which may contain cancer cells, e.g., blood; tissue or fine needle biopsy samples, lung tissue; and archival samples with known diagnosis, treatment and/or outcome history. Biological samples may also include sections of tissues or cells, such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like. In some embodiments, the sample is whole blood or a fractional component thereof such as plasma, serum, or a cell pellet. In certain embodiments, the sample is obtained by isolating circulating cells of a solid tumor from a whole blood cell pellet using any technique known in the art. As used herein, the term "circulating cancer cells" comprises cells that have either metastasized or micro metastasized from a solid tumor and includes circulating tumor cells, and cancer stem cells. In other embodiments, the sample is a formalin fixed paraffin embedded (FFPE) tumor tissue sample, e.g., from a solid tumor.

The term "control sample" refers to one or more biological samples isolated from an individual or group of individuals that are normal (i.e., healthy).

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancer cells or benign cells or precancerous cells.

The term "decreased level of expression" as used herein, refers to a decrease in expression of a polynucleotide, e.g., gene, RNA, DNA, or protein at least 10% or more. For example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression" as used herein, refers to an increase in expression of a polynucleotide, e.g., gene, RNA, DNA, or protein at least 10% or more. For example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

The term "diagnosis" refers to a process aimed at determining if an individual is afflicted with a disease or ailment.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

The terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The terms "normal" and "healthy" are used herein interchangeably. They refer to an individual or group of individuals who have not shown to have cancer or tumors. In certain embodiments, normal individuals have similar sex, age, body mass index as compared with the individual from which the sample to be tested was obtained. The term "normal" is also used herein to qualify a sample isolated from a healthy individual.

The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

As used herein, the term "gene" or "recombinant gene" refers to a nucleic acid comprising an open reading frame encoding a polypeptide, including both exon and (optionally) intron sequences.

The term "genotype" as used herein includes to the genetic composition of an organism, including, for example, whether a diploid organism is heterozygous or homozygous for one or more variant PIK3CA alleles of interest.

The term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

The term "subject," "individual," and "patient" are used interchangeably herein to mean a human or other animal, such as farm animals or laboratory animals (e.g., guinea pig or mice) capable of having cell cycle (influenced) determined diseases, either naturally occurring or induced, including but not limited to cancer.

The term "sensitize" as used herein means to alter cancer cells or tumor cells in a way that allows for more effective treatment of the associated neoplastic disease with an antimetabolite agent, an anticancer agent, or radiation therapy. In some embodiments, normal cells are not affected to an extent that causes the normal cells to be unduly injured by the antimetabolite, chemotherapy, or radiation therapy.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site, and occurs in at least 1% of the population.

The term "synergistic effect" as used herein means the combined effect of two or more anticancer agents or chemotherapy drugs can be greater than the sum of the separate effects of the anticancer agents or chemotherapy drugs alone.

A "therapeutically effective amount" of a therapeutic agent is an amount that achieves the intended therapeutic effect of reducing cancerous cells, precancerous cells or benign tumor cells having a PIK3CA protein or gene mutation in a subject. The full therapeutic effect does not necessarily occur by administration of one dose and may occur only after administration of a series of doses. Thus, a therapeutically effective amount may be administered in one or more administrations.

A "prophylactically effective amount" of a therapeutic agent is an amount of a therapeutic agent that, when administered to a subject, will have the intended prophylactic effect, e.g., preventing or delaying the onset (or reoccurrence) of the disease or symptoms, or reducing the likelihood of the onset (or reoccurrence) of the disease or symptoms. The full prophylactic effect does not necessarily occur by administration of one dose and may occur only after administration of a series of doses. Thus, a prophylactically effective amount may be administered in one or more administrations.

An "effective amount" of a therapeutic agent is an amount that produces the desired effect.

"Treating" cancer in a patient refers to taking steps to obtain beneficial or desired results, including clinical results. For purposes of this invention, beneficial or desired clinical results include, but are not limited to alleviation or amelioration of one or more symptoms of the cancer; diminishing the extent of disease; delaying or slowing disease progression; amelioration and palliation or stabilization of the disease state.

The term "wild type" (wt) cell or cell line is used herein, for purposes of the specification and claims, to mean a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

Embodiments described herein relate to methods of determining the susceptibility, resistance, responsiveness, and/or sensitivity of a cancer, precancerous cells or a benign tumor in a subject to treatment with an inhibitor of one more enzymes of the glutamine metabolism pathway by determining the presence of a mutated PIK3CA gene or a mutant form of PIK3CA protein or a biologically active fragment thereof and/or the level of GPT2 expression in a sample of cancer cells, precancerous cells or benign tumor cells obtained from the subject. It was found that PIK3CA mutations reprogram glutamine metabolism in cancer cells by up-regulating glutamate pyruvate transaminase 2 (GPT2), thereby rendering them more dependent on glutamine. Compared to isogenic wild-type (WT) cells, PIK3CA mutant cancer cells convert substantially more glutamine to α-ketoglutarate in order to replenish the tricarboxylic acid (TCA) cycle and generate ATP. Mutant p110α up-regulates GPT2 gene expression through an AKT-independent PDK1-RSK2-ATF4 signaling axis. Moreover, inhibitors that target one or more glutamine metabolism enzymes, such as glutaminases or glutamate metabolism enzymes, including GPT2, can suppress tumor growth of cancer cells with PIK3CA mutations, but not cancer cells with WT PIK3CA.

Advantageously, the identification of cancer cells harboring PIK3CA mutations can be used as a predictive marker to determine the susceptibility, resistance, responsiveness, and/or sensitivity of the cancer cells to treatment with an inhibitor of one more enzymes of the glutamine metabolism pathway. Targeting one more enzymes of the glutamine metabolism pathway can thereby afford new therapies for the treatment of patients whose cancers harbor PIK3CA mutations.

In some embodiments, a method of determining susceptibility, resistance, responsiveness, and/or sensitivity to a cancer, precancerous cells, and/or benign tumor is a subject thereof to inhibitors of one or more enzymes of the glutamine metabolism pathway can include obtaining a sample of the cancer cells, the precancerous cells or the benign tumor cells from the subject, assaying the cells in the sample for the presence of a mutated PIK3CA gene or a mutant form of PIK3CA protein or a biologically active fragment thereof, and determining that the subject should be treated with the inhibitor if the cancer cells have the mutated PIK3CA gene or the mutant form of PIK3CA protein. In other embodiments, the method can include obtaining a sample of the cancer cells, the precancerous cells or the benign tumor cells from the subject, measuring the level of GPT2 expression in the cancer cells, comparing the measured level of GPT2 expression in the cancer cells to a control level, and identifying the cancer is more susceptible to treatment with the inhibitor if there is an increase in the measured levels of GPT2 expression in the cancer cells compared to a control level.

In some embodiments, the presence of mutated PIK3CA gene or a mutant form of PIK3CA protein and/or the level of GPT2 expression in the cancer cells of the subject can be determined by obtaining a sample of cancer cells from the subject diagnosed with cancer and determining the presence of mutated PIK3CA gene or a mutant form of PIK3CA protein and/or the level of GPT2 expression in the cancer cells. Cancer (and precancerous lesions) can include any tumor or cancerous cell that has a PIK3CA mutation. Such cancers include breast cancer, neuroblastoma, gastrointestinal carcinoma such as rectum carcinoma, colon carcinoma, familial adenomatous polyposis carcinoma and hereditary non-polyposis colorectal cancer, esophageal carcinoma, labial carcinoma, larygial carcinoma, hypopharyngial carcinoma, tongue carcinoma, salivary gland carcinoma, gastric carcinoma, medullary thyroid carcinoma, papillary thyroid carcinoma, renal carcinoma, kidney parenchymal carcinoma, ovarian carcinoma, cervical carcinoma, uterine corpus carcinoma, endometrium carcinoma, choriocarcinoma, pancreatic carcinoma, prostate carcinoma, testis carcinoma, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt's lymphoma, acute lymphocytic leukemia (ALL), chronic lymphocytic leukemia (CLL), acute myelologenous leukemia (AML), chronic myelologenous leukemia (CML), adult T-cell leukemia/lymphoma, hepatocellular carcinoma, gallbladder carcinoma, bronchial carcinoma, small cell lung carcinoma, non-small cell lung carcinoma, multiple myeloma, basal cell carcinoma, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma and plasmocytoma. Particular tumors include those of the brain, liver, kidney, bladder, breast, gastric, ovarian, colorectal, prostate, pancreatic, lung, vulval, thyroid, colorectal, oesophageal, sarcomas, glioblastomas, head and neck, leukemias and lymphoid malignancies. In some embodiments, the cancer can be selected from the group consisting of carcinomas, melanomas, sarcomas, lymphomas, leukemias, astrocytomas, gliomas, malignant melanomas, chronic lymphocytic leukemia, lung cancers, prostate cancer, colorectal cancers, ovarian cancers, pancreatic cancers, renal cancers, endometrial cancers, gastric cancers, liver cancers, head and neck cancers.

The samples used in the practice of the inventive methods may be fresh or frozen samples collected from a subject, or archival samples. Biological samples may be collected by any non-invasive means, such as, for example, by drawing blood from a subject, or using fine needle aspiration or needle biopsy. Alternatively, biological samples may be collected by an invasive method, including, for example, surgical biopsy.

In certain embodiments, the inventive methods are performed on the biological sample itself without or with limited processing of the sample.

In some embodiments, mutated PIK3CA genes or gene products and/or GPT2 expression levels can be detected in tumor samples or, in some types of cancer, in biological samples such as urine, stool, sputum or serum. For example, serum has been tested in the context of colorectal cancer. Cancer cells are found in blood and serum for cancers, such as lymphoma or leukemia. The same techniques discussed above for detection of mutant PIK3CA genes or gene products in tumor samples can be applied to other body samples. Cancer cells are sloughed off from tumors and appear in such body samples.

In other embodiments, the inventive methods are performed at the single cell level (e.g., isolation of cells from a biological sample). However, in such embodiments, the inventive methods are preferably performed using a sample comprising many cells, where the assay is "averaging" expression over the entire collection of cells present in the sample. Preferably, there is enough of the biological sample to accurately and reliably determine mutated PIK3CA genes or gene products and/or GPT2 expression levels. Multiple biological samples may be taken from the same tissue/body part in order to obtain a representative sampling of the tissue.

In still other embodiments, the mutated PIK3CA genes or gene products and/or GPT2 expression levels can be measured in a protein extract prepared from cancer cells of a biological sample. The protein extract can contain the total PIK3CA and/or GPT2 content by the cancer cell or cells. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from cells, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kits) most appropriate for a particular situation. After the protein extract has been obtained, the protein concentration of the extract can be standardized to a value being the same as that of the control sample in order to allow signals of the PIK3CA and/or GPT2 expression levels to be quantitated. Such standardization can be made using photometric or spectrometric methods or gel electrophoresis.

In yet other embodiments, mutated PIK3CA genes or gene products and/or GPT2 expression levels can be measured from nucleic acid molecules extracted from cancer cells of a biological sample. For example, RNA may be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from cells are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA, or using thermostable DNApolymerases (such as avian myeloblastosis virus reverse transcriptase or Moloney murine leukemia virus reverse transcriptase).

In general, mutated PIK3CA genes or gene products and/or GPT2 expression levels in the cancer cells can be determined by contacting cancer cells in a biological sample isolated from a subject with binding agents for PIK3CA and/or GPT2; detecting, in the sample, the presence or levels of the mutated PIK3CA genes or gene products and/or GPT2 that bind to the binding agents; and optionally, comparing the detected mutated PIK3CA genes or gene products and/or GPT2 expression levels in the sample with the levels of mutated PIK3CA genes or gene products and/or GPT2 in a control sample. As used herein, the term "binding agent" refers to an entity, such as a polypeptide or antibody that specifically binds to mutated PIK3CA genes or gene products and/or GPT2. An entity "specifically binds" to mutated PIK3CA genes or gene products and/or GPT2 if it reacts/interacts at a detectable level with mutated PIK3CA genes or gene products and/or GPT2 but does not react/interact detectably with polynucleotides and/or peptides containing unrelated sequences or sequences of different polypeptides.

In certain embodiments, the binding agent is an RNA molecule, or a polypeptide (e.g., a polypeptide that comprises a polypeptide sequence of a protein marker, a peptide variant thereof, or a non-peptide mimetic of such a sequence).

In other embodiments, the binding agent is an antibody specific for mutated PIK3CA and/or GPT2. Antibodies for use in the methods include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration.

Instead of being prepared, antibodies to be used in the methods described herein may be obtained from scientific or commercial sources.

In certain embodiments, the binding agent is directly or indirectly labeled with a detectable moiety. The role of a detectable agent is to facilitate the measuring of the mutated PIK3CA genes or gene products and/or GPT2 expression levels by allowing visualization of the complex formed by binding of the binding agent to mutated PIK3CA genes or gene products and/or GPT2 expression levels (or analog or fragment thereof). The detectable agent can be selected such that it generates a signal which can be measured and whose intensity is related (preferably proportional) to the presence and/or amount of mutated PIK3CA genes or gene products and/or GPT2 expression levels present in the sample being analyzed. Methods for labeling biological molecules such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the methods described herein. Detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Mutated PIK3CA and/or GPT2 expression levels in the methods described herein may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the mutated PIK3CA and/or GPT2 will depend on the nature of the assay and of the detectable moiety (e.g., fluorescent moiety).

Alternatively, mutated PIK3CA and/or GPT2 expression levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (I) separation of individual proteins in a sample by electrophoresis (2-D PAGE), (2) identification of individual proteins recovered from the gel (e.g., by mass spectrometry or N-terminal sequencing), and (3) analysis of the data using bioinformatics.

As already mentioned above, the methods described herein may involve determination of the expression levels of a set of nucleic acid molecules comprising polynucleotide sequences coding for mutated PIK3CA genes or gene products and/or GPT2. Determination of the presence and/or expression levels of nucleic acid molecules in the practice of the inventive methods may be performed by any method, including, but not limited to, Southern analysis, Northern analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Probes may be based on nucleic acid sequences encoding at least 5 sequential amino acids from regions of nucleic acids encoding mutated PIK3CA genes or gene products and/or GPT2, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding mutated PIK3CA genes or gene products and/or GPT2. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for mutated PIK3CA genes or gene products and/or GPT2 may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Primer sequences and amplification protocols for evaluating PIK3CA mutations are known to those in the art and have been published. Examples include Karakas, et al., Mutation of the PIK3CA Oncogene in Human Cancers, BRITISH J CANCER 94(4):455-459 (2006); Li et al., Mutations of PIK3CA in Gastric Adenocarcinoma, BIOMED CENTRAL CANCER 5:29 (2005); Qiu et al., PIK3CA Mutations in Head and Neck Squamous Cell Carcinoma, CLIN CANCER RES. 12(5):1441-1446 (2006). The most frequent PIK3CA mutations are E542K (Glu524Lys), E545K (Glu545Lys), and E545D (Glu545Asp) mutations in exon 9 and H1047R (His1047Arg) mutations in exon 20.

Hybridization and amplification techniques described herein may be used to assay qualitative and quantitative aspects of expression of nucleic acid molecules comprising polynucleotide sequences coding for the inventive gene or protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; 1.1. Chen et al., Genomics, 1998, 51: 313324; U.S. Pat. Nos. 5,143,854; 5,445,934; 5,807,522; 5,837,832; 6,040,138; 6,045,996; 6,284,460; and 6,607,885).

In some embodiments, a mutation in the PIK3CA gene in a sample can be detected by amplifying nucleic acid corresponding to the PIK3CA gene obtained from the sample, or a biologically active fragment, and comparing the electrophoretic mobility of the amplified nucleic acid to the electrophoretic mobility of corresponding wild-type PIK3CA gene or fragment thereof. A difference in the mobility indicates the presence of a mutation in the amplified nucleic acid sequence. Electrophoretic mobility may be determined on polyacrylamide gel. Alternatively, an amplified PIK3CA gene or fragment nucleic acid may be analyzed for detection of mutations using Enzymatic Mutation Detection (EMD) (Del Tito et al, Clinical Chemistry 44:731-739, 1998). EMD uses the bacteriophage resolvase $T_4$ endonuclease VII, which scans along double-stranded DNA until it detects and cleaves structural distortions caused by base pair mismatches resulting from point mutations, insertions and deletions. Detection of two short fragments formed by resolvase cleavage, for example by gel eletrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed.

In other embodiments, the ligase chain reaction, which is known in the art, can also be used to amplify PIK3CA sequences. In addition, a technique known as allele specific PCR can be used. According to this technique, primers are used which hybridize at their 3' ends to a particular PIK3CA mutation. If the particular PIK3CA mutation is not present, an amplification product is not observed. Amplification Refractory Mutation System (ARMS) can also be used as disclosed in European Patent Application Publication No. 0332435 and in Newton et al., Nucleic Acids Research, Vol. 17, p. 7, 1989. Insertions and deletions of genes can also be detected by cloning, sequencing and amplification. In addition, restriction fragment length polymorphism, (RFLP) probes for the gene or surrounding marker genes can be used to score alteration of an allele or an insertion in a polymorphic fragment. Single stranded conformation polymorphism (SSCP) analysis can also be used to detect base change variants of an allele. (Orita et al., Proc. Natl. Acad. Sci. USA Vol. 86, pp. 2766-2770, 1989, and Genomics, Vol. 5, pp. 874-879, 1989). Other techniques for detecting insertions and deletions as are known in the art can be used.

Mismatches can include hybridized nucleic acid duplexes which are not 100% complementary. The lack of total complementarity may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. A labeled riboprobe which is complementary to the human wild-type PIK3CA gene coding sequence can also be used. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the PIK3CA mRNA or gene. If the riboprobe comprises only a segment of the PIK3CA mRNA or gene it will be desirable to use a number of these probes to screen the whole mRNA sequence for mismatches.

In a similar manner, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR before hybridization. Changes in DNA of the PIK3CA gene can also be detected using Southern hybridization, especially if the changes are gross rearrangements, such as deletions and insertions.

Once the mutated PIK3CA genes or gene products and/or GPT2 expression levels in the cancer cells has been measured or determined (as described above), the measured mutated PIK3CA genes or gene products and/or GPT2 expression levels can optionally be compared to a control level. The control level can be based upon the level of mutated PIK3CA and/or GPT2 in a normal cell obtained from a control population (e.g., the general population) or a select population of subjects. For example, the select population may be comprised of apparently healthy subjects or from subjects at risk of developing cancer.

The control level can be related to the value used to characterize the level of mutated PIK3CA and/or GPT2 expression levels obtained from the subject. The control level can also take a variety of forms. For example, the control level can be a single cut-off value, such as a median or mean. The control level can be established based upon comparative groups, such as where the level in one defined group is double the level of another defined group.

Control levels of mutated PIK3CA and/or GPT2 expression in cells, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.).

Depending upon the level or value of measured mutated PIK3CA and/or GPT2 when compared to the control level, a determination can be made as to whether the cancer cells or cancer of the subject is more or less susceptible, sensitive, and/or resistance to treatment with an inhibitor of one or more enzymes of the glutamine metabolism pathway. In some embodiments, a determined presence of a mutated PIK3CA gene or a mutant form of PIK3CA protein or a biologically active fragment thereof for the cancer identifies the cancer as being more susceptible to treatment with the inhibitor of one or more enzymes of the glutamine metabolism pathway. An absence of a mutated PIK3CA gene or a mutant form of PIK3CA protein or a biologically active fragment thereof for the cancer identifies the cancer as being less susceptible to treatment with the inhibitor of one or more enzymes of the glutamine metabolism pathway. In other embodiments, a GPT2 expression level higher or increased compared to the control level identifies the cancer as being more susceptible to treatment with the inhibitor of one or more enzymes of the glutamine metabolism pathway. In contrast, a measured or determined expression level of GPT2 expression less than the control level identifies the cancer as being less susceptible to treatment with the inhibitor of one or more enzymes of the glutamine metabolism pathway.

By determining the efficacy of the inhibitor of one or more enzymes of the glutamine metabolism pathway, such as inhibitors of glutaminase and/or inhibitors of aminotransferase (e.g., glutamate pyruvate transaminase, aspirate aminotransferase, and glutamate dehydrogenase), to treating cancer and/or susceptibility, sensitivity, responsiveness, and/or resistance of the cancer cell to the inhibitor, skilled physicians may select and prescribe treatments adapted to each individual patient with increased efficiency. In some embodiments, a method of treating cancer with the inhibitors described herein, such as glutaminase inhibitors and/or aminotransferase inhibitors, can include first determining the presence of mutated PIK3CA genes or gene products and/or GPT2 expression levels of cancer cells of a subject diagnosed with cancer and then administering an inhibitor of one more enzymes of the glutamine metabolism pathway, depending on the determined or measured presence of mutated PIK3CA genes or gene products and/or GPT2 expression levels.

In some embodiments, an inhibitor of one or more enzymes of the glutamine metabolism pathway can be a glutaminase inhibitor and/or aminotransferase inhibitor. Examples of glutaminase inhibitors can include heterocyclic inhibitors of glutaminase having formula I disclosed in U.S. Pat. No. 8,604,016, and U.S. Patent Application Publication Nos. 2014/0050699A1 and 2015/0004134, which are herein incorporated by reference in their entirety. Heterocyclic inhibitors of glutaminase having formula I disclosed in U.S. Pat. No. 8,604,016 can include of the compounds disclosed in Table 3 of the application. In some embodiments, the glutaminase inhibitor can include CB-839 or a pharmaceutically acceptable salt thereof. In other embodiments, the glutaminase inhibitor has the formula:

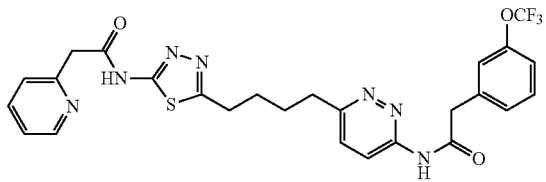 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof.

Other examples of glutaminase inhibitors include bis-2-(5-phenylacetamido-1,2,4-thiadiazol-2-yl)ethyl sulfide (BPTES) and analogs thereof; N-(5-{2-[2-(5-amino-[1,2,4] thiadiazol-2-yl)-ethylsulfanyl]-ethyl}-[1,3,4]-thiadiazol-2-yl)-2-phenyl-acetamide; small molecule 968 and derivatives thereof 6-diazo-5-oxo-L-norleucine (DON); N-ethylmaleimide (NEM); p-chloromercuriphenylsulfonate (pCMPS); L-2-amino-4-oxo-5-chloropentoic acid; DON plus o-carbamoyl-L-serine; acivicin [(alphaS,5S)-alpha-amino-3-chloro-4,5-dihydro-5-isoxazoleacetic acid]; azaserine; and 5-β-bromo-4-(dimethylamino)phenyl)-2,2-dimethyl-2,3,5, 6-tetrahydrobenzo[-a]phenanthridin-4(1H)-one Still other examples of glutaminase inhibitors include imidazole derivatives having formula I disclosed in U.S. Pat. No. 5,552,427, which is herein incorporated by reference in its entirety.

In some embodiments, the aminotransferase inhibitor can be a selective or partially glutamate pyruvate transanimase (GPT) or an alanine aminotransferase inhibitor. An example of alanine aminotransferase inhibitor is aminooxyacetate. Aminooxyacetate inhibits enzymatic activity of amino transaminases including GPT2. Other examples of aminotransferase inhibitors, such as GPT2 inhibitors, include L-cycloserine and β-chloro-L-alanine.

In some embodiments, the glutaminase inhibitor and/or the aminotransferase inhibitor can be administered to subject having cancer, precancerous cells or a benign tumor with mutated PIK3CA genes or gene products and/or elevated GPT2 expression levels at therapeutically effective amounts. The therapeutically effective can be an amount effective to substantially inhibit glutamine metabolism in the cancer cells and/or suppress cancer cell growth and/or proliferation.

The inhibitors of one or more enzymes of the glutamine metabolism pathway, including glutaminase inhibitors and/or the aminotransferase inhibitors, can be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. In some embodiments a slow release preparation comprising the therapeutic agents is administered. The inhibitors of one or more enzymes of the glutamine metabolism pathway can be administered as a single treatment or in a series of treatments that continue as needed and for a duration of time that causes one or more symptoms of the cancer to be reduced or ameliorated, or that achieves another desired effect.

The dose(s) vary, for example, depending upon the identity, size, and condition of the subject, further depending upon the route by which the composition is to be administered and the desired effect. Appropriate doses of a therapeutic agent depend upon the potency with respect to the expression or activity to be modulated. The therapeutic agents can be administered to an animal (e.g., a human) at a relatively low dose at first, with the dose subsequently increased until an appropriate response is obtained.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively, dosages may be based and calculated upon the surface area of the patient, as understood by those of skill in the art.

In some embodiments, the inhibitors of one or more enzymes of the glutamine metabolism pathway can be used in combination and adjunctive therapies for inhibiting proliferation and/or growth of cancer cells having mutated PIK3CA. The phrase "combination therapy" embraces the administration of the inhibitors described herein and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of the present invention.

A combination therapy is intended to embrace administration of the therapeutic agents (e.g., inhibitors described herein and/or other therapeutic agents) in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents described herein in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments the inhibitors of one or more enzymes of the glutamine metabolism pathway can be administered in combination at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophyllotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

In some embodiments, chemotherapeutic agents that may be administered in combination with the inhibitors described herein can include: ABT-263, aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil and 5-fluorouracil, fluoxymesterone, flutamide, gemcitabine, genistein, goserelin, hydroxyurea, idarubicin, ifosfamide, imatinib, interferon, irinotecan, ironotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, PF-04691502, plicamycin, pomalidomide, porfimer, procarbazine, raltitrexed, rituximab, romidepsin, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, vinorelbine, and vorinostat (SAHA). For example, chemotherapeutic agents that may be conjointly administered with compounds of the invention include: aminoglutethimide, amsacrine, anastrozole, asparaginase, bcg, bicalutamide, bleomycin, bortezomib, buserelin, busulfan, campothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, pomalidomide, porfimer, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, and vinorelbine. In other embodiments, chemotherapeutic agents that may be conjointly administered with compounds of the invention include: ABT-263, dexamethasone, 5-fluorouracil, PF-04691502, romidepsin, and vorinostat (SAHA).

It will be appreciated that pharmaceutical compositions or formulations of the inhibitors and/or other therapeutic agents described herein can be provided in any form, which allows for the composition to be administered to a patient. For example, the composition may be in the form of a solid, liquid or gas (e.g., aerosol). Other routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

Pharmaceutical compositions can include physiologically acceptable surface active agents, carriers, diluents, excipients, smoothing agents, suspension agents, film forming substances, and coating assistants, or a combination thereof; and a inhibitor and/or other therapeutic agent disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions for use herein may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical compositions for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils, such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the inhibitors and/or other therapeutic agents can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, pharmaceutical compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Additional therapeutic or diagnostic agents may be incorporated into the pharmaceutical compositions. Alternatively or additionally, pharmaceutical compositions may be combined with other compositions that contain other therapeutic or diagnostic agents.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Example

In this Example we show that PIK3CA mutations render cancers, such as colorectal cancers (CRC), more sensitive to glutamine deprivation by up-regulation of glutamate pyruvate transaminase 2 (GPT2), an enzyme involved in glutamine metabolism. We further show that mutant p110α increases GPT2 gene expression through an AKT-independent signaling pathway. Moreover, we show that aminooxyacetate (AOA), and EGCG, compounds that inhibit enzymatic activity of antitransferases, as well as BPTES and CB-839, compounds that inhibit enzymatic activity of glutaminose, can suppress xenograft tumor growth of CRCs with PIK3CA mutations, but not CRCs with wildtype (WT) PIK3CA. These results demonstrate that reprogramming glutamine metabolism is crucial for the oncogenic function of PIK3CA mutations and that targeting glutamine metabolism can be an effective approach to treating cancer patients harboring mutations of this gene.

Methods

Cell Culture

Colorectal cancer (CRC) cell lines, HCT116, DLD1, RKO, HT29, SW480 and LOVO, were cultured in Mccoy's 5A medium containing 10% fetal bovine serum (FBS) as described previously. Mccoy's 5A (Cat No. SH30200), fetal bovine serum (Cat No. SH30910), and Glutamine-free DMEM (with 4.5 g/L glucose, without pyruvate, Cat No. SH30081) were obtained from Hyclone. Dialysed FBS (dFBS, Cat No. 26400) and Glutamine, Glucose free DMEM (Cat No. A14430) were obtained from Gibco (Invitrogen).

Chemicals, siRNAs, Plasmids and Antibodies

L-Glutamine, L-Glutamine-$_{13}C_5$, D-Glucose, dimethyl α-Ketoglutarate, and Aminooxyacetate (AOA) were purchased from Sigma. siRNAs of ATF4 (SI03019345, SI04236337) and PDK1 (SI00301140, SI00301154) were purchased from Qiagen. siRNAs of RSK2 (J-003026-10, J-003026-12) were purchased from Dharmacon. siRNAs of USP8 (SR306014A, SR306014B) were purchased from Origene. shRNAs of GPT2 (TRCN0000035025, TRCN0000035026) were purchased from Sigma. Adeno-ATF4 virus was made as described in. cDNAs of GPT2, ATF4 and β-TrCP were purchased from Addgene. GPT2 ORF was subcloned into pCMV-3Tag1A vector with HindIII and SalI. Then Flag-GPT2 sequence was PCR out and subcloned into pCDNA3.1zeo with KpnI and XbaI. Flag tagged ATF4 expression vector was constructed by subcloning ATF4 ORF into the pCMV-3Tag1A vector with BamHI and XhoI. ATF4 S219A and S245A mutant constructs were made by Quick-change Site-Directed Mutagenesis kit (Agilent Technologies). Plasmids were transfect into cells with Lipofectamine 3000 (Invitrogen) according to manufacturer instruction. For transient expression, cells were lysed 72 hours after transfection. For stable expression (FLAG-GPT2 expression), cells were selected with 0.5 mg/ml Zeocin (Invitrogen) for 7 days. All primers and antibodies used in this Example are listed in Tables 1 and 2.

TABLE 1

Primers used

| Targeting primers | |
|---|---|
| Left Arm forward | GGGAAAG/ideoxyU/GATGAGTCTGTCGGTGTTTGTG |
| D933A reverse | AAAGCTATATGAAACAGCTTTCAAA |
| D933A forward | TTTGAAAGCTGTTTCATATAGCTTTTGGACACTTTTTGGATC |

TABLE 1-continued

Primers used

| | | |
|---|---|---|
| Left Arm reverse | | GGAGACA/ideoxyU/TTTTGTGTTTTTAATTGCTCGAGC |
| p110α D933A Right Arm forward | | GGTCCCA/ideoxyU/CTGGCTGCTCTATTAGAAACAATC |
| Knock-In vector | Right Arm reverse | GGCATAG/ideoxyU/GATGTTGACATGGATGTGGTGA |
| Screening forward | | CTGCAGTTCAACAGCCACAC |
| Screening reverse | | CAGGGAAATGCAAATTAAAACC |
| Cre forward | | GTAAAGGAGCCCAAGAATGC |
| Cre reverse | | GCCAACATTTATTATTTTGAAATTG |

Subcloning primers

| | | |
|---|---|---|
| GPT2 | Forward | CCCAAGCTTATGCAGCGGGCGGCGGCGC |
| pCMV-3Tag1A | Reverse | ACGCGTCGACTCACGCGTACTTCTCCAGGAAG |
| Flag-GPT2 | Forward | CGGGGTACCGCCACCATGGATTACAAGGATGACGACG |
| pCDNA3.1zeo | Reverse | TGCTCTAGATCACGCGTACTTCTCCAGGAAG |
| FLAG-ATF4 | Forward | CGCGGATCCATGACCGAAATGAGCTTCCTGAG |
| pCMV-3Tag1A | Reverse | CCGCTCGAGCTAGGGGACCCTTTTCTTCC |
| Myc-β-TrCP | Forward | GGTCCCA/ideoxyU/TGGACCCGGCCGAGGCGGTG |
| pCMV-Tag2 | Reverse | GGCATAG/ideoxyU/TCTGGAGATGTAGGTGTATG |
| GPT2 promoter | Forward | CGGGGTACCCTGGGGAAGACTTTTACCTA |
| pGL3 | Reverse | GGAAGATCTCCACAGCCGCATCCCCGCGC |

Mutagenesis primers

| | | |
|---|---|---|
| FLAG-ATF4 S219A | Forward | CTTCAGATAATGATGCTGGCATCTGTATGAGC |
| | Reverse | GCTCATACAGATGCCAGCATCATTATCTGAAG |
| FLAG-ATF4 S245A | Forward | CAGGGGCTCTCCAAATAGGGCGCTCCCATCTCCAGGTGTTC |
| | Reverse | GAACACCTGGAGATGGGAGCGCCCTATTTGGAGAGCCCCTG |
| GPT2 promoter Mut1 | Forward | CGGAAGTGATGGAGGTCGTTGCGCTAATGGAGTGGTCGGGAAAAC |
| | Reverse | GTTTTCCCGACCACTCCATTAGCGCAACGACCTCCATCACTTCCG |
| GPT2 promoter Mut2 | Forward | GCACCGTGTGGCCTTGGAGTTGCGCTACTCGGGGCGATGACTGCAC |
| | Reverse | GTGCAGTCATCGCCCCGAGTAGCGCAACTCCAAGGCCACACGGTGC |

RT-PCR primers

| | | |
|---|---|---|
| SLC1A5 | Forward | CATCATCCTCGAAGCAGTCA |
| | Reverse | CTCCGTACGGTCCACGTAAT |
| GLS1 | Forward | TGCATTCCTGTGGCATGTAT |
| | Reverse | TTGCCCATCTTATCCAGAGG |

TABLE 1-continued

Primers used

| Gene | Direction | Sequence |
|---|---|---|
| GLS2 | Forward | GACTTCTCAGGGCAGTTTGC |
|  | Reverse | TGGTTGAACTGCACAGCATC |
| GPT1 | Forward | ATGGCCTCGAGCACAGGTGAC |
|  | Reverse | CAGCACCGTCACGATGGCATC |
| GPT2 | Forward | CTTTCTCCTGGCTGATGAGG |
|  | Reverse | TAACCACACTCGCCCATGTA |
| GOT1 | Forward | ACCTGGGAGAATCACAATGC |
|  | Reverse | GCGGCTGTGCCCGCCGGTGC |
| GOT2 | Forward | CAATGGCTGCAAGAAGTGAA |
|  | Reverse | GGCTTTAGCCCTGTGAAACA |
| GLUD1 | Forward | CACACGCCTGTGTTACTGGT |
|  | Reverse | CTCCAAACCCTGGTGTCATT |
| GAPDH | Forward | GGAAATCCCATCACCATCT |
|  | Reverse | TGTCGCTGTTGAAGTCAGA |
| ATF4 | Forward | CCAACAACAGCAAGGAGGAT |
|  | Reverse | AGTGTCATCCAACGTGGTCA |

TABLE 2

Antibodies

| Antibodies | Application | Company | Catalog number |
|---|---|---|---|
| GPT2 | IB | Proteintech Group | 16757-1-AP |
| GLS1 | IB | Proteintech Group | 20170-1-AP |
| ATF4 | IB, IP | Santa Cruz | sc-200 |
| HA | IB | Santa Cruz | sc-805 |
| GAPDH | IB | Santa Cruz | sc-25778 |
| c-myc | IB | Santa Cruz | sc-40 |
| PUMA | IB | Cell Signaling | 4976S |
| p-Foxo | IB | Cell Signaling | 9464S |
| RSK2 | IB | Cell Signaling | 5528S |
| p-eIF2α | IB | Cell Signaling | 3398S |
| eIF2α | IB | Cell Signaling | 9722 |
| Ubiquitin | IB | Cell Signaling | 3936 |
| USP8 | IB | Cell Signaling | 8728 |
| USP7 | IB | Cell Signaling | 4833 |
| USP1 | IB | Cell Signaling | 8033 |
| USP2 | IB | Cell Signaling | 8036 |
| USP9X | IB | Cell Signaling | 5751 |
| USP10 | IB | Cell Signaling | 8501 |
| USP14 | IB | Cell Signaling | 8159 |
| USP18 | IB | Cell Signaling | 4813 |
| Cleaved PARP | IB | Cell Signaling | 9544 |
| Cleaved Caspase3 | IB | Cell Signaling | 9664 |
| Foxo1 | IB | Millipore | 05-1075 |
| pATF4 S245 | IB | Abcam | ab28830 |
| PDK1 | IB | Abcam | ab52893 |
| FLAG | IB | Sigma | F1804 |

Quantitative Real Time PCR

One µg of total RNA was used for Reverse transcription by Superscript First-Strand kit (Invitrogen). cDNA was used for real time PCR. Taqman assay system was used for qRT-PCR using GPT2 (Hs00370287, Applied biosystems) probes with IQ super mix (170-8860, Bio-Rad). Expression levels of GPT2 in each tumor were normalized to that of B2M. Mutation status of the human CRC specimens are listed in Table 3.

TABLE 3

Tumor Samples of Quantitative Real-Time PCR

| Tumors | PIK3CA mutation | Tumors | Mutation in PI3K pathway |
|---|---|---|---|
| 435X | PIK3CA E545K | 560X | WT |
| 507X | PIK3CA E545K | 569X | WT |
| 533X | PIK3CA H1047R | 492X | WT |
| 511X | PIK3CA Q546K | 452X | WT |
| 587X | PIK3CA H1047R | 493X | WT |
| 480X | PIK3CA R38C | 566X | WT |
| 579X | PIK3CA H1047R | 586X | WT |
| 823X | PIK3CA H1047R | 559X | WT |
| X841 | PIK3CA H1047R | 464X | WT |
| X850 | PIK3CA E542K | 502X | WT |

Somatic Gene Targeting

The PIK3CA D933A targeting vector was constructed with USER system, and targeted cells were generated as described previously. Briefly, vector arms were created by PCR from genomic DNA using HiFi Taq (Invitrogen) and validated by sequencing prior to viral production and infection. DLD1 Mutant cells were infected with rAAV viruses. Stable G418-resistent clones were then selected for PCR screening as reported. Targeted clones were genotyped by RTPCR and sequencing. Detailed information on construction of targeting vectors and targeted cells is available upon request.

Immunoblotting and Immunoprecipitation

Cells were lysed in RIPA buffer [10 mM Tris (pH 7.4), 150 mM NaCl, 5 mM EDTA (pH 8.0), 0.1% SDS, 1% Triton-X100, 1 mM DTT, 1 mM PMSF, complete Protease Inhibitor Cocktail tablet (Roche); supplemented with phosphatase inhibitors (1 mM Na$_3$VO$_4$, 50 mM NaF, 1 mM β-glycerophosphate, 20 mM sodium pyrophosphate)]. Lysates were then cleared by centrifugation at 14,000 rpm for 10 min and protein concentration in supernatants was determined by the BCA protein assay kit (Pierce). Equal amounts of total protein were used for immunoblotting. For immunoprecipitation (IP), cells were lysed as mentioned above. Cleaned cell lysate incubated with antibody for one hour, and then protein A and/or protein G for one hour. Protein A/G beads were washed with lysis buffer three times, and then boiled with SDS-loading buffer followed with immunoblotting.

Luciferase Reporter Assay

A 1.5 kb promoter region of GPT2 was subcloned into pGL3 vector (Promega) to obtain pGL3-GPT2 promoter-LUC plasmid. pGL3-GPT2 promoter-LUC was co-transfect with pCMV-ATF4 and internal control β-galactosidase expressing pCH110 (abbreviation as pCH110 β-gal) or Renilla luciferase expressing pRL (Promega). 48 hours after transfection, cells were harvest for Luciferase assay according to manufacturer instruction (Promega). Luminescence was measured with EnVision 2103 Multilabel Plate Readers (PerkinElmer). β-galactosidase activity was measured with β-Gal assay kit (Invitrogen). Mutation of GPT2 promoter was generated with Quickchange kit (Agilent Technologies) and primers is in Table 2. The uORFATF4 plasmid is a kind gift from Dr. Ron Wek at Indiana University.

Cell Proliferation Assay

Cells were plated in 96-well plates at 2000 cells per well, 24-well plates at $1 \times 10_4$ cells per well, 6-well plates at $2 \times 10^5$ cells per well in complete DMEM [20 mM Glucose, 2 mM Glutamine, 10% dialysed fetal bovine serum (dFBS), Invitrogen]. After 24 hours, cells were washed with PBS, and changed to either glutamine deprived DMEM (with 20 mM Glucose) or glucose deprived DMEM (with 2 mM Glutamine) containing 10% dFBS. Cells (including floating cells in medium) were collected and counted by Trypan-Blue exclusive assay.

Flow Cytometry

Cells were fixed with methanol and then incubated at 37° C. for 30 min in 5% normal goat serum diluted in PBS. Propidium iodide (PI) solution was used to stain cells at 4° C. for 1 hour. Cells were analyzed on an Epics XL flow cytometer. WinMDI2.9 was used for data analysis. Cell debris and aggregates were excluded on PI gating. Percentages of sub-G1, G1, S and G2/M populations were determined by histograms generated by WinDI2.9.

Gene Silencing

Plasmids expressing shRNAs were transfect into cells. Two days post-transfection, cells were selected with 1 μg/ml of puromycin for 7 days. Puromycin resistance cells were collected, amplified, and analyzed. For genes silenced by siRNAs, siRNAs were transfect into cells with Lipofectamine 3000. Three days post-transfection, cells were harvested for further analyses.

Ubiquitination Assay

Cells were pre-treated with 5 μM of MG132 for 6 hours and cell lysates were immunoprecipitated with antibodies against either ATF4 or FLAG. Beads were washed with washing buffer [10 mM Tris (pH 7.4), 1 M NaCl, 1 mM EDTA (pH 8.0), 1% NP-40] for 3 times. The immunocomplexes were resolved in SDS-PAGE gels for Western blot analyses.

Polysome Profile Analysis

Three tumors (~250 mm3 size) of each genotype were snap-frozen in liquid nitrogen, pulverized and lysed in 1000 μl of lysis buffer (50 mM HEPES-KOH (pH 7.4), 5 mMMgCl2, 250 mMKCl, 2% TritonX-100, 8.5% sucrose, 100 μg/ml cycloheximide, 1 mM DTT, 200 units/ml RNase inhibitor (RNaseOUT, Invitrogen), EDTA-free protease inhibitor (Roche Applied Science) and 10 mM ribonucleoside vanadyl complex (New England Biolabs)), kept on ice for 20 min, and then passed 15 times through a 23-gauge needle. Lysates were spun at 14,000 rpm for 15 min, and supernatants were collected. Approximately 10-15 A units (260 nm) of lysates were layered over 10-50% cold sucrose gradients in buffer (50 mM HEPES-KOH (pH 7.4), 5 mM MgCl2, 250 mM KCl). Gradients were centrifuged at 17,000 rpm in a BeckmanSW28 rotor for 15 h at 4° C. After centrifugation, 12 fractions (1.2 ml/fraction) were collected. RNA from each fraction was isolated using TRIzol LS reagent (Invitrogen), and an equal volume of RNA from each fraction was used for cDNA synthesis. The relative quantities of specific mRNAs were measured by quantitative RT-PCR (RT-qPCR).

Xenograft Study

Animal experiments were approved by the Case Western Reserve University Animal Care and Use Committee. As described in, 3 million cells were injected subcutaneously into the flanks of 4 to 6-week-old female athymic nude mice. Mice were randomly assigned into treatment groups (5 mice/group). When average tumor volume reached 100 mm3, mice were treated with vehicle control, 5 mg/kg or 10 mg/kg of AOA every day per IP (intraperitoneal) injection. Tumor volumes were measured with an electronic caliper and calculated as length×width$^2$/2.

Metabolic Assays and Stable Isotope Tracing

A million cells were plated in each T25 flask. When reached at 70% confluency, cells were washed with PBS twice and changed to medium containing 2 mM of [$^{13}C_5$-] Glutamine. Cells were grown in medium for either 2 hours for enrichment assay or 24 hours for relative abundance assay. Cells were then quenched and harvested with 1 ml pre-chilled (−80° C.) methanol. Five μM of heptadecanoic acid, 2.5 μM of [3,3,4,5,5,5$^{-2}$H6]4-hydroxypentanoate and 2.5 μM of [2,2,3,3,4,4,5,5,6,6,7,7,7$^{-2}$H13]heptanoate were added as internal standards. Metabolites were extracted by homogenization and sonication on ice. Cell debris was discarded by centrifuge at 14,000 rpm, 15 mins at 4° C. The supernatant was dried with nitrogen gas. TBDMS (MTB-STFA+TBDMCS, REGIS Technologies): Acetonitrile (2:1) was used for derivatization of metabolites at 60° C. for 1 hour. Samples (1 μl) were injected into GC-MS (Agilent Technologies) for metabolite profiling. For enrichment analyses, total pool of each metabolite was considered as 100%. M (0, 1, 2, 3, ect.) indicated the number of $^{13}$C labelled carbon. Enrichment indicates percentage of each isotopomer to total pool. For relative abundance analyses, each $^{13}$C labelled isotopomer or non-labelled metabolite was normalized to an internal standard with same response time range in GC-MS.

Assays of ATP/ADP and NADH/NAD

The amounts of ATP and ATP/ADP ratios were measured with an ADP/ATP ratio assay kit (Abcam) according to the manufacturer's instructions. The amounts of ATP were determined by an ATP standard curve, and normalized to the protein concentrations. The amounts of NADH and NADH/NAD ratios were measured with a NAD/NADH quantitation colorimetric kit (BioVision). The NADH concentrations were determined by a NADH standard curve, and normalized to the protein concentrations.

Results

PIK3CA Mutations Render CRC Cells Dependent on Glutamine

Most PIK3CA mutations are clustered in two hot spots: H1047R in the kinase domain and E545K in the helical domain. We set out to determine whether PIK3CA mutations reprogram cell metabolism in CRCs. The CRC cell line HCT116 harbors a heterozygous H1047R mutation, whereas DLD1 CRC cells express a heterozygous E545K mutation (FIG. 2A). We exploited isogenic derivatives of these cell lines with either the WT or mutant alleles of PIK3CA knocked out (FIG. 2A). The clones in which the mutant allele had been disrupted and the wild-type allele was intact were called "wild-type" (WT, FIG. 2A), whereas the clones in which the WT allele had been disrupted and the mutant allele was intact were called "mutant" (Mut, FIG. 2A). As reported previously, the parent cells and knockout clones grew at similar rate under normal conditions in the presence of both glucose and glutamine (FIG. 2B). However, both parental cells and the PIK3CA mutant clones grew considerably more slowly in medium without glutamine than did PIK3CA WT clones (FIG. 2B). This relative sensitivity to glutamine deprivation was observed in both HCT116 and DLD1 cell lines containing mutant PIK3CA genes (FIG. 2B). Glutamine deprivation induced more apoptotic cells in the mutant clones than in 7 the WT clones as assayed by percentages of sub-G1 cells and amounts of cleaved PARP (FIGS. 2(C-D)). In contrast, none of these cell lines showed differential sensitivity to deprivation of glucose (FIG. 2B). To determine what we observed with the isogenic cell lines were generalizable, we tested glutamine sensitivity in two CRC cell lines with PIK3CA mutations [RZKO (containing a PIK3CA H1047R mutation) and HT29 (containing a PIK3CA P449T mutation)] and two CRC cell lines with WT PIK3CA (SW480 and LOVO). As shown in FIG. 2E, glutamine deprivation induced significantly more apoptotic cells in the two PIK3CA mutant cell lines than in the two WT PIK3CA cell lines. Consistently, when deprived of glutamine, relative survival rates of the two WT PIK3CA cell lines were higher than those of the two PIK3CA mutant cell lines. Taken together, the data suggest that PIK3CA mutations render CRC cells more dependent on glutamine for optimal growth.

The Up-Regulation of GPT2 by PIK3CA Mutations Renders CRC Cells Dependent on Glutamine To determine whether PIK3CA mutations regulate the transcription of enzymes involved in glutamine metabolism, we performed serial analysis of gene expression (SAGE) on the isogenic cell lines in the Appendix. Interestingly, the expression levels of mitochondrial glutamate pyruvate transaminase GPT2, which converts glutamate to α-KG, were up-regulated in both HCT116 and DLD1 PIK3CA-mutant clones compared to the WT clones. This observation was confirmed by both RT-PCR and Western blot analyses of the clones (FIGS. 3(A-B)). However, the cytosolic glutamate pyruvate transaminase GPT1 was not expressed or expressed at only an extremely low levels in the clones (FIG. 3A). None of the other enzymes primarily involved in glutamine metabolism including GOT1, GOT2, Glud1, GLS1 and GLS2, or the glutamine 8 transporter SLC1A5, exhibited any differential expression among the PIK3CA mutant and WT clones (FIG. 3A).

We next test if GPT2 expression is up-regulated in CRCs specimens with PIK3CA mutations. We thus measured GPT2 RNA levels by qRT-PCR in 21 human CRC patient tumors that we performed whole-exon sequencing previously (10 tumors with PIK3CA mutations and 10 tumors with no mutations in the PIK3CA pathway). As shown in FIG. 3C, expression levels of GPT2 were significantly higher in the tumors with PIK3CA mutation than in these tumors with WT PIK3CA.

To determine whether the up-regulation of GPT2 makes PIK3CA mutant cells dependent on glutamine, we knocked down GPT2 in the HCT116 mutant clone using two independent shRNAs, then grew the cells in normal medium or medium without glutamine. Compared to cells with a control shRNA, knockdown of GPT2 made the PIK3CA mutant cells less sensitive to glutamine deprivation as assayed by relative cell growth (FIG. 3D) and cell apoptosis, even though the GPT2 knockdown cells grew more slowly under normal growth conditions. In contrast, knockdown of GPT2 in the HCT116 PIK3CA WT clone had no effect on their sensitivity to glutamine deprivation or proliferation under normal culture conditions (FIG. 3E). Conversely, overexpression of GPT2 in the WT clone made it sensitive to glutamine deprivation. In aggregate, these data demonstrate that PIK3CA mutations render colorectal cancer cells more sensitive to glutamine withdrawal through an up-regulation of GPT2.

An Aminotransferase Inhibitor Suppresses the Growth of PIK3CA-Mutant CRC Cell Lines In Vivo AOA inhibits the enzymatic activity of aminotransferases including GPT220. As shown in FIG. 10a, both HCT116 and DLD1 PIK3CA mutant clones were more sensitive to AOA treatment than the WT clones in tissue culture. Moreover, AOA significantly inhibited the growth of HCT116 and DLD1 mutant clones when xenografted into nude mice (FIGS. 4(A-B)). In contrast, AOA had no effect on isogenic PIK3CA WT xenograft tumors (FIGS. 4(A-B)), although those tumors grew more slowly than their mutant counterparts in the absence of AOA (FIGS. 4(A-B)). To test whether our observations with the genetically engineered cell lines were generalizable, we expanded our xenograft study to a panel of CRC cell lines. AOA inhibited xenograft tumor growth of four PIK3CA-mutant CRC cell lines [HCT116 (parental cells), DLD1 (parental cells), RKO and HT29, FIG. 4C]. In contrast, AOA had no effect on xenograft tumor growth of two WT PIK3CA CRC cell lines (SW480 and LOVO, FIG. 4D). No weight loss was observed for the mice that were treated with AOA, suggesting that the doses of AOA used in the experiments had minimal toxicity. Consistent with the hypothesis that up-regulation of GPT2 by PIK3CA mutations renders colorectal cancer cells dependent on glutamine, GPT2 protein levels were higher in the PIK3CA mutant lines (HCT116, DLD1, RKO and HT29) than in the PIK3CA WT cell lines (SW480 and LOVO).

ATF4 Regulates Transcription of GPT2

Given that p110α is not a transcription factor, a key question raised by these data is how mutant p110α transduces the signals that activate GPT2 transcription. To address this question, we evaluated ATF4, as recent studies reported that ATF4 is involved in glutamine metabolism. Interestingly, ATF4 protein levels mirrored GPT2 protein levels in the PIK3CA mutant and WT clones (FIG. 5A). This correlation was maintained in xenograft tumors (FIG. 5B). In contrast, GLS protein levels were uncorrelated with ATF4 protein levels in the same cell lines (FIG. 5A). Because ATF4 induces expression of pro-apoptotic BH3-only proteins PUMA and Noxa in neuroblastoma cells, we also measured levels of these two proteins in the PIK3CA WT and mutant clones. However, PUMA and Noxa protein levels were not correlated with ATF4 levels (FIG. 5A), suggesting that the regulation of the two pro-apoptotic proteins by ATF4 may be celltype specific or controlled by other factors.

As shown in FIG. 5C, overexpression of ATF4 in the HTC116 PIK3CA WT clone increased GPT2 protein levels in a dose-dependent manner. Conversely, knockdown of ATF4 in the HCT116 PIK3CA mutant clone by two different siRNAs reduced both mRNA and protein levels of GPT2 (FIG. 5D). In contrast, knockdown of ATF4 did not affect the expression of other enzymes involved in glutamine metabolism, including SLC1A5, GLS1, GOT1, GOT2 and GLUD1 (FIG. 5A). Similar results were observed in both HCT116 and DLD1 PIK3CA mutant clones Importantly, as in the case with GPT2, the knockdown of ATF4 made PIK3CA mutant cells more resistant to glutamine deprivation as assessed by both cell survival and cell death (FIG. 5E), even though the ATF4 knockdown cells grew more slowly than the control cells in the presence of glutamine. These results suggest that the mutant p110α-ATF4-GPT2 axis regulates glutamine metabolism.

To determine whether ATF4 activates GPT2 gene transcription directly, we cloned a 1.5 kb genomic upstream of the transcription start site of the GPT2 gene into a luciferase reporter 11 plasmid. As shown in FIG. 4f, knockdown of ATF4 in the HCT116 PIK3CA mutant clone reduced transcriptional activity of the GPT2 reporter (FIG. 5F). Examining the DNA sequences in the 1.5 kb genomic DNA fragment of GPT2, we found two sequences matching ATF4 consensus binding sites (FIG. 5G). Mutating either or both of the two candidate sites significantly diminished ATF4-mediated transcriptional activity (FIG. 5H).

Mutant p110α Stabilizes the ATF4 Protein

We next sought to determine how ATF4 is differentially regulated in PIK3CA-mutant and WT cells. We first showed that ATF4 mRNA levels were similar in isogenic PIK3CA mutant and WT cell clones. The ATF4 protein is known to be induced by stress through phosphoelF2α (p-eIF2α)-dependent translation initiation of upstream open reading frames (uORF). To investigate whether mutant p110α upregulates ATF4 protein levels through this mechanism, we examined p-eIF2α levels in the PIK3CA mutant and WT clones. Similar levels of p-eIF2α were observed in the PIK3CA mutant and WT cells. This result was consistent with the uORF reporter assays indicating that the upstream ORF initiation activity of ATF4 was similar in the HCT116 PIK3CA mutant and WT cells. Moreover, polysome profiling of ATF4 mRNA showed no significant difference between HCT116 PIK3CA mutant and WT clones. We also tested whether mutant p110α affected ATF4 protein stability by regulating its ubiquitination. As shown in FIGS. 6(A-B), the ubiquitination levels of both endogenous and ectopically overexpressed ATF4 were much higher in the HCT116 PIK3CA WT clone than in the mutant cells. As expected, exposure to a PI3K inhibitor (LY294002), a PI3K/mTOR dual inhibitor (DEZ235) and a PDK1 inhibitor (GSK2334470) each reduced ATF4 protein levels (FIG. 6C). Surprisingly, neither an AKT inhibitor (GSK690693) nor an inhibitor (CHIR-99021) of GSK3β(a known downstream effector of AKT) had any effect on ATF4 protein levels (FIG. 6C). In accord with this, expression of a constitutively active form of AKT1 (myristylated-AKT1) in the PIK3CA WT clone did not affect ATF4 or GPT2 proteins levels. As a control for these experiments, we found that myristylated-AKT1 did increase the phosphorylation level of FOXO1, a well-known AKT kinase target.

Interestingly, ATF4 is reported to be a substrate of RSK2. Although it is not as well-known an effector of PIK3CA as AKT, PDK1 also regulates the RSK2 kinase. Indeed, both a pan RSK inhibitor (BI-D1870) and a more selective RSK2 inhibitor (FMK) reduced ATF4 protein levels in the HCT116 PIK3CA mutant clone (FIG. 6C). Therefore, these data suggest a p110α-PDK1-RSK2 pathway that regulates ATF4 protein levels (FIG. 6D).

To confirm the results obtained with the inhibitors, we first overexpressed p110α E545K and H1047R mutant constructs in the HCT116 PIK3CA WT clone. We found that overexpression of mutant p110α increased both ATF4 and GPT2 protein levels (FIG. 6E). We then attempted to ascertain whether the lipid kinase activity of p110α is required for the mutant p110α signaling pathway to stabilize the ATF4 protein. For this purpose, we knocked in a D933A mutation that inactivates its lipid kinase activity on top of the E545K mutant allele into the DLD1 PIK3CA mutant clone. FIG. 6F shows that the protein levels of both ATF4 and GPT2 were reduced in the double mutant clones. As expected, AKT phosphorylation levels were also 13 reduced in the double mutant cells Importantly, the kinase inactivation mutation rendered the DLD1 PIK3CA E545K mutant clone less sensitive to glutamine deprivation (FIG. 6G). Moreover, knockdown of either PDK1 or RSK2 in the HCT116 PIK3CA mutant clone reduced ATF4 and GPT2 protein levels (FIGS. 6(H-I)).

Phosphorylation of ATF4 at S245 by RSK2 Recruits Deubiquitinase USP8 to Protect ATF4 from Degradation RSK2 is a serine/threonine kinase that phosphorylates ATF4 at the serine 245 residue (S245). Knockdown of RSK2 in HCT116 PIK3CA mutant clone reduced levels of pS245 ATF4 (FIG. 7A). Therefore, we hypothesized that phosphorylation of ATF4 at S245 by the mutant p110α-PDK1-RSK2 signaling axis stabilizes ATF4. To test this hypothesis, we first examined ATF4 S245 phosphorylation in the HCT116 PIK3CA WT and mutant clones. As expected, levels of pS245 ATF4 were higher in the mutant clone than in the WT clone (FIG. 7B). Second, compared to the expression of a WT ATF4 construct, the expression of an unphosphorylatable ATF4 S245A mutant construct in the HCT116 PIK3CA mutant clone resulted in less ATF4 protein (FIG. 7C). In contrast, the ATF4 S219A mutant that abolishes the binding of ATF4 to β-TrCP1, an ubiquitin E3 ligase of ATF421, generated more protein than the WT counterpart (FIG. 7C). Consistent with our hypothesis that phosphorylation of ATF4 at the S245 residue stabilizes it, the ubiquitination levels of the ATF4 S245A mutant were higher than that of the WT protein (FIG. 7D). These data led us to postulate that phosphorylation of ATF4 S245 by RSK2 either reduces its binding affinity to an ubiquitin E3 ligase or recruits a deubiquitinase, thereby protecting ATF4 from degradation. To this end, we first tested the binding of WT and S245A mutant ATF4 to β-TrCP1. However, both WT and the mutant ATF4 bound to a similar amount of β-TrCP1. We 14 then turned our attention to deubiquitinases and tested the binding of the WT ATF4 and S245A mutant to eight USPs (USP1, USP2, USP7, USP8, USP9X, USP10, USP14 and USP18). Among the USPs tested, only USP8 exhibited differential binding to WT vs mutant ATF4 (FIG. 7E). Consistent with our hypothesis, the ATF4 S245A mutant bound to less USP8 than WT ATF4 (FIG. 7E). Knockdown of UPS8 by two independent siRNAs in the HCT116 PIK3CA mutant clone resulted in reduced ATF4 protein levels (FIG. 7F) and increased ATF4 ubiquitination (FIG. 7G).

TCA Cycle Metabolites are Higher in PIK3CA-Mutant Clones than in Isogenic WT Clones Both the HCT116 and DLD1 mutant clones consumed more glutamine than their WT counter parts. Glutamine is converted to α-KG to replenish the TCA cycle. Because GPT2, an enzyme that converts glutamate to α-KG, is up-regulated in PIK3CA mutant CRC cells (FIG. 3A), we profiled TCA cycle intermediates in the paired isogenic lines. PIK3CA mutant and WT cells were exposed to 2 mM of [$^{13}C_5$-]glutamine in the presence of glucose for 2 hours and the enrichment of the isotope-labeled TCA cycle intermediates was measured by GCMS. All of the measured $^{13}$C-labeled TCA cycle metabolites, including α-KG, succinate, fumarate, malate and citrate, were significantly higher in the PIK3CA mutant clones than in the WT clones. Conversely, the unlabeled TCA cycle intermediates were significantly lower in the PIK3CA mutant clones than in the WT clones. Similar results were observed with clones derived from both HCT116 and DLD1. We next examined the steady state of glutamine-derived TCA cycle intermediates by culturing the HCT116 and DLD1 PIK3CA WT and mutant clones in [$^{13}C_5$-]glutamine-containing medium for 24 hours. The results showed that: (i) the majority of the TCA cycle intermediates 15 were derived from glutamine in both PIK3CA mutant and WT cells (FIG. 8A), consistent with the "Warburg effect"; and (ii) compared to the WT clones, the amounts of α-KG and citrate were significantly higher in the mutant clones (FIG. 8A).

A major product of the forward TCA cycle is NADH, which couples with oxidative phosphorylation to generate ATP. We therefore measured the amounts of ATP and NADH in the PIK3CA WT and mutant clones. In the presence of glutamine, the amounts of ATP and NADH were significantly higher in both the HCT116 and DLD1 mutant clones than in their WT counterparts (FIGS. 8(B-C)). The ratios of NADH/NAD were also significantly higher in the mutant clones than in the WT clones. Although not statistically significant, the ATP/ADP ratios appeared to be higher in the mutant clones. However, under glutamine deprivation, the amount of ATP and the ATP/ADP ratio were significantly lower in the mutant clones than in the WT clones (FIG. 8), whereas the amounts of NADH and the ratios of NADH/NAD were similar in the mutant and WT clones (FIG. 8C).
The Addition of α-KG Rescues Survival of PIK3CA Mutant Cells Deprived of Glutamine The results described above show that the generation of α-KG from glutamine to replenish the TCA cycle was critical to the survival of the PIK3CA mutant cells. To test this suggestion, we deprived the HCT116 PIK3CA mutant cell of glutamine and then supplemented the cells with 4 mM α-KG. When deprived of glutamine, less than 8% cells survived after 3 days (FIG. 8D). In contrast, the addition of α-KG increased cell survival to ~60%.
AOA May Synergize with 5-FU to Inhibit Xenograft Tumor Growth To determine if AOA can enhance the efficacy of existing colorectal cancer drugs, we tested combination of AOA (10 mg/kg) with 5-FU, irinotecan, oxaliplatin or regorafenib on xenograft tumors established HCT116. As shown in FIG. 10, combination of AOA with 5-FU at a dose of 10 mg/kg or 20 mg/kg appeared to have synergistic tumor inhibitory effect, although higher doses of 5-FU need to be tested to determine the synergy. In contrast, none of the other drug showed any combinational effect with AOA.
$IC_{50}$ of AOA to GPT2

We have demonstrated that AOA preferentially inhibits xenograft tumor growth of colorectal cancers with PIK3CA mutations. However, AOA is pan-transaminase inhibitor. As shown in FIG. 11A, we have developed a GPT2 enzymatic assay that can be easily adapted for high-throughput screening. The $IC_{50}$ of AOA to GPT2 is 980 nM (FIG. 11B). Therefore, more potent and specific GPT2 inhibitor can be developed. Moreover, AOA treatment at a dose of 10 mg/kg, which resulted in significant growth inhibition of xenograft tumors established from colorectal cancers harboring PIK3CA mutations, only inhibited GPT activity by ~30% in the AOA treated tumors as assayed by the amounts of α-KG (a product of GPT2, FIG. 12C). Together, our data suggest that a more potent and specific GPT2 inhibitor should be more effective and less toxic than AOA.
Combination of CB-839 with 5-FU Shrinks PIK3CA Mutant Xenograft Tumors As discussed above, CB-839 is a potent glutaminase inhibitor that blocks the first step of glutamine metabolism. CB-839 is currently in phase I clinical trials for several cancer types, but not colorectal cancer. We set out to determine if CB-839 alone or in combination with 5-FU inhibits xenograft tumor growth of a PIK3CA mutant CRC. As shown in FIG. 12, the CB-389 and 5-FU combination treatment induced tumor regression (2 out of 10 tumors regressed after two weeks of treatment, 3 more tumors regressed after three weeks of treatment, and other tumors stopped growing after two weeks of treatment). In contrast, although CB-839 or 5-FU alone inhibited tumor growth to various extents, neither induced tumor regression (FIG. 12B). In summary, these preliminary results provide a strong rationale for clinical trials of combination therapy of CB-839 with 5-FU in CRCs with PIK3CA mutations.
PIK3CA Mutations Render Cancer Cells Sensitive to EGCG and BPTES Epigallocatechin gallate, an active component of green tea extract, has been shown to inhibit glutamine dehydrogenase, whereas BPTES inhibits glutaminase activity. To test if PIK3CA mutations render cancer cell sensitive to these inhibitors, we treated PIK3CA-/mut, PIK3CA WT/- HCT116 and DLD1 colon cancer cells with various doses of EGCG and BPTES. As shown in FIG. 13, both HCT116 and DLD1 PIK3CA-/mut cells are more sensitive to growth inhibition by EGCG and BPTES in tissue culture.

The data thus demonstrate that oncogenic PIK3CA mutations reprogram glutamine metabolism through the up-regulation of GPT2 in CRCs. Although it has been previously shown that WT K-ras regulates glutamine metabolism in pancreatic cancers by an up-regulation of aminotransferase GOT112, it is not clear that oncogenic K-ras mutations render cancer cells more sensitive to glutamine deprivation. Moreover, both SW480 and LOVO CRC cell lines harbor oncogenic K-ras mutations, but the two cell lines were resistant to glutamine deprivation (FIG. 2E). Thus our data suggest that mutant K-ras is not a key determinant of glutamine dependency in CRCs. In contrast, the data provide compelling evidence that oncogenic PIK3CA mutations in CRCs render them more sensitive to glutamine deprivation.

Our data also show that CRC cells harboring PIK3CA mutations, but not those cells with WT PIK3CA, are sensitive to growth inhibition by AOA, a compound that blocks the conversion of glutamate to α-KG. These findings constitute a proof-of-principle that targeting glutamine metabolism can be a useful approach to treating cancers, such as CRCs, harboring PIK3CA mutations. Our results show that targeting glutamine metabolism can afford a specific form of therapy for cancer patients harboring PIK3CA mutations.

This Example demonstrates that GPT2 is the key determinant of glutamine sensitivity in PIK3CA mutant CRC cells. GPT2 is an aminotransaminase that converts glutamate to α-KG, which is a TCA cycle intermediate. Metabolic profiling shows that amounts of α-KG are significantly higher in the PIK3CA mutant clones than in the WT clones and that the other TCA cycle intermediates are also higher in the mutant clones than in the WT clone. Moreover, α-KG largely rescues PIK3CA mutant cells from cell death caused by glutamine deprivation, showing that α-KG is a key metabolite required for PIK3CA-mutant cell growth. Together, these data show that up-regulation of GPT2 by PIK3CA mutations produces more α-KG from glutamine to replenish the TCA, thereby generating more ATP and intermediates for macromolecule synthesis to sustain rapid growth of PIK3CA mutant tumors. This is consistent with the observation that both the ATP concentration and the ATP/ADP ratios were higher in the PIK3CA mutant cells than in the WT cells. We also showed that AOA, a pan-aminotransferase inhibitor, suppresses xenograft tumor growth of PIK3CA mutant CRCs.

It is generally believed that AKTs are the key mediators of the oncogenic signaling of PI3Ks. This Example however describes a novel p110α-PDK1-RSK2-ATF4-GPT2 pathway that regulates glutamine metabolism. We demonstrated that blocking this pathway inhibits PIK3CA mutant tumor growth in vitro and in vivo, suggesting that this novel signaling pathway also plays a critical role in tumorigenesis driven by PIK3CA mutations.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of determining the susceptibility and/or responsiveness of cancer cells, precancerous cells, and/or benign tumor cells of a subject to treatment with an inhibitor of one or more enzymes of a glutamine metabolism pathway of the cancer cells, the precancerous cells, and/or the benign tumor cells, comprising:

obtaining a sample of the cancer cells, the precancerous cells, and/or the benign tumor cells from the subject;

assaying the cancer cells, the precancerous cells, and/or the benign tumor cells for the presence a mutated PIK3CA gene or a mutant form of PIK3CA protein or a biologically active fragment thereof;

determining that the cancer cells, precancerous cells, and/or benign tumor cells of the subject are more or less susceptible and/or responsive to the inhibitor of one or more enzymes of a glutamine metabolism pathway, wherein the subject should be treated with the inhibitor if the cancer cells, the precancerous cells, and/or benign tumor cells have the mutated PIK3CA gene or the mutant form of PIK3CA protein or a biologically active fragment thereof; and administering the inhibitor to cancer cells, the precancerous cells, and/or benign tumor cells of the subject having the mutated PIK3CA gene or the mutant form of PIK3CA protein or a biologically active fragment thereof, wherein the inhibitor comprises at least one of a glutaminase inhibitor or an aminotrasferase inhibitor.

2. The method of claim 1, wherein cancer cells and the precancerous cells are obtained from a tumor or biological sample of the subject.

3. The method of claim 1, wherein a mutation is detected using an amplification assay or by molecular cloning or sequencing or microarray analysis.

4. The method of claim 1, wherein the PIK3CA gene in the sample is amplified by polymerase chain reaction or ligase chain reaction.

5. The method of claim 1, wherein a DNA hybridization assay is used to detect the PIK3CA gene in the sample.

6. The method of claim 1, wherein the cancer cells are selected from the group consisting of lung cancer, digestive and gastrointestinal cancers, gastrointestinal stromal tumors, gastrointestinal carcinoid tumors, colon cancer, rectal cancer, anal cancer, bile duct cancer, small intestine cancer, and stomach (gastric) cancer, esophageal cancer, gall bladder cancer, liver cancer, pancreatic cancer, appendix cancer, breast cancer, ovarian cancer, renal cancer, cancer of the central nervous system, skin cancer, lymphomas, choriocarcinomas, head and neck cancers, osteogenic sarcomas, and blood cancers.

7. The method of claim 1, wherein the inhibitor comprises aminooxyacetate (AOA).

8. The method of claim 1, wherein the inhibitor comprises at least one of bis-2-(5-phenylacetamido-1,2,4-thiadiazol-2-yl)ethyl sulfide or CB-839.

9. A method of treating a subject having cancer, precancerous cells, or a benign tumor that has a mutated PIK3CA gene or protein, the method comprising:

determining that the subject has cancer cells that have the mutated PIK3CA gene or a mutant form of PIK3CA protein or a biologically active fragment thereof by:

obtaining a sample of cancer cells, precancerous cells, and/or benign tumor cells from the subject; and assaying the cancer cells, the precancerous cells, and/or the benign tumor cells for the presence a mutated PIK3CA gene or a mutant form of PIK3CA protein or a biologically active fragment thereof; and administering to the subject a therapeutically effective amount of an inhibitor of one or more enzymes of a glutamine metabolism pathway of the cancer cells, wherein the inhibitor comprises at least one of a glutaminase inhibitor or an aminotransferase inhibitor.

10. The method of claim 9, wherein the inhibitor comprises aminooxyacetate (AOA).

11. The method of claim 9, wherein the inhibitor comprises at least one of bis-2-(5-phenylacetamido-1,2,4-thiadiazol-2-yl)ethyl sulfide or CB-839.

12. The method of claim 9, wherein the cancer cells are determined to have the mutated PIK3CA gene or the mutant form of PIK3CA protein or a biologically active fragment thereof prior to administration of the inhibitor.

13. The method of claim 9, wherein the PIK3CA gene in the sample is amplified by polymerase chain reaction or ligase chain reaction.

14. The method of claim 9, wherein a DNA hybridization assay is used to detect the PIK3CA gene in the sample.

15. A method of treating a subject having cancer, precancerous cells, or a benign tumor that has mutated PIK3CA gene or a mutant form of PIK3CA protein, the method comprising determining that the cancer cells, the precancerous cells, and/or benign tumor cells have the mutated PIK3CA gene or the mutant form of PIK3CA protein or a biologically active fragment thereof, and administering to the subject having cancer cells, precancerous cells, and/or benign tumor cells having the mutated PIK3CA gene or a mutant form of PIK3CA protein a therapeutically effective amount of an inhibitor of one or more enzymes of a glutamine metabolism pathway, wherein the inhibitor comprises at least one of a glutaminase inhibitor or an aminotransferase inhibitor.

16. The method of claim 15, wherein the determining step includes:

obtaining a sample of cancer cells, precancerous cells, and/or benign tumor cells from the subject; and assaying the cancer cells, the precancerous cells, and/or the benign tumor cells for the presence of a mutated PIK3CA gene or a mutant form of PIK3CA protein or a biologically active fragment thereof.

17. The method of claim 1, wherein the inhibitor is administered with at least one of capecitabine and 5-fluorouracil.

18. The method of claim 9, wherein the inhibitor is administered with at least one of capecitabine and 5-fluorouracil.

19. The method of claim 15, wherein the inhibitor is administered with at least one of capecitabine and 5-fluorouracil.

* * * * *